(12) United States Patent
Yan et al.

(10) Patent No.: US 9,202,867 B2
(45) Date of Patent: Dec. 1, 2015

(54) NANOCRYSTALS CONTAINING CDTE CORE WITH CDS AND ZNS COATINGS

(71) Applicants: Hao Yan, Chandler, AZ (US); Zhengtao Deng, Tempe, AZ (US); Yan Liu, Chandler, AZ (US)

(72) Inventors: Hao Yan, Chandler, AZ (US); Zhengtao Deng, Tempe, AZ (US); Yan Liu, Chandler, AZ (US)

(73) Assignee: Arizona Board of Regents, Scottsdale, AZ (US)

( * ) Notice: Subject to any disclaimer, the term of this patent is extended or adjusted under 35 U.S.C. 154(b) by 0 days.

(21) Appl. No.: 14/238,775

(22) PCT Filed: Oct. 3, 2012

(86) PCT No.: PCT/US2012/058548
§ 371 (c)(1),
(2) Date: Feb. 13, 2014

(87) PCT Pub. No.: WO2013/052541
PCT Pub. Date: Apr. 11, 2013

(65) Prior Publication Data
US 2014/0252316 A1  Sep. 11, 2014

Related U.S. Application Data

(60) Provisional application No. 61/543,126, filed on Oct. 4, 2011.

(51) Int. Cl.
*C09K 11/08* (2006.01)
*H01L 29/06* (2006.01)
(Continued)

(52) U.S. Cl.
CPC .............. *H01L 29/0669* (2013.01); *B82Y 5/00* (2013.01); *B82Y 10/00* (2013.01); *B82Y 15/00* (2013.01); *B82Y 30/00* (2013.01); *B82Y 40/00* (2013.01);
(Continued)

(58) Field of Classification Search
CPC ..... H01L 33/06; H01L 33/502; H01L 33/504; H01L 29/0669
USPC ............. 257/100, 433; 252/301.6 S, 301.6 R; 313/501, 502, 503; 977/755, 762, 773, 977/774
See application file for complete search history.

(56) References Cited

U.S. PATENT DOCUMENTS 6,322,901 B1  11/2001  Bawendi et al.
7,678,359 B2   3/2010  Chung et al.
(Continued)

FOREIGN PATENT DOCUMENTS

WO    WO 2005/001889    1/2005

OTHER PUBLICATIONS

Smith et al., Semiconductor nanocrystals: structure, properties, and band gap engineering, Accounts of Chemical Research, Feb. 2010, vol. 43, No. 2, pp. 190-200.
(Continued)

*Primary Examiner* — Minh-Loan Tran
(74) *Attorney, Agent, or Firm* — McDonnell Boehnen Hulbert & Berghoff LLP

(57) ABSTRACT

Described are CdTe/CdS/ZnS core/shell/shell nanocrystals, methods for making the same, and their use in biomedical and photonic applications, such as sensors for analytes in cells and preparation of field effect transistors. In particular, the disclosure provides a nanocrystal having a CdTe core, a CdS coating over the core, and a ZnS core over the CdS coating, where the nanocrystal has a photoluminescence maximum between about 650 nm and 900 nm.

9 Claims, 26 Drawing Sheets

(51) Int. Cl.

| | |
|---|---|
| C09K 11/54 | (2006.01) |
| C09K 11/02 | (2006.01) |
| C09K 11/56 | (2006.01) |
| C09K 11/57 | (2006.01) |
| C09K 11/66 | (2006.01) |
| C09K 11/88 | (2006.01) |
| C01B 19/00 | (2006.01) |
| H01L 29/12 | (2006.01) |
| H01L 29/22 | (2006.01) |
| B82Y 5/00 | (2011.01) |
| B82Y 30/00 | (2011.01) |
| B82Y 40/00 | (2011.01) |
| C01G 19/00 | (2006.01) |
| G01N 33/58 | (2006.01) |
| H01L 29/66 | (2006.01) |
| H01L 29/775 | (2006.01) |
| B82Y 10/00 | (2011.01) |
| B82Y 15/00 | (2011.01) |

(52) U.S. Cl.
CPC .............. *C01B 19/002* (2013.01); *C01B 19/007* (2013.01); *C01G 19/00* (2013.01); *C09K 11/02* (2013.01); *C09K 11/08* (2013.01); *C09K 11/0811* (2013.01); *C09K 11/54* (2013.01); *C09K 11/565* (2013.01); *C09K 11/574* (2013.01); *C09K 11/661* (2013.01); *C09K 11/883* (2013.01); *G01N 33/588* (2013.01); *H01L 29/122* (2013.01); *H01L 29/127* (2013.01); *H01L 29/22* (2013.01); *H01L 29/66977* (2013.01); *H01L 29/775* (2013.01); *C01P 2002/72* (2013.01); *C01P 2002/84* (2013.01); *C01P 2002/85* (2013.01); *C01P 2004/04* (2013.01); *C01P 2004/16* (2013.01); *C01P 2004/17* (2013.01); *C01P 2004/64* (2013.01); *C01P 2004/86* (2013.01); *C01P 2004/88* (2013.01); *Y10T 428/12431* (2015.01); *Y10T 428/294* (2015.01)

(56) References Cited

U.S. PATENT DOCUMENTS

| | | | |
|---|---|---|---|
| 7,867,557 B2 | 1/2011 | Pickett et al. | |
| 2005/0012182 A1 | 1/2005 | Jang et al. | |
| 2007/0200479 A1* | 8/2007 | Jean et al. | 313/483 |
| 2010/0140586 A1 | 6/2010 | Char et al. | |
| 2010/0176715 A1 | 7/2010 | Bawendi et al. | |
| 2011/0031452 A1 | 2/2011 | Krauss et al. | |
| 2011/0233468 A1 | 9/2011 | Zong et al. | |

OTHER PUBLICATIONS

Soci et al., Nanowire photodetectors, Journal of Nanoscience and Nanotechnology, 2010, vol. 10, No. 3, pp. 1430-1449.
Sugiyama et al., Band offset of SnS solar cell structure measured by X-ray photoelectron spectroscopy, Thin Solid Films, 2011, vol. 519, pp. 7429-7431.
Talapin et al., Prospects of colloidal nanocrystals for electronic and optoelectronic applications, Chemical Reviews, 2010, vol. 110, No. 1, pp. 389-458.
Tong et al., Bright three-photon luminescence from Au—Ag alloyed nanostructures for bioimaging with negligible photothermal toxicity, Angewandte Chemie Int Ed, May 2010, vol. 49, No. 20, pp. 3485-3488.
Vaughn et al., A precursor-limited nanoparticle coalescence pathway for tuning the thickness of laterally-uniform colloidal nanosheets: the case of SnSe, ACS Nano, 2011, vol. 5, No. 11, pp. 8852-8860.
Vidal et al., Band-structure optical properties, and defect physics of the photovoltaic semiconductor SnS, Applied Physics Letters, 2012, vol. 100, 032104.
Wang et al., The application of SnS nanoparticles to bulk heterojunction solar cells, Journal of Alloys and Compounds, 2009, vol. 482, pp. 203-207.
Xia et al., Ultrafast graphene photodetector, Nature Nanotechnology, Dec. 2009, vol. 4, pp. 839-843.
Xu et al., Synthesis of SnS quantum dots, Journal of the American Chemical Society, 2009, vol. 131, pp. 15990-15991.
Yin et al., Single-layer MoS2 phototransistors, ACS Nano, 2012, vol. 6, No. 1, pp. 74-80.
Yue et al., Characterization and optical properties of the single crystalline SnS nanowire arrays, Nanoscale Research Letters, 2009, vol. 4, pp. 359-363.
Zeng et al., "White graphenes": Boron nitride nanoribbons via boron nitride nanotube unwrapping, Nano Letters, 2010, vol. 10, pp. 5049-5055.
Zhai et al., Recent developments in one-dimensional inorganic nanostructures for photodetectors, Advanced Functional Materials, 2010, vol. 20, pp. 4233-4248.
Zhang et al., Ultralarge single crystal SnS rectangular nanosheets, Chemical Communications, 2011, vol. 47, pp. 5226-5228.
Zheng et al., Observation of transient structural-transformation dynamics in a Cu(2)S nanorod, Science, Jul. 2011, vol. 333, pp. 206-209.
Zhu et al., Two-dimensional SnS nanosheets fabricated by a novel hydrothermal method, Journal of Materials Science, 2005, vol. 40, pp. 591-595.
Coleman et al., Two-dimensional nanosheets produced by liquid exfoliation of layered materials, Science, Feb. 2011, vol. 331, pp. 568-571.
International Search Report for PCT/US2012/058548, mailed Apr. 4, 2013.
Alivisatos, Semiconductor clusters, nanocrystals, and quantum dots, Science, Feb. 1996, vol. 271, No. 5251, pp. 933-937.
Antunez et al., Tin and germanium monochalcogenide IV-VI semiconductor nanocrystals for use in solar cells, Nanoscale, 2011, vol. 3, pp. 2399-2411.
Bae et al., Single-step synthesis of quantum dots with chemical composition gradients, Chemistry of Materials, Jan. 2008, vol. 20, No. 2, pp. 531-539.
Baumgardner et al., SnSe nanocrystals: synthesis, structure, optical properties, and surface chemistry, Journal of the American Chemical Society, 2010, vol. 132, pp. 9519-9521.
Brus, Solid state chemistry—metastable dense semiconductor phases, Science, Apr. 1997, vol. 276, pp. 373-374.
Chen et al., A multimodal platform for nonlinear optical microscopy and microspectroscopy, Optics Express, Feb. 2009, vol. 17, No. 3, pp. 1282-1290.
Chen et al., Novel boron nitride hollow nanoribbons, ACS Nano, 2008, vol. 2, No. 10, pp. 2183-2191.
Coropceanu et al., Charge transport in organic semiconductors, Chemical Reviews, 2007, vol. 107, pp. 926-952.
Deng et al., A new route to Zinc-blende CdSe nanocrystals: mechanism and synthesis, Journal of Physical Chemistry B, 2005, vol. 109, pp. 16671-16675.
Deng et al., Aqueous synthesis of zinc blende CdTe/CdS magic-core/thick-shell tetrahedrol-shaped nanocrystals with emission tunable to near-infrared, Journal of the American Chemical Society, 2010, vol. 132, pp. 5592-5593.
Deng et al., Band gap engineering of quaternary-alloyed ZnCdSSE quantum dots via a facile phosphine-free colloidal method, Journal of the American Chemical Society, 2009, vol. 131, pp. 17744-17745.
Deng et al., Colloidal synthesis of metastable zinc-blende IV-VI SnS nanocrystals with tunable sizes, Nanoscale 2011, vol. 3, pp. 4346-4351.
Deng et al., Controlled colloidal growth of ultrathin single-crystal ZnS nanowires with a magic-size diameter, Angewandte Chemie Int Ed, 2010, vol. 49, pp. 8695-8698.
Deng et al., High-quality manganese-doped zinc sulfide quantum rods with tunable dual-color and multiphon emissions, Journal of the American Chemical Society, Apr. 2011, vol. 133, 5389-5396.

(56) References Cited

OTHER PUBLICATIONS

Deng et al., Simple colloidal synthesis of single-crystal Sb—Se—S nanotubes with composition dependent band-gap energy in the near-infrared, Nano Letters, 2009, vol. 9, No. 5, pp. 2015-2020.
Deng et al., Spherical hexagonal tellurium nanocrystals: fabrication and size-dependent structural phase transition at high pressure, Nanotechnology, 2008, vol. 19, 045707.
Deng et al., Strong blue photoluminescence from single-crystalline bismuth oxychloride nanoplates, Nanotechnology, 2008, vol. 19, 295705.
Devika et al., Ohmic contacts to SnS films: selection and estimation of thermal stability, Journal of Applied Physics, 2008, vol. 104, 124503.
Dietz et al., Folding DNA into twisted and curved nanoscale shapes, Science, Aug. 2009, vol. 325, pp. 725-730.
Donega et al., Synthesis and properties of colloidal heteronanocrystals, Chemical Society Reviews, 2011, vol. 40, pp. 1512-1546.
Douglas et al., Self-assembly of DNA into nanoscale three-dimensional shapes, Nature, May 2009, vol. 459, pp. 414-418.
Ehlert et al., A four-color colloidal multiplexing nanoparticle system, ACS Nano, 2008, vol. 2, No. 1, pp. 120-124.
Fafarman et al., Thiocyanate-capped nanocrystal colloids: vibrational reporter of surface chemistry and solution-based route to enhanced coupling in nanocrystal solids, Journal of the American Chemical Society, 2011, vol. 133, pp. 15753-15761.
Franzman et al., Solution-phase synthesis of SnSe nanocrystals for use in solar cells, Journal of the American Chemical Society, 2010, vol. 132, pp. 4060-4061.
Habas et al., Low-cost inorganic solar cells: from ink to printed device, Chemical Reviews, 2010, vol. 110, No. 11, pp. 6571-6594.
Han et al., Energy band-gap engineering of graphene nanoribbons, Physical Review Letters, 2007, vol. 98, 206805.
Higginbotham et al., Lower-defect graphene oxide nanoribbons from multiwalled carbon nanotubes, ACS Nano, 2010, vol. 4, No. 4, pp. 2059-2069.
Jiang et al., Photoresponse properties of CdSe single-nanoribbon photodetectors, Advanced Functional Materials, 2007, vol. 17, pp. 1795-1800.
Jie et al., Photoconductive characteristics of single-crystal CdS nanoribbons, Nano Letters, 2006, vol. 6, No. 9, pp. 1887-1892.
Johnson et al., Optimization of photoconductivity in vaccum-evaporated tin sulfide thin films, Semiconductor Science and Technology, 1999, vol. 14, pp. 501-507.
Kang et al., Superior rate capabilities of SnS nanosheet electrodes for Li ion batteries, Electrochemistry Communications, 2010, vol. 12, pp. 307-310.
Ke et al., Multilayer DNA origami packed on a square lattice, Journal of the American Chemical Society, Nov. 2009, vol. 131, No. 43, 15903.
Kind et al., Nanowire ultraviolet photodetectors and optical switches, Advanced Materials, Jan. 2002, vol. 14, No. 2, pp. 158-160.
Koh et al., Thiocyanate-capped PbS nanocubes: ambipolar transport enables quantum dot based circuits on a flexible substrate, Nano Letters, 2009, vol. 9, pp. 1689-1693.
Koktysh et al., Synthesis of SnS nanocrystals by the solvothermal decomposition of a single source precursor, Nanoscale Research Letters, 2007, vol. 2, pp. 144-148.
Konstantatos et al., Sensitive solution-processed visible wavelength photodetectors, Nature Photonics, Sep. 2007, vol. 1, pp. 531-534.
Kosynkin et al., Highly conductive graphene nanoribbons by longitudinal splitting of carbon nanotubes using potassium vapor, ACS Nano, 2011, vol. 5, No. 2, pp. 968-974.
Li et al., Chemically derived, ultrasmooth graphene nanoribbon semiconductors, Science, Feb. 2008, vol. 319, pp. 1229-1232.
Nag et al., Metal-free inorganic ligands for colloidal nanocrystals: $S(2-)$, $HS(-)$, $Se(2-)$, $HSe(-)$, $Te(2-)$, $THe(-)$, $TeS(3)(2-)$, $OH(-)$, and $NH(2)(-)$ as surface ligands, Journal of the American Chemical Society, 2011, vol. 133, 10612-10620.
Ning et al., Shape and size controlled synthesis and properties of colloidal IV-VI SnSe nanocrystals, CrystEngComm, 2011, vol. 13, pp. 4161-4166.
Panda et al., Surfactant-assisted synthesis of SnS nanowires grown on tin foils, Crystal Growth and Design, 2006, vol. 6, No. 9, pp. 2177-2181.
Polking et al., Size-dependent polar ordering in colloidal GeTe nanocrystals, Nano Letters, 2011, vol. 11, pp. 1147-1152.
Radisavljevic et al., Single-layer MoS(2) transistors, Nature Nanotechnology, Mar. 2011, vol. 6, pp. 147-150.
Reddy et al., Growth of orthorhombic SnS nanobox structures on seeded substrates, Crystal Growth and Design, 2010, vol. 10, pp. 4769-4772.
Rothemund, Folding DNA to create nanoscale shapes and patterns, Nature, Mar. 2006, vol. 440, pp. 297-302.
Schwierz, Graphene transistors, Nature Nanotechnology, Jul. 2010, vol. 5, pp. 487-496.
Sharma et al., Control of self-assembly of DNA tubules through integration of gold nanoparticles, Science, Jan. 2009, vol. 323, No. 5910, pp. 112-116.
Sharma et al., DNA-Templated self-assembly of two-dimensional and periodical gold nanoparticle arrays, Angewandte Chemie Int Ed, 2006, vol. 45, pp. 730-735.
Sharma et al., Toward reliable gold nanoparticle patterning on self-assembled DNA nanoscaffold, Journal of the American Chemical Society, 2008, vol. 130, pp. 7820-7821.
Sinitskii et al., Kinetics of diazonium functionalization of chemically converted graphene nanoribbons, ACS Nano, 2010, vol. 4, No. 4, pp. 1949-1954.

\* cited by examiner

NANOCRYSTALS CONTAINING CDTE CORE WITH CDS AND ZNS COATINGS

PRIORITY CLAIM

This application claims priority to U.S. Provisional Patent Application Ser. No. 61/543,126 filed Oct. 4, 2011, incorporated by reference herein in its entirety

STATEMENT OF GOVERNMENT INTEREST

The invention described herein was made in part with government support under grant number CTS-0827681 awarded by the National Science Foundation (NSF); and grant number W911NF-08-1-0331, awarded by the Army Research Office (ARO). The United States Government has certain rights in the invention.

FIELD OF THE INVENTION

The present disclosure concerns the various nanowires, and quantum dots, sheets, and ribbons, methods for making the same, and their applications in bioimaging and photonic device applications.

BACKGROUND OF THE INVENTION

Nanowires

Semiconductor nanowires (NWs) with ultrathin diameter below the exciton Bohr radius, especially those with magic-size (i.e., less than 2 nm) diameter, have attracted significant interest in the past few years because of their predicted unique quantum confinement effects, quantum conductance, ballistic conduction, low thermal conductivity, increased surface area properties, and potential applications in thermoelectric devices, sensors, catalysts, and other nanodevices. Spherical magic-size semiconductor clusters (or ultra-small nanocrystals) with a well-defined number of atoms have been extensively prepared by various techniques, however, ultrathin semiconductor NWs with magic-size diameter have been difficult to achieve.

Zinc sulfide (ZnS), an important semiconductor material with a direct band gap of 3.6 eV at room temperature and a large exciton binding energy of 40 meV, is widely used in lasers, electroluminescent devices, flat panel displays, field emitters, infrared windows, and UV-light detectors. To the best of our knowledge, there has been no report describing high quality ZnS NWs with diameters below 2 nm.

Doping can enhance the properties of semiconductors by providing a powerful method to control their significant optical, electronic, transport, and spintronic properties. Mn-doped zinc chalcogenide quantum dots (QDs) have been explored as alternatives to CdSe QDs. Methods for the synthesis of high-quality Mn-doped ZnS QDs, characterized by sharp exciton absorption peaks, finely tunable and uniform diameters, tunable doping levels, and high quantum yields are still needed.

Quantum Dots

There are currently two grand challenges in the field of colloidal quantum dots (QDs, or semiconductor nanocrystals) based nanotechnology: one is to achieve robust non-blinking QDs and the other is to assemble different QDs of unique optical properties into hierarchically organized nanoarchitectures with control at single particle levels.

Nevertheless, there are still some challenges: 1) in synthesizing non-blinking or less blinking QDs of tunable multi-color emissions from blue to near infrared spectral range; 2) to achieve water-soluble nonblinking or less blinking QDs to conjugate with biomolecules, so they can be widely used for biological imaging applications; 3) more fundamental understanding and characterization of the non-blinking behavior are needed which requires synthesis of non-blinking QDs of different composition and optical properties; 4) efforts are greatly needed to achieve hierarchical assembly of these QDs into addressable architectures so it could provide a solid platform for systematic understanding of QD-QD interactions (e.g. Fluorescent Energy Transfer between QDs) and fabrication of QD based nanodevices for applications in biosensing and imaging.

Quantum Sheets and Ribbons

Tin sulfide (SnS) is an important main-group IV-VI (IV=Ge, Sn, Pb; VI=S, Se, Te) compound received significant attention recently due to its narrow band gap and rich electronic and optical properties. SnS is also known as inexpensive, naturally abundant, environmentally-benign, and heavy-metal-free (i.e., free from Cd, Pb, and Hg). Theoretical calculations indicate that SnS possesses all the qualities required for efficient absorption of solar energy, suitable for incorporation into clean energy conversion cells. Its other useful properties, e.g., photoconducting, photocatalytic and Peltier effect, make them promising candidates for diverse applications such as thermoelectric cooling, thermoelectric power generation, and near-infrared photo-electronics. All of the above applications would greatly benefit from the availability of the synthesis of SnS nanostructures with well-defined crystalline, sizes, and shapes in large quantities. However, synthesis of high quality SnS nanostructures is still a great challenges, relative to what has been achieved for both PbS and PbSe.

SUMMARY OF THE INVENTION

Herein, we report a simple, fast, green, and catalyst-free colloidal method for the synthesis of single-crystal ZnS NWs and high-quality wurtzite-type doped ZnS nanowires (e.g., Mn-doped ZnS nanowires) with diameter down to, for example, 1.2 nm, which is well below the exciton Bohr radius of ZnS (2.5 nm). Unusual properties related to the unique nature of the ultrathin ZnS NWs, such as large blue-shifted UV/Vis exciton absorption spectra, surface defect state dominant photoluminescence emission spectra, and geometry-related XRD pattern, were observed. Notably, the green and air-stable salt zinc nitrate can be used as the zinc source for the ZnS NWs synthesis. This precursor is chemically more stable than the toxic and flammable diethylzinc used in previous studies.

For example the high-quality wurtzite-type Mn-doped ZnS QRs can be prepared having diameters that are finely tunable from, for example, 1.6 to 5.6 nm, and variable Mn doping levels ranging from 0.18% to 1.6%. To our knowledge, this is the first example of colloidal synthesis of high-quality Mn-doped ZnS QRs with sharp exciton absorption peaks, finely tunable and uniform diameters, and high quantum yields up to 45%. In addition, our Mn-doped ZnS QRs demonstrate tunable dual-color (orange and blue) emissions and bright multiphoton (two- and three-photon) excitation luminescence, which may create new opportunities for photonic device and bioimaging applications.

We also show a colloidal synthesis of single crystalline IV-VI SnS nanoribbons formed via a unique metastable-to-stable phase transition process. We observed the unambiguous phase transitions from zinc-blende phase SnS nanospheres, to dual phase intermediate SnS heterostructures with nanosphere-heads and nanoribbon-tails, and to pure orthorhombic phase single crystalline SnS nanoribbons. Furthermore, we can use a simple inorganic HS– ligand to replace the original organic oleylamine ligand to improve the performance of the single nanoribbon based field effect transistors (FET). Finally, taking the advantages of the synthesis of desirable quality and quantity of one-dimensional SnS nanoribbon, we fabricated the first single SnS nanoribbon optoelectronic devices, which show p-type behavior with improved hole mobilities from 0.25 to 1.11 $cm^2V^{-1}s^{-1}$ after ligands exchange, as well as highly sensitive photocurrent response under small powder green laser illumination.

Accordingly, in one aspect, the disclosure provides nanocrystals comprising, (i) a core comprising a $Zn_xCd_{1-x}S_ySe_{1-y}$ alloy, wherein x and y are each independently greater than 0 and less than 1; and (ii) a coating, substantially covering the surface of the core, comprising a $ZnS_zSe_{1-z}$ alloy, wherein z greater than or equal to 0 and less than or equal to 1.

In another aspect, the disclosure provides nanocrystals comprising, (i) a core comprising CdTe; (ii) a first coating, substantially covering the surface of the core, comprising CdS; and (iii) an optional second coating, substantially covering the surface of the first coating, comprising ZnS, wherein the nanocrystal has a photoluminescence maximum between about 650 nm and 900 nm.

In another aspect, the disclosure provides methods for labeling an analyte comprising contacting a solution comprising the analyte with a nanocrystal comprising (i) a core comprising a $Zn_xCd_{1-x}S_ySe_{1-y}$ alloy, wherein x and y are each independently greater than 0 and less than 1; and (ii) a coating, substantially covering the surface of the core, comprising a $ZnS_zSe_{1-z}$ alloy, wherein z greater than or equal to 0 and less than or equal to 1, wherein the nanocrystal is chemically conjugated to a binding moiety which can bind directly or indirectly to the analyte.

In another aspect, the disclosure provides methods for labeling an analyte comprising contacting a solution comprising the analyte with a nanocrystal comprising (i) a core comprising CdTe; (ii) a first coating, substantially covering the surface of the core, comprising CdS; and (iii) an optional second coating, substantially covering the surface of the first coating, comprising ZnS, wherein the nanocrystal has a photoluminescence maximum between about 500 nm and 900 nm; and wherein the nanocrystal is chemically conjugated to a moiety which can bind directly or indirectly to the analyte.

In another aspect, the disclosure provides nanowire of the formula Zn(S,Se,Te) having a diameter between about 1 nm and 10 nm, wherein the nanowire is optionally doped with one or more metal selected from the group consisting of Fe, Co, Ni, Mn, Au, Ag, and Cu.

In another aspect, the disclosure provides methods for preparing optionally doped Zn(S,Se,Te) nanowires comprising contacting a first solution comprising a S, Se, and/or Te precursor with a second solution comprising (a) a zinc precursor, (b) an $C_{1-30}$alkylamine and/or $C_{2-30}$alkenylamine, (c) an $C_{1-30}$alkylthiol, and (d) an optional doping metal precursor, to form a third solution under conditions suitable for formation of Zn(S,Se,Te) nanowires.

In another aspect, the disclosure provides dispersions comprising the nanowires of any of the preceding aspects and a solvent.

In another aspect, the disclosure provides SnS quantum sheets or ribbons having a thickness of about 2 nm to about 10 nm.

In another aspect, the disclosure provides field effect transistors (FETs) comprising a SnS quantum sheet of the preceding aspect.

In another aspect, the disclosure provides methods for preparing SnS quantum sheets or ribbons comprising contacting a first solution comprising a S precursor with a second solution comprising (a) a tin precursor, (b) an $C_{1-30}$alkylamine and/or $C_{2-30}$alkenylamine, and (c) hexamethyldisilazane, to form a third solution under conditions suitable for formation of SnS quantum sheets or ribbons.

DETAILED DESCRIPTION OF THE INVENTION

Quaternary Core-Shell Non-Blinking Nanocrystals

Figure 1:
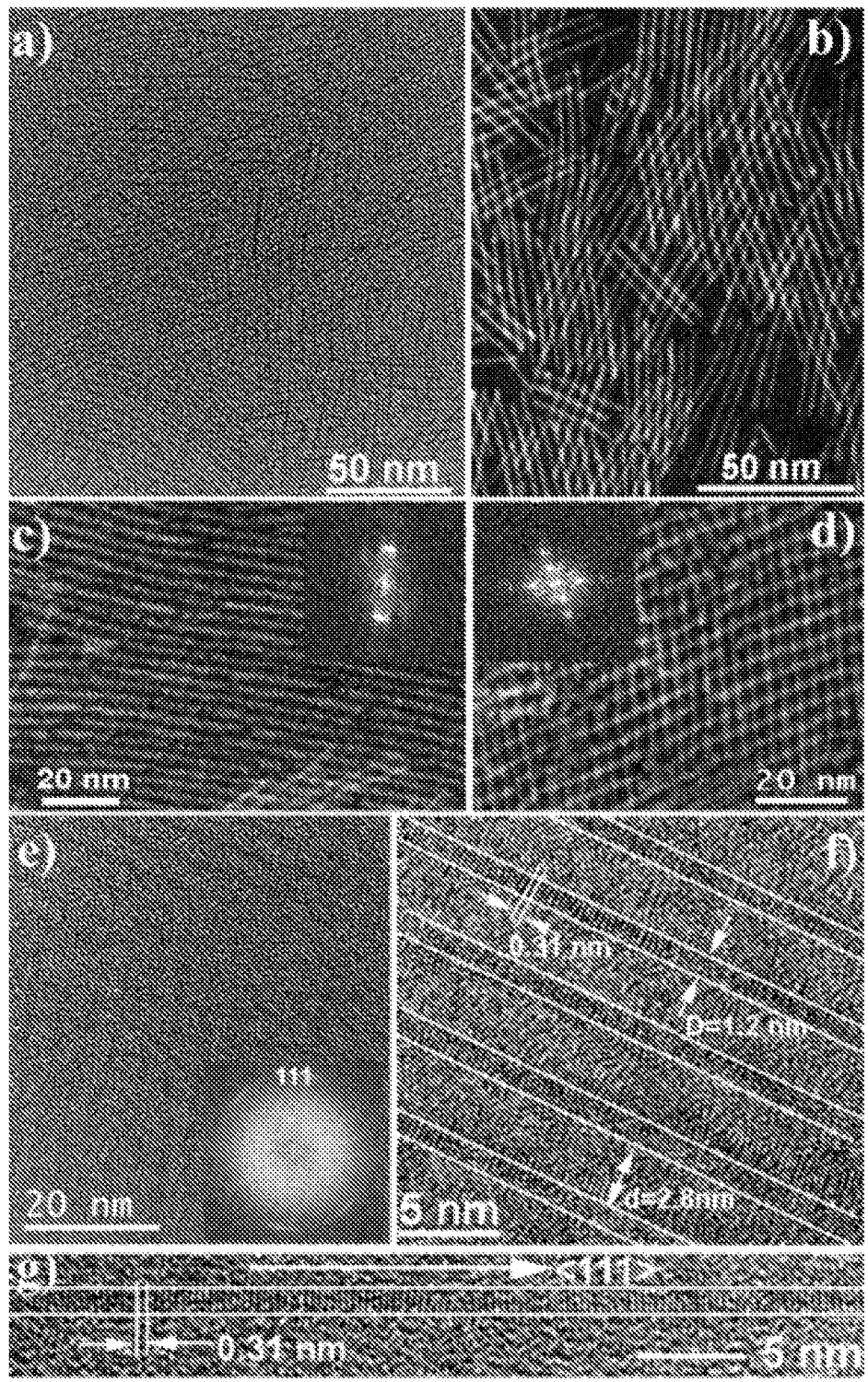
FIG. 1. a) TEM image of the magic-size ZnS nanowires. b-d) HAADF-STEM images of NWs; insets in (c,d) are their corresponding fast Fourier transform (FFT) images, showing the formation of superlattice structures. e-g) HRTEM images of NWs; inset in (e) shows the corresponding FFT image of (e); the white lines in (fig) label the boundary of individual NWs, showing the formation of single crystal NWs with diameter of 1.2 nm.

ZnCdSSe alloyed quantum dots can be over-coated by a layer of $ZnS_zSe_{1-z}$ shell to improve its photoluminescence quality. Without being limited to anyone theory of operation, deposition of a new $ZnS_zSe_{1-z}$ shell (including but not limited to a ZnS shell) on the surface of ZnCdSSe alloyed QDs may greatly eliminate surface defects, thereby reducing the possibility of non-radiative transition, leading to further increased luminescent efficiency, improved photostability and reduced blinking. In addition, for bio-application, the capping $ZnS_zSe_{1-z}$ shell can form a core/shell structure with ZnCdSSe alloyed QD cores inside and $ZnS_zSe_{1-z}$ shells outside to reduce the toxicity of cadmium. This design can provide a series of non-blinking QDs with photoluminescence emission tunable across the whole visible range. Such alloyed QDs are easy to synthesize and have high photoluminescence quantum yield. We believe these alloyed QDs could find broad use in multicolor bio-imaging, bio-sensing, light-emitting diodes, solar cells, and other nanodevice applications.

In this aspect, the disclosure provides nanocrystals comprising, (i) a core comprising a $Zn_xCd_{1-x}S_ySe_{1-y}$ alloy, wherein x and y are each independently greater than 0 and less than 1; and (ii) a coating, substantially covering the surface of the core, comprising a $ZnS_zSe_{1-z}$ alloy, wherein z greater than or equal to 0 and less than or equal to 1.

The nanocrystal core can have a diameter between about 1.0 nm and 20 nm. For example, in certain embodiments, the core can have a diameter between about 1.0 nm and 15 nm; or between 1.0 nm and 10 nm; or between 1.0 nm and 9.0 nm; or between 1.0 nm and 8.0 nm; or between 1.0 nm and 7.0 nm; or between 1.0 nm and 6.0 nm; or between 1.0 and 5.0 nm.

The coating can have a thickness between about 0.3 nm and 10 nm. For example, in certain embodiments, the coating can have a thickness between about 0.3 nm and 9.0 nm; or between about 0.3 nm and 8.0 nm; or between about 0.3 nm and 7.0 nm; or between about 0.3 nm and 6.0 nm; or between about 0.3 nm and 5.0 nm; or between about 0.3 nm and 4.0 nm; or between about 0.3 nm and 3.0 nm; or between about 0.3 nm and 2.0 nm; or between about 0.3 nm and 1.0 nm. In other embodiments, the thickness of the coating can be 0.3 nm; or 0.5 nm; or 1.0 nm; or 2.0 nm; or 3.0 nm; or 4.0 nm; or 5.0 nm; or 6.0 nm; or 7.0 nm; or 8.0 nm; or 9.0 nm; or 10 nm.

Overall, the diameter of the core and the thickness of the coating can provide a nanocrystal having a diameter between about 1.6 nm and 40 nm. For example, in certain embodiments, the nanocrystal can have a diameter between 1.6 nm and 30 nm; or between 1.6 nm and 25 nm; or between 1.6 nm and 20 nm; or between 1.6 nm and 10 nm; or between 2.0 nm and 40 nm; or between 5.0 nm and 40 nm; or between 10 nm and 40 nm; or between 20 nm and 40 nm.

The nanocrystal can further comprise a monolayer formed over the surface of the nanocrystal, wherein the monolayer comprises molecules of the formula, X—Y—Z, wherein X is a functional group capable of reacting with or coordinating with the surface of the nanocrystal; Y is a divalent linking group; and Z is a functional molecule. For example, in certain embodiments, X can be —COOH or a thiol. In other embodiments, X is a thiol. Z can be one half of a specific binding pair. For example, Z can be a nucleic acid, avidin, streptavidin, biotin, a protein, an enzyme antagonist, agonist, partial agonist, or partial antagonist, or an antigen. Y may be any divalent linking group suitable for a given purpose.

In other embodiments, the core can comprise $Zn_{0.6}Cd_{0.4}S_{0.5}Se_{0.5}$, $Zn_{0.90}Cd_{0.10}S_{0.89}Se_{0.11}$, $Zn_{0.80}Cd_{0.20}S_{0.71}Se_{0.29}$, $Zn_{0.69}Cd_{0.31}S_{0.59}Se_{0.41}$, $Zn_{0.41}Cd_{0.59}S_{0.40}Se_{0.6}$, $Zn_{0.25}Cd_{0.75}S_{0.24}Se_{0.76}$, or $Zn_{0.11}Cd_{0.89}S_{0.10}Se_{0.90}$. In another embodiment, the core can comprise $Zn_{0.11-0.90}Cd_{0.10-0.89}S_{0.10-0.89}Se_{0.11-0.9}$, wherein $x+(1-x)+y+(1-y)=1$. In yet other embodiments, the core can comprise $Zn_{0.6}Cd_{0.4}S_{0.5}Se_{0.5}$.

In another embodiment of any of the preceding embodiments, the coating comprises ZnS. In another embodiment, of any of the preceding embodiments, the coating comprises ZnSe.

In another embodiment of any of the preceding embodiments, the nanocrystal has a photoluminescence maximum between about 400 nm and 700 nm. For example, the nanocrystal has a photoluminescence maximum between about 450 nm and 700 nm; or between about 500 nm and 700 nm; or between about 550 nm and 700 nm; or between about 600 nm and 700 nm; or between about 650 nm and 700 nm; or between about 400 nm and 650 nm; or between about 400 nm and 600 nm; or between about 400 nm and 550 nm; or between about 400 nm and 500 nm; or between about 400 nm and 450 nm.

In another embodiment of any of the preceding embodiments, the nanocrystal is non-blinking. In another embodiment of any of the preceding embodiments, the core of the nanocrystal is chemically uniform.

CdTe Core Multi-Shell QDs for Non-Blinking or Less-Blinking QDs

The ZnS shell can be extended toward different materials to form multi-layered core/shell/shell QDs. We propose to introduce a thin layer of a semiconductor between the emitting core and the wide band gap shell, with the lattice spacing intermediate to that of the core and the shell, for example, multi-shell CdTe/CdS/ZnS QDs. The multi-shell structure allows a stepwise change of lattice spacing from the emitting core and the protecting ZnS shell. This design could allow for considerable reduction of the strain-induced defects inside QDs, thus may considerably reduce the blinking of the QDs. In addition, for CdTe/CdSe/CdS/ZnS multi-shell QDs, charge carriers can be segregated in the core and shell, and the radiative recombination occurs across the material interface, thus lead to formation of type II QDs. The emission of type-II multishell QD can be tailored by the shell thickness as well as the core size, which could span from visible to near-infrared range.

Optical studies of the core/shell/shell QDs of the disclosure have found a red-shift has been observed for the core/shell/shell QDs compared to core QDs and core/shell QDs, which is an indication for the formation of the intended CdTe/CdS/ZnS core/shell/shell structure rather than a $Cd_xZn_{1-x}Te_yS_{1-y}$ alloy. The formation of alloyed QDs would lead to a blue shift in both UV-Vis absorption and photoluminescence spectrum because of the larger band-gap energy of alloyed QDs. Additionally, the photoluminescence intensity of as-prepared QDs was superior to that of corresponding CdTe/CdS QDs, since the ZnS shell effectively reduced the number of defects on the surface of the QDs. As a result, highly luminescent (PLQY 50-80%) CdTe/CdS/ZnS core/shell/shell QDs were prepared using aqueous methods. Powder XRD (p-XRD) patterns of the CdTe cores, CdTe/CdS core/shell, and CdTe/CdS/ZnS core/shell/shell QDs are presented in FIG. 10d. The CdTe XRD pattern consists of the characteristic peaks of the zinc blende CdTe. When the CdS and ZnS shell is overgrown onto the cubic CdTe template, the general pattern of the cubic lattice is maintained in the core/shell and core/shell/shell structures, but the diffraction peaks shift to larger angles consistent with the smaller lattice constants for CdS and ZnS compared with that of CdTe.

Type II CdTe/CdSe/CdS/ZnS core/shell/shell/shell QDs may be prepared from the methods herein. A type-II QD, has both the valence and conduction bands in the core lower (or higher) than in the shell. As a result, one carrier is mostly confined to the core, while the other is mostly confined to the shell. Type-II QDs are expected to have many novel properties that are fundamentally different from the type-I QDs because of the spatial separations of carriers. Type-II structures can allow access to wavelengths that would otherwise not be available with a single material. The emission of the type-II multi-shell QD can be tailored by the shell thickness as well as the core size, which could span from visible to near-infrared range. In addition, the separation of charges in the lowest excited states of type-II QDs should make these materials more suitable in photovoltaic or photoconduction applications, where the QDs are the chromophores and one of the photocarriers is injected from the QD into a matrix before recombination can occur. In particular, multi-shell QDs with near-infrared emission have great potential for biomedical imaging.

Figure 27:
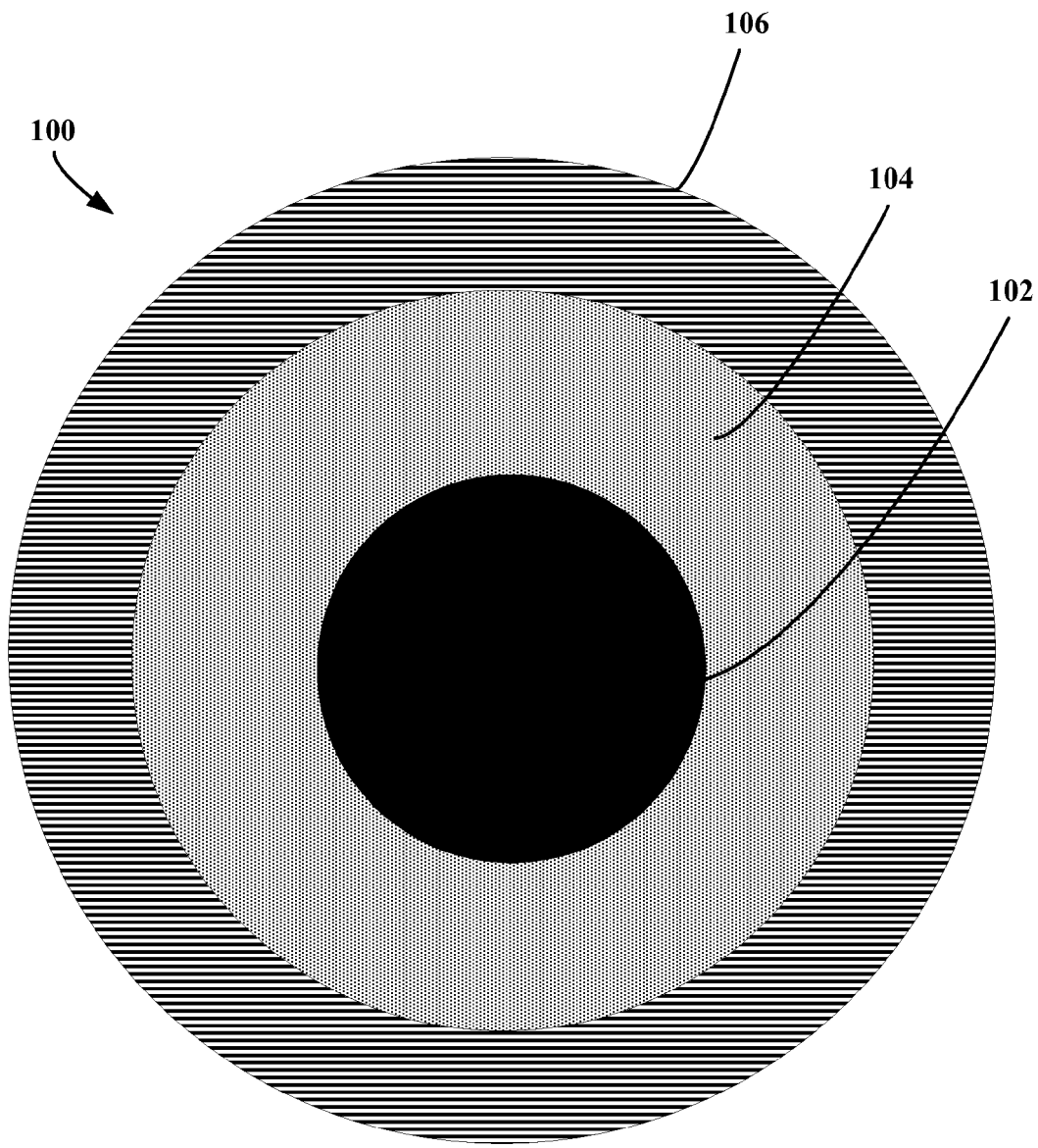
FIG. 27 illustrates an example nanocrystal comprising (i) a core comprising CdTe, (ii) a first coating, substantially covering the surface of the core, comprising CdS, and (iii) a second coating, substantially covering the surface of the first coating, comprising ZnS.

In another aspect, as illustrated in FIG. 27, the disclosure provides nanocrystal 100 comprising, a core 102 comprising CdTe; a first coating 104, substantially covering the surface of the core 102, comprising CdS; and a second coating 106, substantially covering the surface of the first coating 104, comprising ZnS, wherein the nanocrystal 100 has a photoluminescence maximum between about 650 nm and 900 nm. In a further embodiment, the nanocrystal 100 further comprises a third coating (not shown) comprising CdSe substantially covering the surface of the core 102 and located between the core 102 and the CdS coating 104.

The nanocrystal core can have a diameter between about 1.0 nm and 20 nm. For example, in certain embodiments, the core can have a diameter between about 1.0 nm and 15 nm; or between 1.0 nm and 10 nm; or between 1.0 nm and 9.0 nm; or between 1.0 nm and 8.0 nm; or between 1.0 nm and 7.0 nm; or between 1.0 nm and 6.0 nm; or between 1.0 and 5.0 nm.

The first coating and the optional third coating can have a thickness between about 1 nm and 10 nm. For example, in certain embodiments, the first coating and/or the optional third coating can have a thickness between about 0.3 nm and 9.0 nm; or between about 1.0 nm and 8.0 nm; or between about 1.0 nm and 7.0 nm; or between about 1.0 nm and 6.0 nm; or between about 1.0 nm and 5.0 nm; or between about 1.0 nm and 4.0 nm; or between about 1.0 nm and 3.0 nm; or between about 1.0 nm and 2.0 nm. In other embodiments, the thickness of the first coating and/or the optional third coating can be 1.0 nm; or 2.0 nm; or 3.0 nm; or 4.0 nm; or 5.0 nm; or 6.0 nm; or 7.0 nm; or 8.0 nm; or 9.0 nm; or 10 nm.

The second coating can have a thickness between about 0.3 and 10 nm. For example, in certain embodiments, the second coating can have a thickness between about 0.3 nm and 9.0 nm; or between about 0.3 nm and 8.0 nm; or between about 0.3 nm and 7.0 nm; or between about 0.3 nm and 6.0 nm; or between about 0.3 nm and 5.0 nm; or between about 0.3 nm and 4.0 nm; or between about 0.3 nm and 3.0 nm; or between about 0.3 nm and 2.0 nm; or between about 0.3 nm and 1.0 nm. In other embodiments, the thickness of the second coating can be 0.3 nm; or 0.5 nm; or 1.0 nm; or 2.0 nm; or 3.0 nm; or 4.0 nm; or 5.0 nm; or 6.0 nm; or 7.0 nm; or 8.0 nm; or 9.0 nm; or 10 nm.

Overall, the diameter of the core and the thickness of the coating can provide a nanocrystal having a diameter between about 1.6 nm and 40 nm. For example, in certain embodiments, the nanocrystal can have a diameter between 1.6 nm and 30 nm; or between 1.6 nm and 25 nm; or between 1.6 nm and 20 nm; or between 1.6 nm and 10 nm; or between 2.0 nm and 40 nm; or between 5.0 nm and 40 nm; or between 10 nm and 40 nm; or between 20 nm and 40 nm.

The nanocrystal can further comprise a monolayer formed over the surface of the nanocrystal, wherein the monolayer comprises molecules of the formula, X—Y—Z, wherein X is a functional group capable of reacting with or coordinating with the surface of the nanocrystal; Y is a divalent linking group; and Z is a functional molecule. For example, in certain embodiments, X can be —COOH or a thiol. In other embodiments, X is a thiol. Z can be one half of a specific binding pair. For example, Z can be a nucleic acid, avidin, streptavidin, biotin, a protein, an enzyme antagonist, agonist, partial agonist, or partial antagonist, or an antigen.

In another embodiment of any of the preceding embodiments, the nanocrystal is non-blinking.

Nanocrystal Organization

Organizing nanoparticles into rationally designed ensemble structures is of great scientific interest because architecturally defined collective properties from multiple nanoparticles (NPs) could lead to applications such as photonic antennas and controlled energy transfer. Recently, structural DNA nanotechnology has opened up new perspectives for the directed self-assembly of NPs and other molecular species into patterned nanostructures by taking advantage of the progress in the design and construction of artificial nanostructures with complex geometry or patterns through DNA self-assembly. Among these new techniques, the success of using DNA-origami nanostructures to organize NPs has been limited to only metallic gold NPs. To our knowledge, there has been no report demonstrating DNA-origami-directed self-assembly of QDs into rationally designed discrete architectures; this may, in part, be due to the significantly different surface properties of QDs and gold nanoparticles. The difficulty of making QDs compatible with the conditions used in DNA nanostructure self-assembly (DNA tile self-assembly commonly need high cationic concentration, e.g. 10 mM $Mg^{2+}$ which will cause aggregation of QDs) has prohibited many interesting studies of multi-component nanoparticle photonic systems, for example, distance-dependent plasmonic quenching or enhancement between metallic nanoparticles and QDs. Assembling DNA nanostructures provides unprecedented opportunities to have true control of spatial arrangement of QDs in 2- and 3-dimensions. The complexity achieved at the molecular level mimics what has existed in nature and far exceeds the current capabilities using top-down lithographic approach.

DNA nanostructures can be prepared to assemble with a variety of desired shapes and patterns (see Rothemund, Nature 2006, 440, 297-302; Ke et al, J. Am. Chem. Soc. 2009, 131, 15903; Dietz et al, Science 2009, 325, 725; and Douglas et al, Nature 2009, 459, 414, each of which is hereby incorporated by reference in its entirety). The fabrication of DNA nanostructures begins with the self-assembly of single stranded DNA into small building block materials called tiles. DNA tiles bearing complementary sticky ends are then able to further self-assemble into larger arrays with distinct topological and geometric features. In one embodiment referred to as DNA origami, in which a large single stranded nucleic acid sequence (including but not limited to a viral genome, such as M13 of 7429 bases long) can be used to nucleate the self-assembly of more than 200 small synthetic DNA oligos (termed as "staple strands" or "helper strands"), which will fold the long ssDNA into a variety of predetermined nano-patterns, such as circle, squares, triangles, or smiley faces.

Self-assembled DNA nanostructures and nanoarrays provide excellent scaffolds to organize other functional molecules into nano-architectures with precisely controlled spatial resolution. DNA origami nanostructures have been use to template the self-assembly of metallic nanoparticles into rationally defined patterns (see Sharma et al., Angew. Chem. Int. Ed. 2006, 45, 730; Sharma et al., J. Am. Chem. Soc. 2008, 130, 7820; and Sharma et al, Science 2009, 323, 112, each of which is hereby incorporated by reference in its entirety)

Thus, any of the nanocrystals (NC) described herein can be first conjugated with, for example, unique sequence single-stranded DNA oligos (50-150 nt long), through, for example thiol-linkage. The DNA-NC conjugate with a 1:1 ratio can be separated from other NCs conjugated with more than one DNA strand (ratios of 1:2, 1:3 and so on) as well as the bare NC by agarose gel electrophoresis. The 1:1 conjugates can be extracted from the gel, and used in the next step of DNA self-assembly. The DNA oligo on the surface of the NC will tie-in to the DNA scaffold at a unique position dictated by Watson-Crick base-pairing to the other DNA strands in the DNA scaffold. NCs can be placed at any desired locations on the self-assembled DNA Origami arrays.

Optionally-Doped ZnS Nanowires

In another aspect, the disclosure provides nanowires of the formula Zn(S,Se,Te) having a diameter between about 1 nm and 10 nm, wherein the nanowire is optionally doped with one or metal selected from the group consisting of Fe, Co, Ni, Mn, Au, Ag, and Cu. In certain embodiments, the nanowires have a diameter between about 1.0 nm and 9.0 nm; or between 1.0 nm and 8.0 nm; or between 1.0 nm and 7.0 nm; or between 1.0 nm and 6.0 nm; or between 1.0 and 5.0 nm; or between about 1.0 nm and 4.0 nm; or between about 1.0 nm and 3.0 nm; or between about 1.0 nm and 2.0 nm. In other embodiments, the nanowires have a diameter of about 1.0 nm; or 2.0 nm; or 3.0 nm; or 4.0 nm; or 5.0 nm.

Herein, a notation is used to refer to alloys having the form of an element and a set of elements within a set of parenthesis; for example, Zn(EFG). This notation means that the alloy comprises Zn and at least one element selected from E, F, and G. For example, Zn(SSeTe) alloy includes ZnS, ZnSe, ZnTe, and ZnSSe, among other combinations.

In other embodiments, the nanowires are single-crystalline.

The nanowires can have a length between about 5 nm and about 250 nm. For example, the nanowires can have a length between about 10 nm and 250 nm; or between 50 nm and 250 nm; or 100 nm and 250 nm; or 5 nm and 200 nm; or 5 nm and 150 nm; or 5 nm and 100 nm; or 5 nm and 50 nm.

When the nanowires are doped with one or more metal selected from Fe, Co, Ni, Mn, Au, Ag, and Cu, the nanowires can comprise about 0.1 mol % to about 2.0 mol % of the dopant. In certain embodiments, the nanowires can comprise about 0.1 mol % to about 2.0 mol % manganese. In certain embodiments, the nanowires can comprise about 0.1 mol % to about 2.0 mol % iron. In certain embodiments, the nanowires can comprise about 0.1 mol % to about 2.0 mol % cobalt. In certain embodiments, the nanowires can comprise about 0.1 mol % to about 2.0 mol % nickel. In certain embodiments, the nanowires can comprise about 0.1 mol % to about 2.0 mol % gold. In certain embodiments, the nanowires can comprise about 0.1 mol % to about 2.0 mol % s silver. In certain embodiments, the nanowires can comprise about 0.1 mol % to about 2.0 mol % copper.

The nanowire in any of the preceding embodiments can have an absorption maximum between about 400 nm and 700 nm. For example, the nanowires in any of the preceding embodiments can have an absorption maximum between about 450 nm and 700 nm; or between about 500 nm and 700 nm; between about 550 nm and 700 nm; or between about 600 nm and 700 nm; or between about 450 nm and 650 nm; or between about 450 nm and 600 nm; or between about 450 nm and 550 nm.

The nanowires can further comprise a monolayer formed over the surface of the nanowire, wherein the monolayer comprises molecules of the formula, X—Y—Z, wherein X is a functional group capable of reacting with or coordinating with the surface of the nanowire; Y is a divalent linking group; and Z is a functional molecule. For example, in certain embodiments, X can be —COOH or a thiol. In other embodiments, X is a thiol. Z can be one half of a specific binding pair. For example, Z can be a nucleic acid, avidin, streptavidin, biotin, a protein, an enzyme antagonist, agonist, partial agonist, or partial antagonist, or an antigen.

The preceding nanowires can be prepared according to methods comprising contacting a first solution comprising a S, Se, and/or Te precursor with a second solution comprising (a) a zinc precursor, (b) an $C_{1-30}$alkylamine (e.g., n-decylamine, n-octylamine, n-nonylamine, n-dodecylamine) and/or $C_{2-30}$alkenylamine (e.g., oleylamine), (c) an $C_{1-30}$ alkylthiol (e.g., n-decanethiol, n-octanethiol, n-nonanethiol, n-dodecanethiol), and (d) an optional doping metal precursor, to form a third solution under conditions suitable for formation of Zn(S,Se,Te) nanowires.

The third solution can be heated at a temperature between about 200° C. and 250° C., or 200° C. and 300° C. for a period of time suitable for formation of the Zn(S,Se,Te) nanowires. For example, the solution can be heated for about 5 minutes to about 30 minutes; or about 5 minutes to about 20 minutes; or about 5 minutes to about 15 minutes.

The method can further comprise adding an alcohol to the third solution. The alcohol can be any which is compatible with the reaction conditions. Suitable examples include, but are not limited to methanol, ethanol, isopropanol, and mixtures thereof. In certain embodiments, the alcohol comprises a mixture of methanol, ethanol, and isopropanol. After addition of the alcohol, the unreacted starting material can be removed, for example, by centrifugation.

In any of the preceding embodiments, the zinc precursor is zinc(II)nitrate, zinc(II)sulfate, zinc(II) acetate, or a zinc(II) halide, or a mixture thereof. In one embodiment, the zinc precursor is zinc(II)nitrate. In one embodiment, zinc precursor is zinc(II)sulfate. In one embodiment, zinc precursor is zinc(II) acetate. In one embodiment, zinc precursor is a zinc (II) halide (e.g., zinc(II)chloride, zinc(II)bromide, or zinc(II) iodide).

When the nanowires are doped, the doping metal precursor can comprise a Fe, Co, Ni, Mn, Au, Ag, or Cu salt, or a mixture thereof. Suitable salts include, but are not limited to nitrate, acetate, sulfate, and halide salts (e.g., a chloride, bromide, or iodide salt). In one particular example, the doping metal precursor is manganese(II)nitrate.

In another embodiment, the first solution comprises a S, Se, and/or Te precursor and $C_{1-30}$alkylamine (e.g., n-decylamine, n-octylamine, n-nonylamine, n-dodecylamine) and/or $C_{2-30}$alkenylamine (e.g., oleylamine). In another embodiment, the first solution comprises sulfur and $C_{1-30}$alkylamine (e.g., n-decylamine, n-octylamine, n-nonylamine, n-dodecylamine) and/or $C_{2-30}$alkenylamine (e.g., oleylamine). In another embodiment, the first solution comprises selenium and $C_{1-30}$alkylamine (e.g., n-decylamine, n-octylamine, n-nonylamine, n-dodecylamine) and/or $C_{2-30}$alkenylamine (e.g., oleylamine). In another embodiment, the first solution comprises tellurium and $C_{1-30}$alkylamine (e.g., n-decylamine, n-octylamine, n-nonylamine, n-dodecylamine) and/or $C_{2-30}$alkenylamine (e.g., oleylamine). In another embodiment, the first solution comprises sulfur and oleylamine. In another embodiment, wherein the first solution comprises selenium and oleylamine. In another embodiment, the first solution comprises tellurium and oleylamine In another embodiment, the second solution comprises the zinc precursor and doping metal precursor in a molar ratio of between about 100:1 and about 3:1. For example, the zinc precursor and doping metal precursor can be present in a molar ratio of between about 50:1 and about 3:1; or about 40:1 and about 3:1; or about 20:1 and about 3:1; or about 10:1 and 3:1; or about 100:1 and 10:1; or about 100:1 and 20:1; or about 100:1 and 30:1; or about 100:1 and 40:1; or about 100:1 and 50:1. In other embodiments, the In another aspect, the disclosure provides dispersions comprising the nanowires of any one the preceding embodiments and a solvent. For example, the solvent can include an alkane (e.g., hexane, octane, decane, dodecane, and mixtures thereof).

Methods for Labeling an Analyte

The nanocrystals described above can be used in methods for labeling an analyte in vivo or in vitro.

For example, the method can comprise contacting a solution comprising the analyte with a nanocrystal comprising (i) a core comprising a $Zn_xCd_{1-x}S_ySe_{1-y}$ alloy, wherein x and y are each independently greater than 0 and less than 1; and (ii) a coating, substantially covering the surface of the core, comprising a $ZnS_zSe_{1-z}$ alloy, wherein z greater than or equal to 0 and less than or equal to 1, wherein the nanocrystal is chemically conjugated to a binding moiety which can bind directly or indirectly to the analyte.

In another example, the method can comprise contacting a solution comprising the analyte with a nanocrystal comprising (i) a core comprising CdTe; (ii) a first coating, substantially covering the surface of the core, comprising CdS; and (iii) an optional second coating, substantially covering the surface of the first coating, comprising ZnS, wherein the nanocrystal has a photoluminescence maximum between about 500 nm and 900 nm; and wherein the nanocrystal is chemically conjugated to a moiety which can bind directly or indirectly to the analyte.

In another example, the method can comprise contacting a solution comprising the analyte with a nanowire of the formula Zn(S,Se,Te) having a diameter between about 1 nm and 10 nm, wherein the nanowire is optionally doped with one or metal selected from the group consisting of Fe, Co, Ni, Mn, Au, Ag, and Cu, and wherein the nanowire is chemically conjugated to a moiety which can bind directly or indirectly to the analyte.

The nanowires and nanocrystals in the preceding methods can be according to any of the preceding aspects and embodiments thereof.

In certain embodiments, the analyte comprises a cell. In various other non-limiting embodiments, the analyte can be, for example, a nucleic acid, a protein, an enzyme antagonist, agonist, partial agonist, or partial antagonist, or an antigen. The term "nucleic acid" as used herein designates single or double stranded mRNA, RNA, cRNA and DNA, said DNA inclusive of cDNA and genomic DNA.

A "protein" refers to an amino acid polymer, comprising natural and/or non-natural amino acids, as are well understood in the art. An "antigen" refers to a molecular entity which is bound by an antibody.

In certain embodiments, the binding moiety is one half of a specific binding pair. The term "specific binding pair" as used herein refers to two compounds that specifically bind to one another in a non-covalent manner, such as but not limited to a receptor (e.g., enzyme) and a ligand; an antibody and an antigen; complementary nucleic acids; or an aptamer and its target. "Nucleic acids" may be any natural or synthetic nucleic acids, including DNA and RNA, and can be from 10 to 1,000 nucleotides in length. In certain embodiments, the nucleic acids are 10 to 100 nucleotides in length. In certain embodiments, the nucleic acids are 10 to 75 nucleotides in length; or 10 to 50 nucleotides; or 10 to 40 nucleotides in length. Shorter oligomers can be less costly but may not be robust; longer oligomers can be used for higher operating temperatures, or in harsher (e.g., pH or high salt concentration) environments.

For example, the specific binding pair can be complementary nucleic acids, such as two complementary single-stranded DNA molecules capable of forming duplex DNA, two complementary single-stranded RNA molecules capable of forming double-stranded RNA, or a single-stranded DNA molecule and a single-stranded RNA molecule capable of forming a DNA-RNA hybrid. It will be understood by one of skill in the art that the two individual nucleic acid molecules can form a binding pair complex under the appropriate hybridization or annealing conditions, and that such conditions can be optimized for the particular nucleic acid molecules at issue. It will be further understood by one of skill in the art that once formed, the duplex DNA, double-stranded RNA, or DNA-RNA hybrid can be disassociated under appropriate denaturation conditions. For example, formation or disassociation of the bound complex may be achieved through changes in temperature, pH, salt concentration, concentration of other chemicals, or a combination thereof. Furthermore, the complementary single-stranded nucleic acid molecules that form a specific binding pair do not need to be 100% matched, i.e. there may be mismatches in individual base pairs, with no specific limit on the number and position of mismatches, provided that the complementary single-stranded nucleic acid molecules will from a reversible binding pair under the appropriate conditions. It is well within the purview of one of skill in the art to assess the nature of the permissible mismatches, and the appropriate conditions for reversible binding. Thus, in certain embodiments where a first single-stranded nucleic acid molecule and a second single-stranded nucleic acid molecule are used as a specific binding pair in accordance with the invention, 1%, 2%, 3%, 4%, 5%, 10%, 15%, 20%, 25%, 30%, 35%, 40%, 45%, or 50% of the base pairs, for example, may be mismatched between the first and second single-stranded nucleic acid. Similarly, the number of mismatches may be within any range created by any two of previously recited percentages, for example 1-10%, 3-25%, 5-15%, etc.

Alternatively, the specific binding pair can be biotin and avidin or biotin and streptavidin, or analogs thereof (i.e. biotin or avidin/streptavidin molecules that have been modified but yet allow for reversible binding as described herein). In another example, the specific binding pair can be an antigen and an antibody. Suitable antigens include, but are not limited to, fluorescein, biotin, digoxigenin, or dinitrophenol. In a further example, the specific binding pair can also be an aptamer and its target molecule. Aptamers can be short nucleic acid or short peptides (e.g., 6-40 kDa) which strongly bind a target molecule, typically with binding constants ($K_D$) in the micromolar to nanomolar range (i.e., <1000 µM to <1000 nM). Aptamer targets can include, but are not limited to, an organic dye (e.g., fluorescein, Cy3, Cy5), a disaccharide (e.g., cellobiose, lactose, maltose, gentiobiose), an aminoglycoside (e.g., tobramycin, lividomycin, kanamycin A, kanamycin B, neomycin B), an antibiotic (e.g., viomycin and tetracyclin), dopamine, porphyrins (e.g., hematoporphyrin), and biotin.

In certain other embodiments, the analyte is a nucleic acid or a peptide. In certain other embodiments, the analyte is a nucleic acid. In certain other embodiments, the analyte is a peptide.

SnS Quantum Sheet or Ribbon

In another aspect, the disclosure provides SnS quantum sheets or ribbons having a thickness of about 2 nm to about 10 nm.

The term "quantum sheet" as used herein means a crystalline material having a plate or flake shape (i.e., the length and width of the plate or flake are in a ratio of about 1:1 to about 1:5, respectively) and a thickness less than about 20 nm, for example, between about 0.5 nm and about 20 nm.

The term "quantum ribbon" as used herein means a crystalline material having a ribbon shape (i.e., the length and width of the plate or flake are in a ratio greater than about 1:5, respectively), a lateral size of less than about 100 nm (e.g., about 1-10 nm), a thickness less than about 20 nm, for example, between about 0.5 nm and about 20 nm, and an unconstrained longitudinal size. For example, nanowires can have an aspect ratio of 10, or 100, or 1000, or more.

For example, the SnS quantum sheet or ribbon can have a thickness between about 2 nm and about 9 nm; or between about 2 nm and about 8 nm; or about 2 nm and about 7 nm; or about 2 nm and about 6 nm; or about 2 nm and about 5 nm; or about 2 nm and about 4 nm.

The SnS quantum sheets and ribbons can be prepared according to methods comprising contacting a first solution comprising a S precursor with a second solution comprising (a) a tin precursor, (b) an $C_{1-30}$alkylamine and/or $C_{2-30}$alkenylamine, and (c) hexamethyldisilazane, to form a third solution under conditions suitable for formation of SnS quantum sheets or ribbons.

The third solution can be heated at a temperature between about 200° C. and 400° C. for a period of time suitable for formation of the SnS quantum sheets or ribbons. For example, the third solution can be heated between about 225 and 400° C. The third solution can be heated for about 5 minutes to about 60 minutes.

The method can further comprise adding the third solution to an alcohol. The alcohol can be any which is compatible with the reaction conditions. Suitable examples include, but are not limited to methanol, ethanol, isopropanol, and mixtures thereof. In certain embodiments, the alcohol comprises a mixture of methanol, ethanol, and isopropanol. After addition of the alcohol, the unreacted starting material can be removed, for example, by centrifugation. In any of the preceding embodiments, the tin precursor can be a tin(II) halide, such as tin(IV)iodide.

The SnS quantum sheets and ribbons can be used in field effect transistors (FET). Such FETs can comprise a first electrode in contact with a first portion of the quantum sheet or ribbon, and a second electrode in contact with a second portion of the quantum sheet or ribbon. The first and second electrode can independently comprise Ti, Cr, Ni, Pd, Pt, Au, Ag, Al, Cu, or mixtures thereof. In one embodiment, each electrode comprises an adhesion layer comprising Cr or Ti, and a contact layer comprising Pt, Au, Ag, Al, or Cu. In certain other embodiments, each electrode comprises an adhesion layer comprising Cr and a contact layer Au. The quantum sheet can be disposed over a substrate. Examples of substrates include, but are not limited to, substrate comprising Si, such as Si(100) or a Si substrate having a $SiO_2$ surface coating layer.

Definitions

The term "nanowire" as used herein means structures that have a lateral size of less than about 100 nm (e.g., about 1-10 nm) and an unconstrained longitudinal size. For example, nanowires can have an aspect ratio of 10, or 100, or 1000, or more. In certain embodiments, the nanowires described herein are "quantum wires." The term "quantum wires", as used herein, refers to nanowires having a diameter of about 1 nm-10 nm. In certain embodiments, the quantum wires herein have diameters of about 1 nm-2 nm (comparable to their exciton Bohr radius).

The term "non-blinking" as used herein means that the referenced material displays an essentially continuous photoluminescence upon continuous photoexcitation according to methods familiar to those skilled in the art.

The term "single-crystalline" as used herein means the referenced crystal has a highly ordered crystalline structure and a continuously resolved lattice when analyzed by high-resolution TEM (HRTEM) according to methods familiar to those skilled in the art. For example, see the HRTEM methods described in Deng et al. J. Am. Chem. Soc. 2009, 131, 17774, which is hereby incorporated by reference in its entirety.

The term "functional molecule" as used herein means a chemical entity which is capable of labeling and/or binding with another molecule. Examples of functional molecules include, but are not limited to, members of specific binding pairs (as defined herein), monomers for preparation of polymers, natural and synthetic polymers, dichroic dyes, and photoluminescent (e.g., fluorescent or phosphorescent) dyes.

The term "chemically uniform" as used herein means that the referenced crystal essentially does not indicate any core-shell structure when analyzed by high-resolution TEM (HR-TEM) according to methods familiar to those skilled in the art. For example, see the HRTEM methods described in Deng et al. *J. Am. Chem. Soc.* 2009, 131, 17774, which is hereby incorporated by reference in its entirety.

Terms used herein may be preceded and/or followed by a single dash, "—", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl, arylalkyl-, and -alkylaryl indicate the same functionality.

Further, certain terms herein may be used as both monovalent and divalent linking radicals as would be familiar to those skilled in the art, and by their presentation linking between two other moieties. For example, an alkyl group can be both a monovalent radical or divalent radical; in the latter case, it would be apparent to one skilled in the art that an additional hydrogen atom is removed from a monovalent alkyl radical to provide a suitable divalent moiety.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, —$CH_2CH(CH_2CH_3)CH_2$—.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

"Cycloalkenyl" as used herein refers to a monocyclic or a bicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form $(CH_2)_w$—, where w is 1, 2, or 3). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia.

The term "halo" or "halogen" as used herein, means —Cl, —Br, —I or —F.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal, including, but not limited to mice, rats, other rodents, rabbits, dogs, cats, swine, cattle, sheep, horses, or primates, and most preferably humans.

The term "divalent linking group" as used herein means a chemical moiety capable of chemically attaching to both the X and Z groups herein. Examples of divalent linking groups include groups of the formula, —($C_0$-$C_{10}$ alkyl-Q)$_{0-1}$-$C_0$-$C_{10}$ alkyl-, wherein Q is a bond, aryl (e.g., phenyl), heteroaryl, $C_3$-$C_8$ cycloalkyl, or heterocyclyl; and no more than one methylene in each alkyl group is optionally and independently replaced by —O—, —S—, —N($R^o$)—, —C(H)=C(H)—, —C≡C—, —C(O)—, —S(O)—, —S(O)$_2$—, —P(O)(OH)—, —OP(O)(OH)—, —P(O)(OH)O—, —N($R^o$)P(O)(OH)—, —P(O)(OH)N($R^o$)—, —OP(O)(OH)O—, —OP(O)(OH)N($R^o$)—, —N($R^o$)P(O)(OH)O—, —N($R^o$)P(O)(OH)N($R^o$)—, —C(O)O—, —C(O)N($R^o$)—, —OC(O)—, —N($R^o$)C(O)—, —S(O)O—, —OS(O)—, —S(O)N($R^o$)—, —N($R^o$)S(O)—, —S(O)$_2$O—, —OS(O)$_2$—, —S(O)$_2$N($R^o$)—, —N($R^o$)S(O)$_2$—, —OC(O)O—, —OC(O)N($R^o$)—, —N($R^o$)C(O)O—, —N($R^o$)C(O)N($R^o$)—, —OS(O)O—, —OS(O)N($R^o$)—, —N($R^o$)S(O)O—, —N($R^o$)S(O)N($R^o$)—, —OS(O)$_2$O—, —OS(O)$_2$N($R^o$)—, —N($R^o$)S(O)$_2$O—, or —N($R^o$)S(O)$_2$N($R^o$)—, wherein each $R^o$ is independently hydrogen or $C_1$-$C_6$ alkyl. In certain embodiments, a divalent linking group can e of the formula, -Q-$C_0$-$C_{10}$ alkyl-. In certain embodiments, a divalent linking group can be of the formula, —$C_0$-$C_{10}$ alkyl-Q-. In certain embodiments, a divalent linking group can be of the formula, —$C_0$-$C_{10}$ alkyl-. In certain embodiments, a divalent linking group can be of the formula, —$C_1$-$C_{10}$ alkyl-.

"Alkylamine" as used herein means an alkyl group, as defined herein, substituted with an amino group. Examples of alkylamines include, but are not limited to 1-aminodecane, 1-aminododecane, 1-aminoeicosane, and the like.

"Alkenylamine" as used herein means an alkenyl group, as defined herein, substituted with an amino group. Examples of alkenylamines include, but are not limited to oleylamine, 1-amino-2-decene, 1-amino-8-decene, 1-amino-9-decene, 1-amino-2-dodecene, 1-amino-6-dodecene, 1-amino-11-dodecene, and the like.

EXAMPLES

Example 1

ZnS Nanowires

Zinc nitrate tetrahydrate ($Zn(NO_3)_2 \cdot 4H_2O$, 99.8%), Sulfur (S, 99.998% powder), Oleylamine (OAm, technical grade, 70%), 1-Dodecanethiol (DDT, ≥98%), methanol (≥99.5%), ethanol (99%), isopropyl alcohol (IPA, 99%), and Hexane (≥95%), 2-aminopyridine (≥99%), were purchased from Sigma-Aldrich and used without further purification.

S precursor solution was prepared in a flask, where 4 mmole of S powder was mixed with 20 mL OAm and kept at 100° C.; the mixed solution was switched between $N_2$ gas and vacuum to remove moisture and $O_2$; then the solution was stirred for 2 hours under $N_2$ before use. Secondly, Zn-OAm complex precursor solution was prepared by adding 0.4 mmole of $Zn(NO_3)_2$ and 2.0 mmole of DDT to 15 mL OAm in another flask, kept at 160° C. and stirred until a uniform mixture was formed. Thirdly, 2 mL of S-precursor solution was swiftly injected into the Zn-OAm precursor solution through a syringe with continuous stirring. After injection, the reaction temperature was raised to 230° C. at a speed of 15° C. per minute and maintained at this temperature. Timing was started when the temperature reached 230° C. and maintained at this temperature. After 3 minutes, the reaction was stopped by injection the hot reaction solution into a mixture of methanol (3 equivalent), ethanol (3 equivalent), and IPA (3 equivalent) at room temperature. The resulting solid product was centrifuged at 2,500 rpm 4° C., then re-dissolved in hexane and washed three times by centrifugation. The final product was redispersed in hexane for optical and TEM measurements. The synthesis of other ZnS samples was performed by changing one of the experimental parameters as indicated such as the amount of DDT, temperature, and reaction time, while keeping the other experimental parameters the same.

High-resolution transmission electron microscopy (HR-TEM), high angle annular dark field scanning transmission electron microscopy (HAADF-STEM), and energy dispersive X-ray spectroscopy (EDS) were performed on a JEOL JEM 2010F electron microscope operating at 200 kV. Powder X-ray diffraction (XRD) measurements employed a PANalytical X'Pert Pro Materials Research X-ray Diffractometer with Cu Kα radiation ($\lambda$=1.5418 Å) and scanned at a rate of 0.025 deg/s. Ultraviolet-Visible (UV-Vis) absorption spectra were recorded at room temperature with a JASCO V670 spectrophotometer. Photoluminescence (PL) and PL excitation (PLE) spectra were measured at room temperature using a NanoLog spectrometer manufactured by HORIBA Jobin Yvon equipped with a thermoelectric cooled PMT (R928 in the range 200 nm to 850 nm). The quantum yield (QY) of nanowires was measured relative to a standard (2-aminopyridine (≥99%) in 0.1 M H2SO4, QY=60%) following a procedure reported in the literature. (see, Z. T. Deng, F. Q. Tang, and A. J. Muscat, *Nanotechnology* 2008, 19, 295705). The time-resolved emission decay kinetics was measured using the time-correlated single-photon counting (TCSPC) technique. Data was fit with a sum of exponential decay model.

Figure 4:
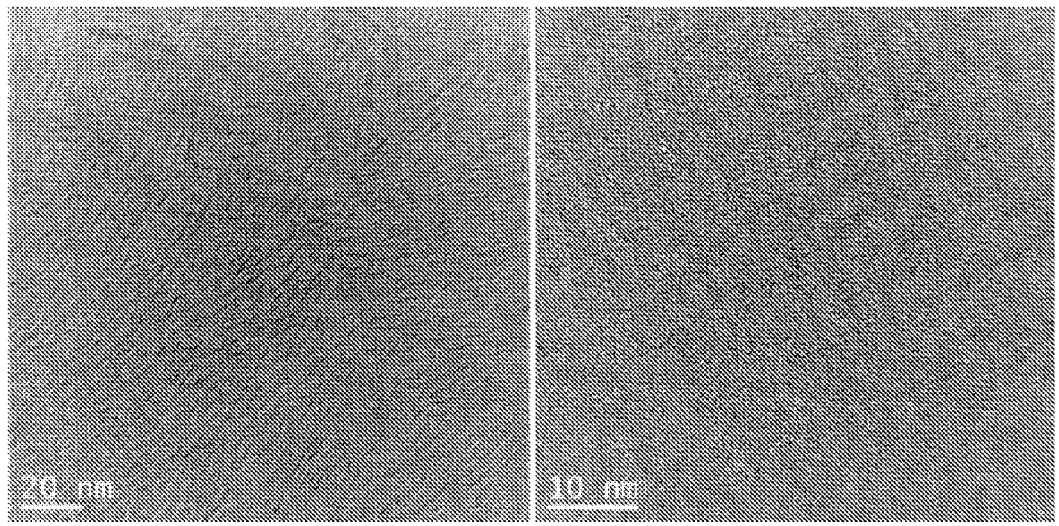
FIG. 4. Additional TEM images of the ultrathin ZnS nanowires with magic-size diameter.
Figure 5:
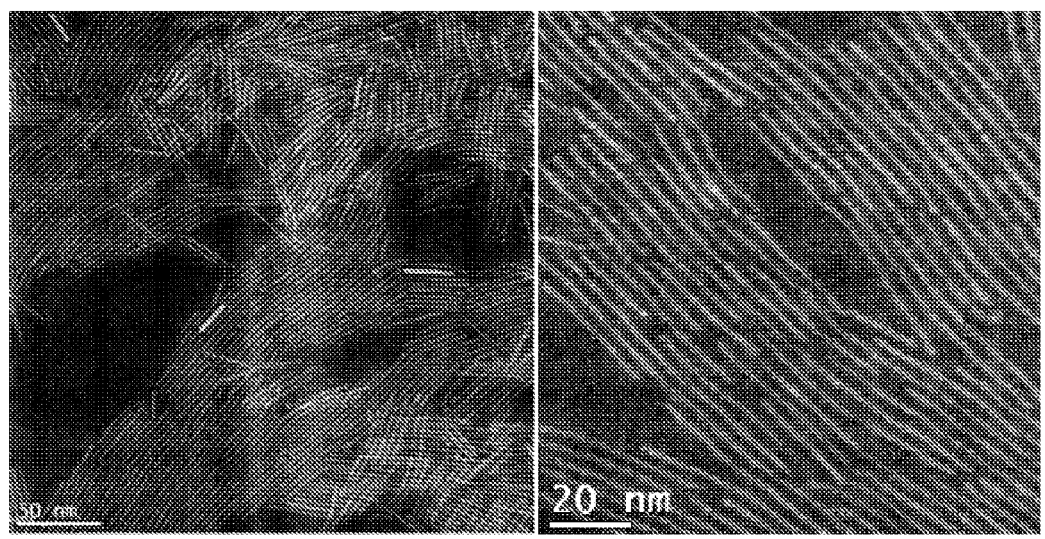
FIG. 5. Additional STEM images of the ultrathin ZnS nanowires with magic-size diameter.
Figure 6:
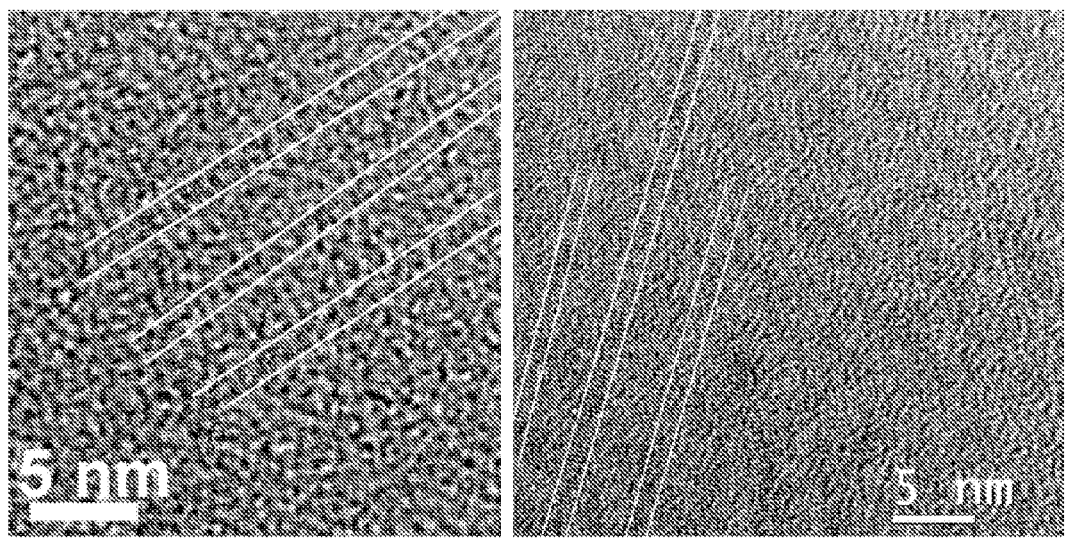
FIG. 6. Additional HRTEM images of the ultrathin ZnS nanowires with magic-size diameter.
Figure 7:
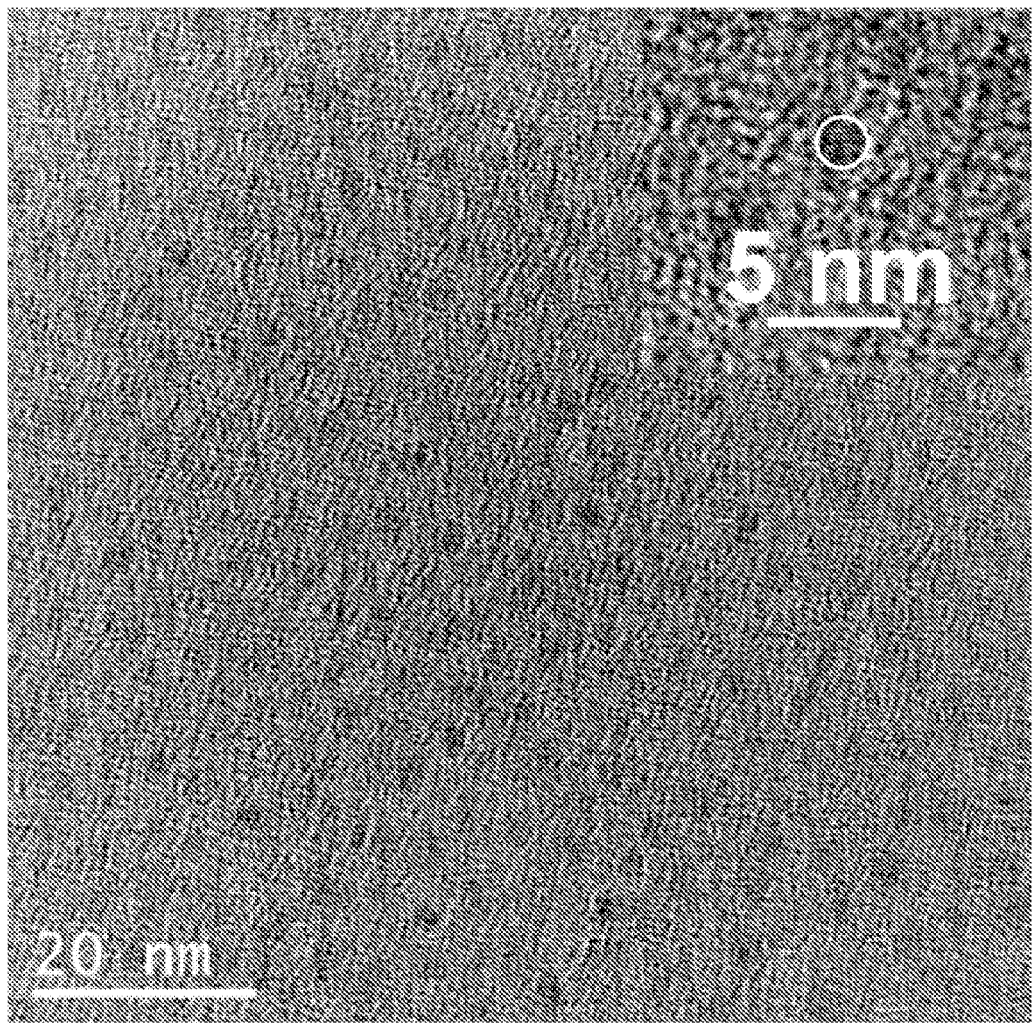
FIG. 7. HRTEM image of the ultrathin after electron beam (E-beam) illumination for 2 minutes. Inset showing a typical spherical magic-sized ZnS nanocrystal with diameter around 1.5 nm as marked by a white cycle.
Figure 8:
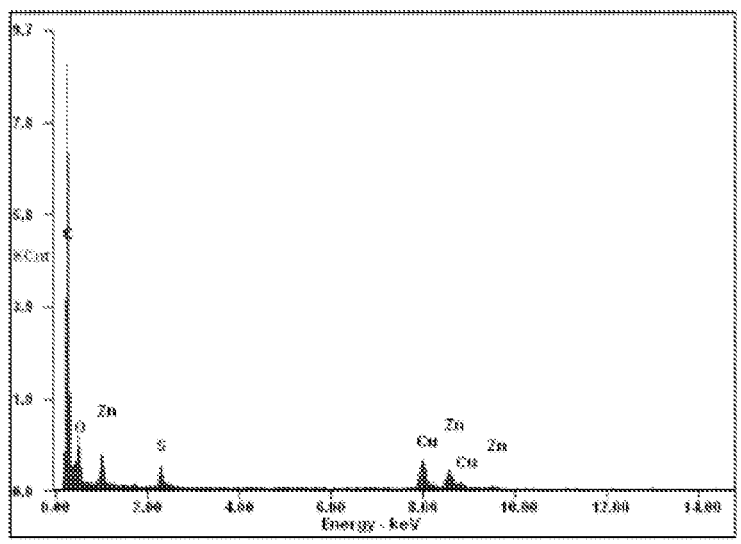
FIG. 8. Energy dispersive X-ray spectroscopy (EDS) spectrum of the ultrathin ZnS nanowires with magic-size diameter. The atomic ratio of the Zn:S is listed in the tables.

Transmission electron microscopy (TEM) images (FIG. 1*a* and FIG. 4) show the formation of NWs with large aspect ratio and lengths of up to 250 nm. The contrast of the TEM images is low, possibly because of the extremely small diameter of the NWs. To obtain better microscopic images, we used high-angle annular dark-field scanning transmission electron microscopy (HAADF-STEM) to image these NWs, which gave much higher image contrast (FIGS. 1*b-d* and FIG. 5). The STEM images also provide direct evidence for the formation of higher-order structures. When the sample was dried on the TEM grid, it is found that the NWs tend to align parallel to each other to form closely packed array structures (FIG. 1*c*), which was confirmed by fast Fourier transform (FFT, FIG. 1*c* inset). In addition, overlapping layers of arrays were also observed (FIG. 1*d*). The formation of these ordered arrays provides further evidence that the NWs have highly uniform diameters. High-resolution TEM (HRTEM) images (FIGS. 1*e-g*) revealed that the NWs have a uniform and narrow diameter of 1.2 nm. The NWs have preferred crystallographic orientation of [111]. The well-resolved lattice structure of individual NWs (FIG. 1*f,g*) indicates that the NWs are single-crystalline. The distinct lattice spacings were measured to be approximately 0.31 nm, corresponding to the [111] plane spacing of cubic zinc blende (ZB) phase of ZnS (cell constant a=5.345_; JCPDS Card No. 80-0020). This result also indicates that the NWs grow along the [111] direction. It should be noted that special care is needed to image these ultrathin NWs because they tended to break into spherical nanocrystals if they were exposed in a strong electron beam for a few minutes. The powder X-ray diffraction (XRD) pattern of the NWs (FIG. 2a) can be indexed to a cubic ZB phase, which is consistent with the HRTEM observations. The narrow (111) peak is due to the very large size (ca. 250 nm) in the length direction, while the broad (220) peak is due to the very small size (ca. 1.2 nm) in the width direction. The (311) peak intensity decreased significantly relative to bulk ZB phase ZnS, indicating the preferred crystallographic orientation of the product. These unusual characteristics of the XRD pattern are consistent with the unique geometry of the ultrathin NWs, which is expected to exhibit overlap of extremely broad and sharp features due to extreme difference of coherence lengths along different crystallographic axes.[2] The energy-dispersive X-ray spectroscopy (EDS) spectrum (FIG. 8) suggests that the NWs are composed of Zn and S. Quantitative EDS spectrum shows an atom ratio of Zn:S is 49.1:50.9, which is close to 1:1 and confirms the composition of the as-synthesized product is ZnS.

Figure 2:
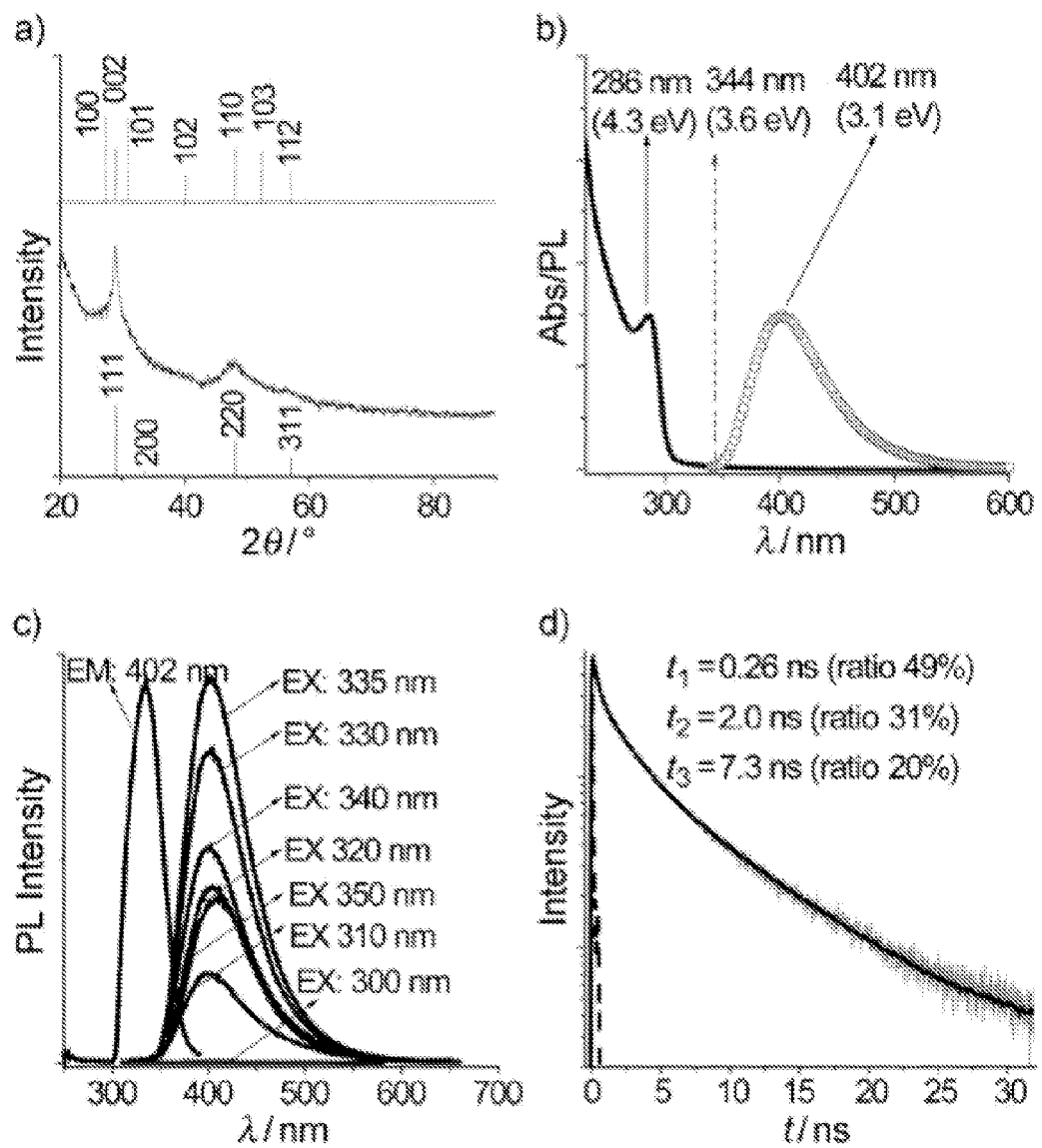
FIG. 2. a) XRD pattern of the magic-size ZnS nanowires and reference patterns (vertical lines) from JCPDS card No. 80-0020 (zinc blende, bottom) and JCPDS card No. 80-0007 (wurtzite, top). b) Room-temperature UV/Vis absorption (solid black line) and photoluminescence spectra (circles) of NWs. The dashed vertical arrow points to the bulk ZnS band gap. c) PL excitation and emission spectra monitored at different wavelengths; Em: 402 nm, emission monitored at 402 nm; Ex: 335 nm, excitation wavelength at 335 nm. d) Room temperature PL emission decay curve (gray) of the NWs with 402 nm emission and 355 nm excitation; the solid black line is the corresponding fitting curve; and the dashed line is the instrument response function curve.
Figure 3:
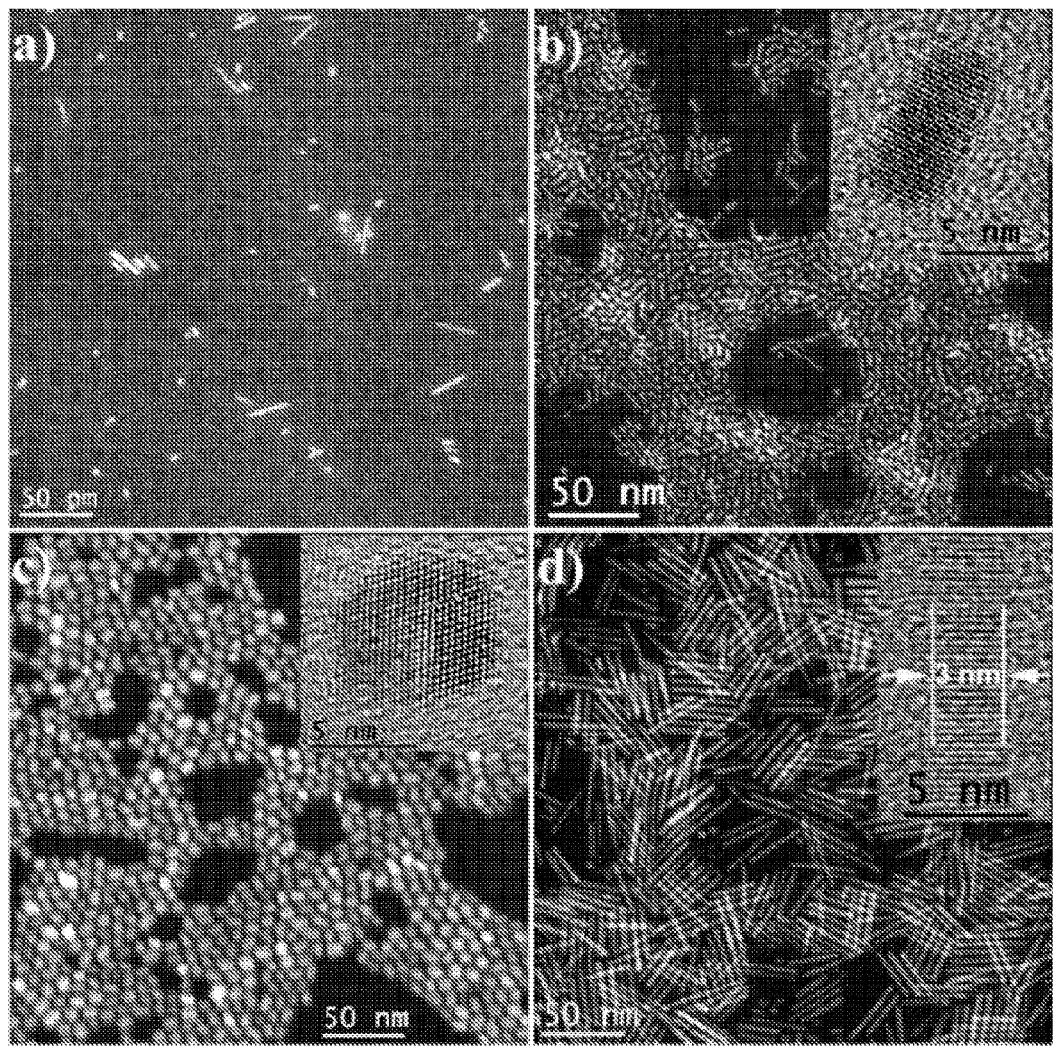
FIG. 3. STEM images of different ZnS samples obtained by varying the experimental parameters used for magic-size NWs growth. a) Spherical nanocrystals and short nanorods grown without DDT. b) Short, branched, and wormlike nanorods grown with overdosed DDT (DDT:Zn=30:1); c) Large spherical nanocrystals grown at increased temperature (at 260° C.). d) Long nanorods grown with overgrowth time. Insets in (b-d) show HRTEM images of the typical products.

The UV/Vis absorption and photoluminescence (PL) emission spectra of the ultrathin ZnS NWs dispersed in hexane were measured at room temperature (FIG. 2b). The distinct peak at l=286 nm (4.34 eV) is due to the first exciton absorption band of the ultrathin NWs. The large blue-shift (ca. 0.74 eV) relative to the bulk zinc blende ZnS band gap (3.60 eV) indicates the existence of very strong two-dimensional quantum confinement effect,[12] which is due to the ultrathin diameter of the NWs. The sharp absorption peak also indicates that the NWs are uniform in diameter, which is consistent with the TEM and STEM results. The PL emission spectrum exhibits a broad band peak at l=402 nm (3.08 eV) and a full width at half maximum of approximately 0.6 eV, which could be assigned to the surface states.[30] To further reveal the PL properties of the sample, the emission spectra were collected with the excitation wavelength varied in discrete steps in the range from 300 to 350 nm (FIG. 2c). The emission peak at 402 nm (3.08 eV) showed a slight red shift (<5 nm) with longer excitation wavelengths, reflecting an intrinsic surface-related states of the NWs. The excitation spectrum with emission monitored at 402 nm revealed a narrow PLE peak centered at l=335 nm (3.70 eV), that is more than 0.64 eV away from the exciton absorption peak. This result further suggests that the emission originates from the surface-related states, not from the direct band-gap excitation. The magic-size diameter of the NWs causes a significant increase of surface-to-volume ratio, which leads to the increase in amount of surface states. The PL quantum yield of the NWs was measured to be around 0.08, which is higher than the surface-related PL emission of ZnS nanocrystals (0.014) and nanorods (0.011) reported in the previous study. [27] The room-temperature time-resolved emission decay curve (FIG. 2d) at 402 nm fits well to a triexponential function with three characteristic time constants 0.26 ns (49%), 2.0 ns (31%), and 7.3 ns (20%). The amplitude weighed average decay time is 2.2 ns. The exact mechanism of growth of ultrathin ZnS nanowires is still largely unknown. We postulate that the formation of ultrathin ZnS nanowires may be attributed to a ligand-controlled oriented-attachment mechanism, as demonstrated previously for the cubic (ZB) ZnS nanorods synthesized with OAm as the capping ligand.[27] Our ultra-small ZnS nanocrystals could coalesce during the oriented attachment process to form the ultrathin ZnS nanowires with their (111) planes perfectly aligned. This behavior might be because the capping ligands (OAm and DDT) bind stronger to planes such as {220} and {100}, but more weakly to the {111} plane.[2, 8, 27, 31] This preference is evidenced by the h111i growth direction of the nanowires shown in the HRTEM image (FIG. 1g). We found that with OAm but without DDT, short nanorods and spherical nanocrystals (FIG. 3a) were obtained. Moreover, if overdosed DDT was used (molar ratio of DDT:Zn_30:1, instead of around 5:1), the products were short, branched, or wormlike nanorods (FIG. 3b). OAm has a double bond in the middle of the chain, which prevents the formation of ordered monolayers stabilized by van der Waals interactions,[2] whereas DDT, without the double bond, is likely to form more closely packed monolayers. DDT may bind stronger on the sides of the ZnS nanowires than does OAm, which will greatly reduce the surface energy of the side planes (such as {220}), thus keeping it from growing wider. As a result, ultrathin nanowires with large aspect ratios were obtained.

Temperature is also important for the ultrathin NW synthesis. When the synthesis was performed at the higher temperature of 260° C., instead of 230° C., only large (ca. 6 nm) spherical nanocrystals were produced (FIG. 3c). Finally, if the ultrathin NWs were aged at 230° C. for a longer time (from 3 to 15 min), the NWs became thicker and shorter nanorods: the average length shrunk from 250 to 40 nm; the diameter grew from 1.2 to 3.0 nm; and the average aspect ratio of NWs decreased from about 208 to 13 (FIG. 3d). The volume of the NWs remained constant at about 282 nm3, which implies that the shape evolution is by a diffusion-controlled one-dimensional to two-dimensional intraparticle ripening as a result of the extremely high overall chemical potential of the NWs shape. This result is consistent with the temporal shape evolution of CdSe nanorods previously observed.[32] The above results indicate that high quality magic-size NWs can be synthesized by using the optimized experimental parameters in a well-controlled manner. The as-synthesized ultrathin NWs are stable in hexane at room temperature for months if purified from the reaction mixture.

Figure 9:
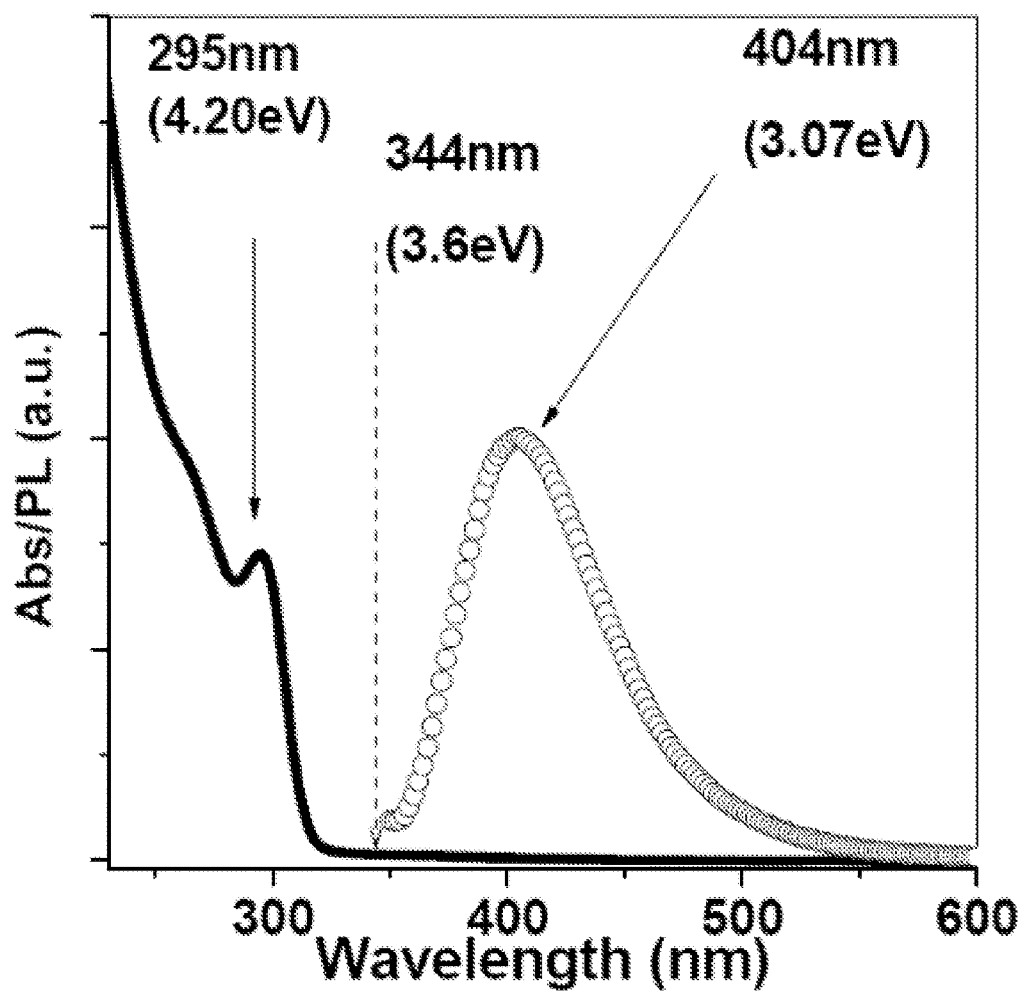
FIG. 9. UV-Vis absorption (solid black line) and photoluminescence (PL) emission (cycle line) spectra of the long ZnS nanorod sample (~3 nm in diameter) shown in FIG. 3d of the main context, demonstrating the size-dependent uv-vis absorption band and surface-defect related PL emission band.

The absorption and emission spectra of the 3 nm diameter ZnS nanorods are shown in FIG. 9. Relative to the 1.2 nm diameter ZnS nanowire, the absorption peak red shifts from l=286 nm to l=295 nm (0.14 eV shift), and the emission peak shows only a slight shift from l=402 nm to l=404 nm (0.01 eV shift). This observation is consistent with the assignment of the emission to surface states, which is expected to experience less quantum confinement effect than the exciton bandgap.

In summary, we have developed a facile colloidal chemistry for synthesis of ultrathin ZnS nanowires with magic-size diameter of 1.2 nm. Strong quantum confinement effects related to the unique nature of these ultrathin NWs were observed. We believe these ultrathin NWs could find broad use in sensors, photodetectors, host materials for diluted magnetic semiconductors (DMSs), and other nanodevice applications. These ultrathin NWs may also be used as a model to study the strong quantum confinement effect in a one-dimensional system. By choosing appropriate precursors and synthetic parameters, it is reasonable to expect that the present method could be extended to the synthesis of other ultrathin semiconductor NWs with magic-size diameter.

Example 2

Mn-Doped ZnS Nanowires

Zinc nitrate tetrahydrate (Zn(NO3)2.4H2O, 99.8%), manganese nitrate hydrate (Mn(NO3)2.xH2O, 99.99%), sulfur (S, 99.998% powder), oleylamine (OAm, technical grade, 70%), 1-Dodecanethiol (DDT, g98%), methanol (g99.5%), ethanol (>99%), isopropyl alcohol (IPA, 99%), and hexane (g95%), and Coumarin 480 were purchased from Sigma-Aldrich and used without further purification.

Our strategy to synthesize Mn-doped ZnS QRs is based on phosphine-free colloidal chemistry, with the advantages of being fast, simple and environmental friendly. The synthesis of Mn-doped ZnS QRs for a typical sample with a diameter of 2.0 nm (sample QR2) was as follows:

S precursor solution was prepared by dissolving 4 mmol of S powder in 20 mL OAm and holding the solution at 100° C.; then the solution was continuously stirred for 2 h before use. Second, Zn/Mn-OAm complex precursor solution was prepared by adding 0.4 mmol of $Zn(NO_3)_2$, 0.02 mmol of $Mn(NO_3)_2$, and 0.5 mL of DDT to 15 mL OAm in a flask, which was kept at 160° C. and stirred until a uniform mixture was formed. Third, 2 mL of S-precursor solution was quickly injected into the Zn/Mn-OAm precursor solution through a syringe with continuous stirring. After injection, the temperature was raised to 230° C. with a temperature ramp of 15° C. per minute. After 10 min at 230° C. (timing started once the temperature was reached), the solution mixture was removed from the heating mantle, and mixed with cold methanol (3 equivalents), ethanol (3 equivalents), and isopropyl alcohol (3 equivalents). Unreacted starting materials were removed by centrifugation (3,000 rpm for 30 min at 4_C) and the samples were redispersed in hexane (1 equivalent). The centrifugation and re-dispersion were repeated three times. The synthesis of Mn doped ZnS QRs with various Mn levels and diameters was achieved by changing the starting $Mn2⁺$ concentration and reaction times as summarized in Table 1, while keeping the other experimental parameters the same. The final products were redispersed in hexane for characterizations.

Characterization. Samples for TEM analysis were prepared by dropping a diluted hexane solution of doped QRs onto the ultrathin carbon-coated copper grids and air-dried. TEM, HRTEM, HAADFSTEM, and energy dispersive X-ray spectroscopy (EDS) were performed on a JEOL JEM 2010F electron microscope operating at 200 kV. For the powder XRD measurements, the QR samples were dried on a quartz substrate, and it was performed on a PANalytical X'Pert Pro Materials Research X-ray Diffractometer with Cu KR radiation ($\lambda$=1.5418 Å) and scanned at a rate of 0.025 deg/s. ICP-MS was performed on a Thermo X-series Q-ICP-MS with CCT (Collision Cell Technology) instrument. Mn was measured at $^{55}$Mn, while Zn was measured at $^{64}$Zn, $^{66}$Zn and $^{68}$Zn. The Zn isotope with the lowest detection limit ($^{66}$Zn) was selected for reporting, but all three isotopes gave values within 5% of each other. Two standard checks and a blank were measured for every four sample analyses, and each sample was measured for at least three different dilutions. The variation of the Zn/Mn ratio measured in two separate dilutions for each sample was always less than 3%, and typically less than 1.3%. The doping level of Mn in the ZnS QRs was calculated from the atomic ratio of the Mn/(Mn+ Zn) measured.

UV-vis absorption spectra were recorded at room temperature with a JASCO V670 spectrophotometer. Photoluminescence spectra were measured at room temperature using a NanoLog fluorescence-spectrometer manufactured by HORIBA JobinYvon equipped with a thermoelectric cooled PMT (R928 in the range 200_850 nm), a 450 W xenon short-arc lamp, and a flash lamp (for phosphorescence decay lifetime). The emission spectra obtained were corrected using a response file that records the sensitivity of the PMT to different wavelengths of light generated using a standard lamp. The excitation spectra were corrected using the signal from the reference photodiode that records the variation of the intensity of the lamp with excitation wavelength.

EPR study was performed at the EPR Facility at Arizona State University. EPR spectra were recorded at room temperature using a Bruker ELEXSYS 580 X-band spectrometer (Bruker, Silberstreifen, Germany) equipped with a cylindrical mode resonator (Bruker, ER 4103™) designed for aqueous and high-dielectric samples. Samples were placed in a flat, quartz cell, which was mounted in the resonator. The parameters used were: magnetic field modulation frequency 100 kHz, amplitude 1 mT, microwave power 10 mW, microwave frequency 9.7 GHz and the sweep time 84 s. The spectra were obtained by averaging 8-12 scans. The time-resolved PL spectroscopic study was performed on a system consisting of an ultrafast laser and streak camera detection system. The intensity of PL as a function of emission wavelength and time for the Mn-doped ZnS QRs samples was recorded simultaneously. The 130-fs light pulses at 650, 700, or 730 nm were generated from a visible OPA pumped by a femtosecond regenerative amplifier system operating between 10 and 250 kHz (Coherent Laser Inc., Verdi 18, Mira900, RegA9000, OPA9400). The laser radiation was then frequency-doubled in a single pass configuration within a nonlinear crystal to produce femtosecond UV radiation at 325, 350, and 365 nm. A femtosecond laser (Maitai, Spectra-Physics, Fremont, Calif.) with 130-fs pulse and 80 MHz repetition rate, tunable within 690_1020 nm, was used as the excitation source for multiphoton imaging. The laser beam was sent into a FV1000 laser-scanning microscope (Olympus America Inc., PA) and focused onto thr sample with a 60X/IR water objective lens (NA=1.2). The backward multi-photon signals were collected using the same objective, separated from the excitation laser by a dichroic mirror and detected by two internal spectral detectors (channel 1 and channel 2). The detection range was set as 400_500 nm for channel 1 and 560_660 nm for channel 2, separated by a diachronic mirror (SD560). Microspectroscopy was performed by $\lambda$-scan using the internal spectral detector in the confocal scanning box. Details of the optical setup can be found elsewhere (see Chen, et al., Opt. Express 2009, 17, 1282; and Tong, et al., Angew. Chem., Int. Ed. 2010, 49, 3485.

An exemplary synthesis of high-quality Mn-doped ZnS QRs is shown in Scheme 1.

Scheme 1. Schematic Illustration Our Simple, Fast, and "Green" Phosphine-Free Colloidal Chemistry for Synthesis of high-quality Mn-Doped ZnS QRs

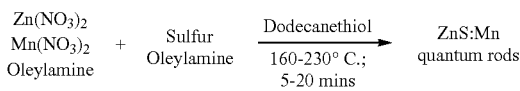

Air-stable and simple metal nitrate salts, $Zn(NO_3)_2$ and $Mn(NO_3)_2$, are employed as the metallic precursors, sulfur powder as the sulfur precursor, oleylamine as the solvent, 1-dodecanethiol as the capping ligand, and relatively short reaction times of 5-20 min. A series of QR samples, referred as QR1_QR8, were generated by varying the reaction time and the molar ratio of Mn/Zn precursors (see Table 1).

TABLE 1

Summary of Morphology Measurements from TEM, Mn-Doping Level Measurements from ICP-MS, and Optical Characterization of the Mn-Doped ZnS QR Samples; Initial Molar Ratio of Mn/Zn Precursors and Reaction Time Are Also Listed

| QR sample No. | Reaction time (minutes) | Sample size (nm) | Intial $Mn^{2+}$ concentrations (mol %) | Doped $Mn^{2+}$ concentration (mol %) | First exciton absorption band (nm) |
|---|---|---|---|---|---|
| QR1 | 5  | 1.6 × 80 | 5  | 0.18 | 286 |
| QR2 | 5  | 2.0 × 45 | 20 | 0.25 | 292 |
| QR3 | 10 | 2.3 × 38 | 5  | 0.32 | 294 |
| QR4 | 10 | 3.0 × 32 | 20 | 0.36 | 296 |
| QR5 | 15 | 3.3 × 30 | 5  | 0.37 | 298 |
| QR6 | 15 | 4.0 × 25 | 20 | 0.51 | 299 |
| QR7 | 20 | 5.0 × 22 | 5  | 0.81 | 300 |
| QR8 | 20 | 5.6 × 20 | 20 | 1.60 | 300 |

Figure 10:
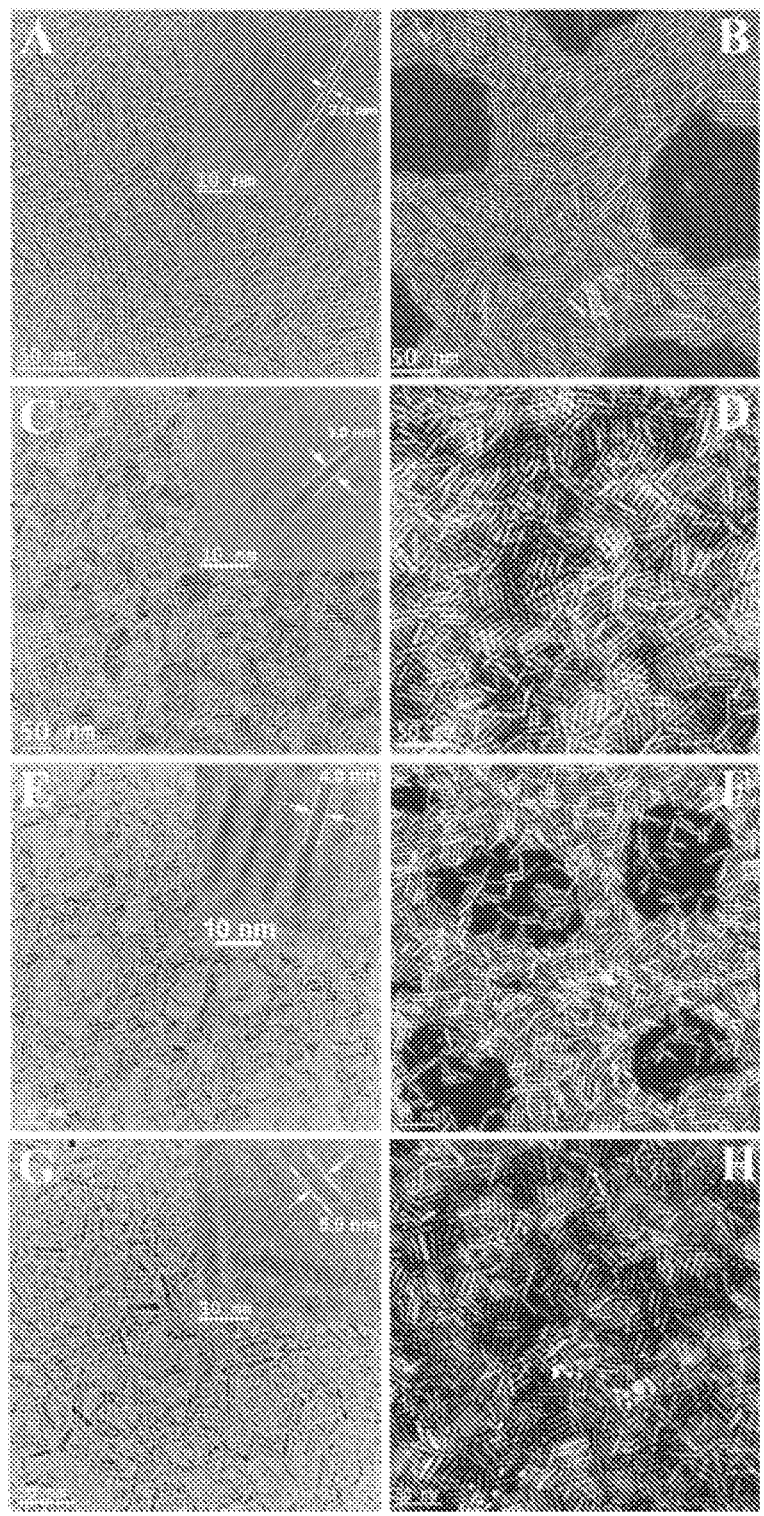
FIG. 10. Transmission electron microscopy (TEM) and scanning transmission electron microscopy (STEM) images of QRs with diameters of ~2.0 (A,B), ~3.0 (C,D), ~4.0 (E,F), and ~5.0 nm (G,H), respectively. Insets (A, C, E, and G) are selected zoom-in TEM images of the several QRs.

The morphology of the samples was revealed by transmission electron microscopy (TEM) and high-angle annular dark field scanning transmission electron microscopy (HAADF-STEM), which show the formation of high-quality QRs. Selected samples with diameters of 2.0, 3.0, 4.0, and 5.0 nm are depicted in FIG. 10. Each sample showed uniform diameters and lengths. In some cases, these QRs prefer to self-assemble into close packed three-dimensional (3D) superlattices with their long axes parallel to each other.

Figure 11:
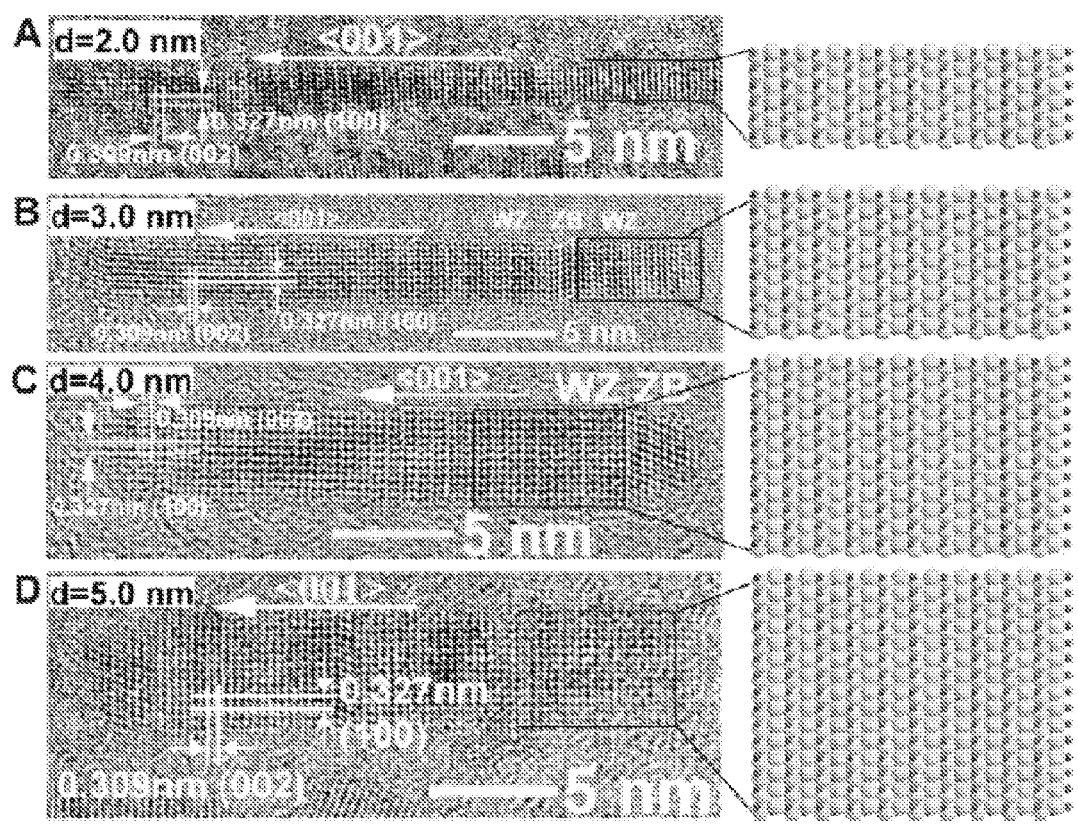
FIG. 11. High resolution transmission electron microscopy (HR-TEM) images of Mn-doped ZnS QRs with diameters of ~2.0 (A), ~3.0 (B), ~4.0 (C), and ~5.0 nm (D) and their corresponding structural models of the indicated areas. For all the structural models, the projection is <010>, the small cyan ball represents Zn or Mn atom and the large yellow ball represents S atom.

High-resolution TEM (HRTEM) study demonstrated well-resolved two-dimensional crystal lattices (FIG. 11), indicating that the individual QRs are highly crystalline. The lattice spacings of 0.309 nm in the length direction and 0.327 nm in the width direction correspond to the (002) and the (100) planes, respectively, which are consistent with the wurtzite phase of ZnS (JCPDS Card No. 80-0007) and powder X-ray diffraction (XRD) measurement. The wurtzite phase is dominant in the QR samples, as illustrated by the structural models (FIG. 11), while a small amount (<2%) of cubic zinc blende phase could also be observed. ZnS with hexagonal wurtzite and cubic zinc blende phases have several overlapping diffraction peaks, especially the (002), (110), and (112) peaks of wurtzite are close to the (111), (220), and (311) peaks of zinc blende. We speculate that the unique geometry of the QRs and the presence of Mn dopants, which can alter the crystal phase of the ZnS nanocrystals, contributes to the hexagonal wurtzite phase of ZnS QRs. This also agrees with the previous report on the ultrathin Mn doped ZnSe quantum wires, which also shows a hexagonal wurtzite phase.

The growth of anisotropic Mn-doped ZnS QRs, instead of spherical QDs, could be understood by a ligand controlled kinetic mechanism, which is similar to the growth of wurtzitetype CdSe QRs by manipulation of the growth kinetics. Wurtzite-type ZnS is a member of the hexagonal crystal system and consists of tetrahedrally coordinated zinc and sulfur atoms that are stacked in an ABABAB pattern. Their anisotropic unit cells have large c-axis of 6.188 Å, and small identical a- and b-axis of 3.777 Å (JCPDS Card No. 80-0007). Nearly spherical faceted QDs that minimize the total surface area is favored if the overall growth rate is slow. However, when the growth rate is fast using high monomer concentrations and optimal reaction temperatures, anisotropic QRs will grow with c-axis as their growth directions. The time-dependent morphology evolution of the Mn-doped ZnS QRs indicates that there exists an initial nucleation and fast longitudinal growth process; then followed by an aging process in which the long and thin QRs gradually grow shorter and wider (see Table 1). In addition, we obtained wider QRs (see Table 1) by increasing $Mn^{2+}$ precursor concentration and keeping other reaction parameters the same, which indicates that the presence of $Mn^{2+}$ dopants could also alter the growth kinetic of the QRs.

We used inductively coupled plasma mass spectrometry (ICPMS) to determine the concentration of Mn2+ doped in the ZnSQR samples, i.e., the Mn2+ doping levels, that were between 0.18% and 1.60% for samples QR1_QR8 (Table 1). TEM-based energy dispersive X-ray analysis (TEM-EDS) studies were also used to investigate the $Mn^{2+}$ doping levels but with less accuracy. It is known that $Mn^{2+}$ is a harder Lewis acid compared to Zn2+. Therefore, Mn2+ would be less reactive than Zn2+ if they were present at the same reaction environments. The Mn2+ doping levels showed a nonlinear correlation with the reaction time and QR diameters, which is due to the kinetic, not the thermodynamic, controlled QR growth process. The relative low doping levels (0.18_1.60%) of the Mn-doped ZnS QRs is attributed to their small diameters (1.6_5.6 nm), in contrast to the higher doping level (20%) for Mn-doped ZnS nanorods with a much larger diameter (~100 nm)

Figure 12:
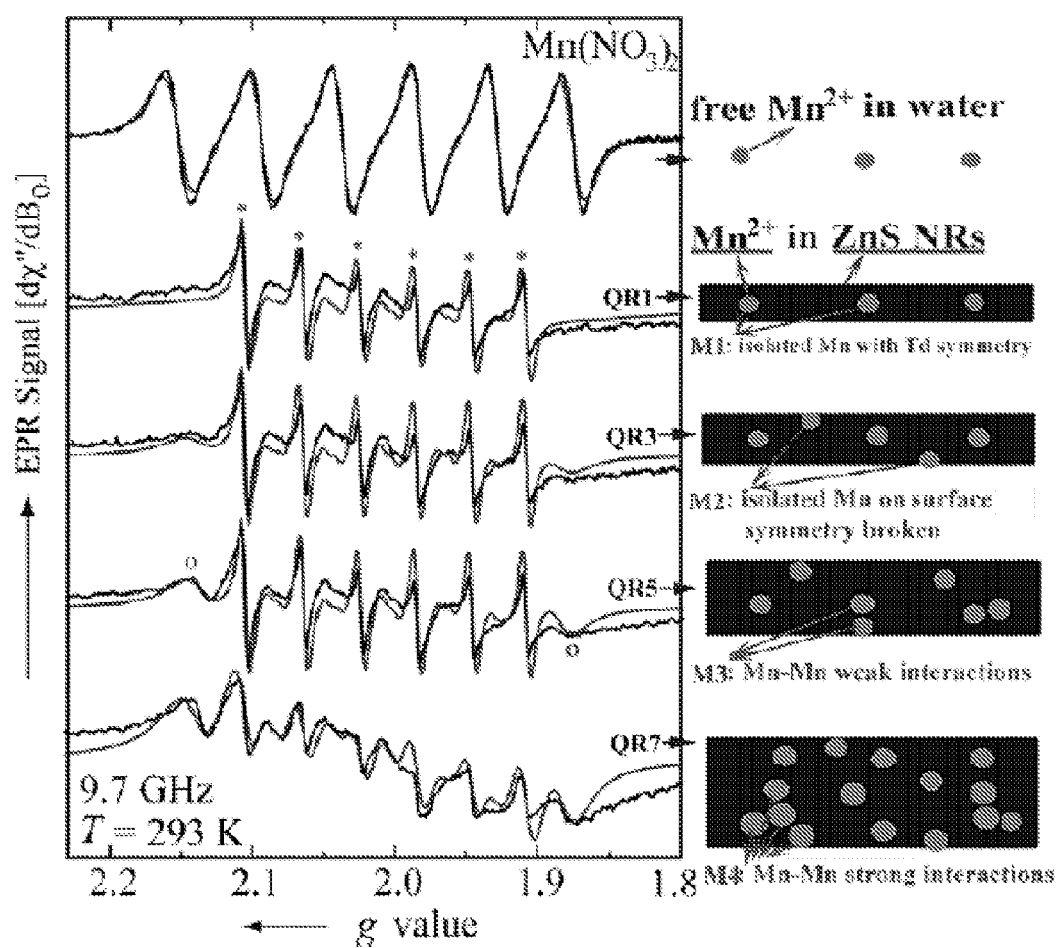
FIG. 12. Electron paramagnetic resonance (EPR) spectroscopic characterization of Mn-doped ZnS QRs. Room temperature EPR spectra (black), simulation (red) and the corresponding schematic representation of Mn-doped QR samples with various diameters and doping levels: QR1, QR3, QR5, QR7, respectively. The EPR spectrum of 1 mM $Mn(NO_3)_2$ in aqueous solution is shown for comparison. Four different scenarios are illustrated for Mn2+ ions doped in the ZnS QRs. M1: isolated Mn2+ ions with symmetric tetrahedral coordination to sulfur, i.e. Mn2+ doped inside the ZnS QRs with symmetric tetrahedral coordination; M2: isolated Mn2+ with asymmetric tetrahedral coordination, i.e. Mn2+ doped on the surface of ZnS QRs; M3: weak dipole_dipole interaction between Mn2+ ions with intermediate Mn2+ doping level; M4: strong exchange coupling interaction between Mn2+ with high doping level.

To reveal the local environment of Mn2+ ions doped in the QRs, we performed the X-band electron paramagnetic resonance (EPR) spectroscopy study. As depicted in FIG. 12, the EPR spectra corresponding to samples QR1, QR3, QR5, and QR7 exhibit well-resolved hyperfine splitting lines, which indicates the presence of the paramagnetic Mn2+ ions in the samples. We extracted a hyperfine coupling interaction of 192 MHz for the Mn2+ doped QRs samples and 267 MHz for free Mn2+ ions in aqueous solution, indicating that the hyperfine splitting of $Mn^{2+}$ is strongly dependent on their local environments. This unambiguously confirmed the successful doping of paramagnetic Mn2+ ions in the ZnS crystal lattice.

Furthermore, we performed the simulations for the EPR spectra with a spin Hamiltonian containing a zero field splitting interaction, an electron Zeeman interaction with the applied magnetic field, and a hyperfine coupling interaction. From the simulation, we identified four different scenarios that describe the different local environments of the doped Mn2+ in the ZnS QRs with various diameters and doping levels, labeled as M1, M2, M3, and M4 in the schematic diagram (FIG. 12). The EPR spectrum of the QR1 sample with the smallest diameter (1.6 nm), longest length (~80 nm), and the lowest doping level (0.18%) could be simulated very well using a single Mn2+ scenario of M1, which is isolated Mn2+ doped in the interior of the ultrathin ZnS QRs. This kind of Mn2+ is fully coordinated to the sulfur ions with a tetrahedral symmetry. Using the size and the doping level of QR1 depicted in Table 1 and assuming the Mn2+ ions distributed evenly along the longitudinal direction, the calculated Mn2+ ions per QR is ~7, and the calculated average distance between Mn2+ ions is ~10 nm. Thus, no interactions between the Mn2+ ions are expected. It is surprising that no surface Mn2+ (i.e., M2) but only symmetrically coordinated internal Mn2+ (i.e., M1) was observed for QR1 with an ultrathin diameter (1.6 nm), since a large fraction of the whole atoms of the QRs (>40%) is expected to be present on the surface. According to the "self-purification" effect observed in ultrasmall QDs, the Mn impurities tend to be repelled. This is because that the spherical QDs have very small interior volume, thus inner impurities can easily migrate to the surface and be excluded. In the case of anisotropic doped QRs, similar to the spherical QDs, the $Mn^{2+}$ on the surface is unstable and would be repelled from the host QRs, as lowering the surface energy of the QRs is preferred rather than hosting another atom on the surface. However, due to the large sizes (~80 nm) in the longitudinal direction, the host QRs may have enough interior volume to host the Mn2+ impurities with symmetric coordination. Therefore, only the internal symmetrically coordinated Mn2+ was found in the 1.6 nm QR1. These results indicated that we are capable of doping Mn2+ inside the ultrathin QRs with a magic-size (size <2 nm) diameter by a simple phosphine-free chemistry, which was not achieved before by other synthesis methods.

Sample QR3 has a larger diameter 2.3 nm and a higher doping level 0.32% as compared to QR1. The EPR study indicated that there exists both the surface Mn2þ (M2) with broken tetrahedral symmetry and the interior Mn2+ (M1) with tetrahedral symmetry. Further increasing QR diameters and Mn-doping levels, the Mn2+ ions doped in each QR will become closer (e.g., there are ~25 Mn2+ per QR with an average distance ~2 nm in QR5, and there are ~100 Mn2+ per QR with an average distance ~1.6 nm in QR7). As a result, weak dipole-dipole interactions (e.g., M3 in QR5) and strong exchange coupling interactions (e.g., M4 in QR7) between the doped Mn2+ ions show up, in addition to the M1 and M2 states (FIG. 12). Our EPR study demonstrated not only the strong evidence of the existence of the paramagnetic Mn2+ ions doped in the ZnS QRs, but also the underlying information about the locations and interactions of these doped Mn2+ ions.

Figure 13:
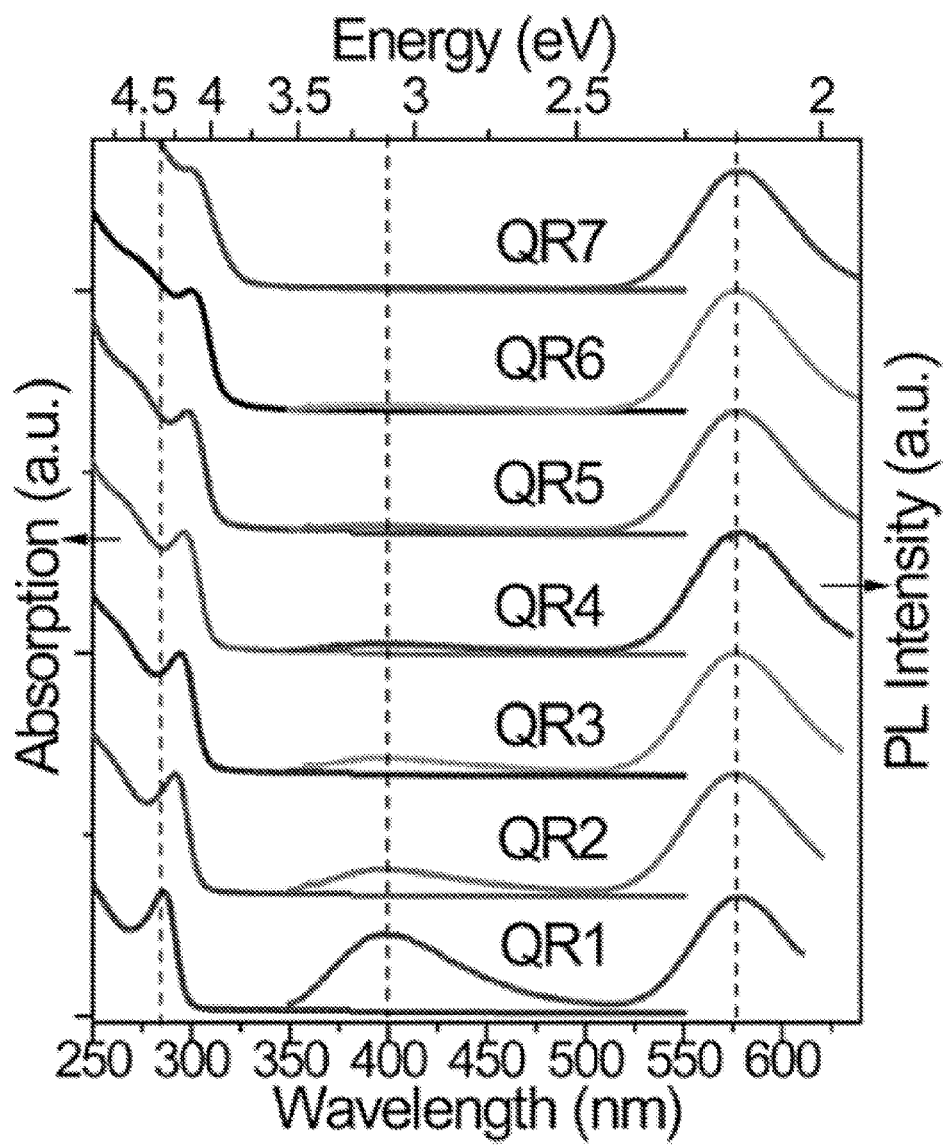
FIG. 13. Optical characterization of Mn-doped ZnS QRs. (left) UV_vis absorption spectra of the series of Mn-doped ZnS QRs. The first absorption band position (Table 1) shows a gradual red shift with increase in QR diameter. (Right) Room-temperature photoluminescent emission spectra with UV excitation at 300 nm (PL intensity normalized at 585 nm). To collect the PL emission spectra for excitation at 300 nm, a long pass filter (320 nm) was placed in front of the detector monochromator.

The as-prepared QRs samples dispersed in hexane are colorless and transparent under room light. However, they show very high extinction in the UV region. The UV-visible absorption spectra of the as-prepared samples with 500 times dilution are depicted in FIG. 13. The Mn-doped ZnS QRs (QR1_QR7) exhibit sharp, first exciton absorption bands, reflecting their uniform size (diameter and length). This was achieved by terminating the QR growth in the "focusing of size distribution" regime. The quality of the spectra is comparable to the best optical spectra of CdSe QRs or the Mn-doped ZnS QD counterparts in the literature. The peak of the exciton absorption band gradually shifts from 286 to 300 nm (4.34_4.14 eV) as the QR diameter increases from 1.6 to 5.6 nm. The shifts of the first absorption exciton peaks from the bulk wurtzite ZnS are plotted against the diameter of the Mn-doped ZnS QRs, revealing a nearly quadratic dependence. The blue shift of the band gap with narrowing the QRs could be explained by diameter-dependent 2D quantum confinement effect in QRs. The photoluminescent (PL) emission spectra from the samples (QR1_QR7) all contain distinct orange bands centered at 585 nm (see FIG. 13). These emission bands originate from the Mn2+ doping states, 25 indicating the successful doping of Mn2+ in the crystal lattice of the host ZnS QRs. In addition, the QR samples show the blue emission bands centered at 400 nm, which are attributed to the QR surface states. As shown in FIG. 13, with increasing Mn2+ doping levels and QR diameters from QR1 to QR7, the relative intensity of the blue bands to orange bands decreases, which is mainly due to the increasing intensity from the orange emission, while only small intensity changes (PL quantum yield ~3-8%) were observed from the blue emission. The above results suggest that the ratio of the dual-color emissions (orange and blue) of the Mn-doped ZnS QRs could be controlled by tuning the Mn doping levels of the QRs. It is worth to note that our previous work on undoped ZnS QRs and quantum wires only show blue emission band from the surface states, and no orange emission band from the Mn2+ impurity. The lack of the orange emission band in the PL spectrum of the undoped ZnS QRs further supports the claim that the orange emission is derived from the Mn2+ impurity.

Figure 14:
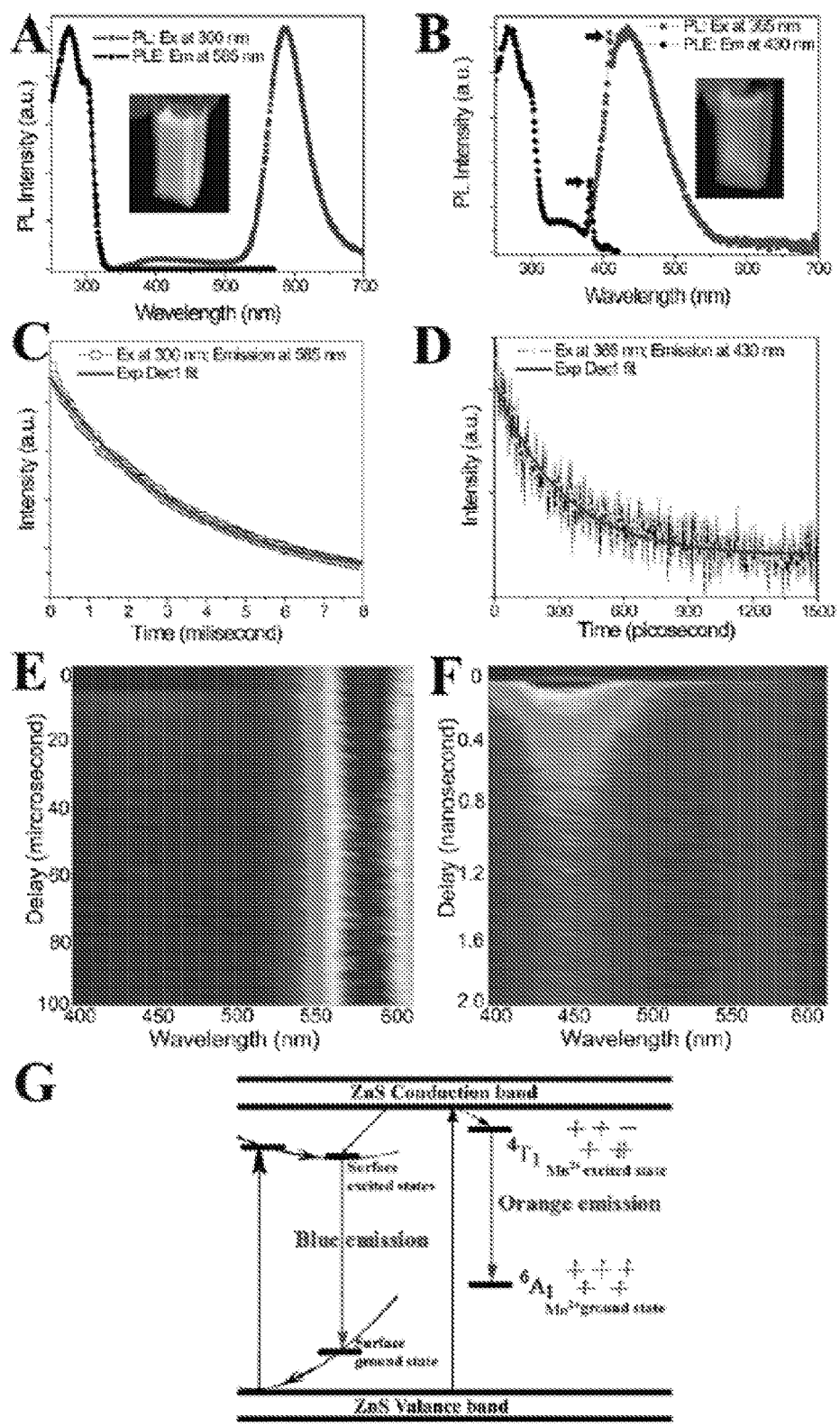
FIG. 14. Tunable dual emissions of Mn-doped ZnS QRs (sample QR4). (A) PLE (black) and PL (red) spectra of QRs with emission monitored at 585 nm and excitation at 300 nm, respectively; (B) PLE (black) and PL (blue) spectra of the same sample with emission at 430 nm and excitation at 365 nm, respectively; (C) phosphorescence decay curve (black) and its fitting curve (red) with excitation at 300 nm; (D) lifetime decay curve derived from the streak camera (black) and its fitting curve (blue) with excitation at 365 nm; (E) Time evolution of the PL spectrum excited with 325 nm pulsed laser (130 fs, 10 kHz). (F) Time evolution of the PL spectrum for the same sample excited with 365 nm pulsed laser (130 fs, 250 kHz); (G) schematic energy profile of electronic structures in the Mn-doped ZnS QRs for illustration of the two distinct emission mechanisms. The dark arrows in B indicate the Raman signals from the hexane solvent. Insets of A and B: optical images of the samples in a quartz cuvette exposed to short-wave and long-wave UV, respectively. All the measurements were performed at room temperature.

The tunable dual-color emissions of the Mn-doped ZnS QRs are further investigated by tuning the excitation wavelength (FIG. 14). As an example, we excited QR4 with 300 nm UV, an intense orange emission band centered at 585 nm (with PL quantum yield of 45%) and a weaker blue emission band centered at 400 nm (with PL quantum yield 3.4%) were observed (the optical image shown in FIG. 14A inset). The photoluminescent excitation (PLE) spectrum (black trace in FIG. 14A) of the orange emission resembles its absorption spectrum (see FIG. 13), indicating there exist an energy transfer from the host ZnS conduction band to the doped Mn2+4T1 state. The decay lifetime of the orange emission was ~3.3 ms (FIG. 14C) by measuring the phosphorescence decay using a microsecond flash lamp. The decay of the orange emission was also monitored on the 100 μs time scale using a streak camera system (see FIG. 14E), which only show a minimal decrease. Such slow decay further confirmed the assignment of this emission band to the spin forbidden doped $Mn^{2+}$ $^4T_1$ to $^6A_1$ transition. Moreover, using a longer excitation wavelength at 365 nm, the sample showed only blue emission (the optical image in FIG. 14B inset). The observation of the blue emission, instead of the orange emission, could be explained by their different PLE spectra. The PLE spectrum of the orange emission approaches baseline at excitation wavelength longer than 330 nm (black trace in FIG. 14A), while the PLE spectrum of the blue emission resembled the band gap absorption spectra of the ZnS QRs at short UV range (<320 nm), with additional intensities at longwave UV range (320-420 nm) (black trace in FIG. 14B). This observation indicates that the blue emission could be attributed to either the energy transfer from the host ZnS conduction band to the surface states or the direct excitation of surface states. Furthermore, when the excitation wavelength varied from 300 to 400 nm, the blue emission band exhibits a gradual red shift from 400 to 460 nm. This red shift could be explained by the heterogeneity of the surface states and relaxation of the vibrational states in both the electronic excited and ground states (FIG. 14G). Moreover, these surface states could act as the efficient electron hole recombination centers that have a very short emission decay lifetime of ~0.31 ns, as revealed by spectral resolved emission dynamics from the streak camera study (FIG. 14D). The decay of the blue emission is 107 fold faster than that of the orange emission.

Figure 15:
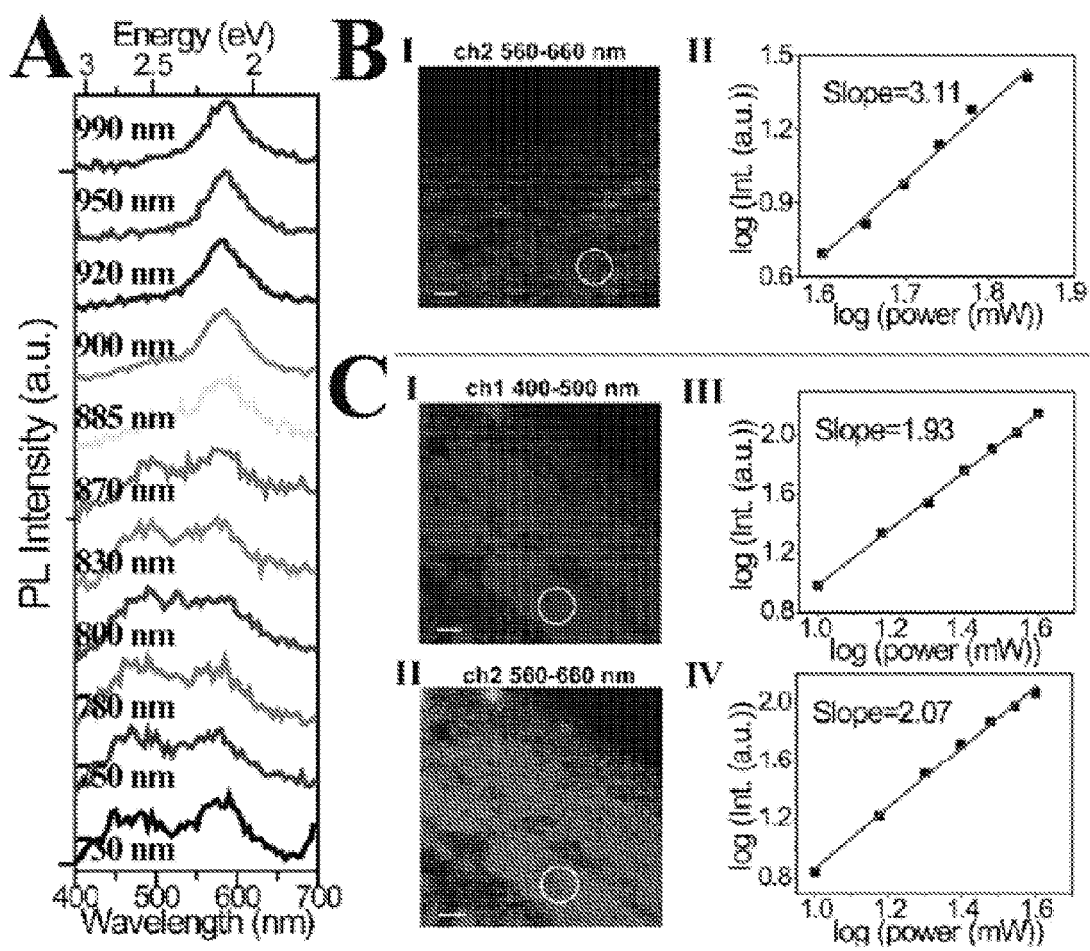
FIG. 15. Multiphoton luminescence of the Mn-doped ZnS QRs. (A) Emission spectra from the Mn-doped ZnS QR sample (QR4) spin coated on a cover slide, with a range of laser excitation wavelengths from 990 to 730 nm using 2-scan mode. (B) With 950 nm laser excitation: (I) multiphoton luminescence image acquired between 560 and 660 nm (Ch2); (II) dependence of the luminescence intensity on the excitation power from the circled area in (I), obtained by decreasing the excitation power from 1.56 mW to 0.89 mW at the sample; lower power was used to avoid saturation. (C) With 730 nm laser excitation: (I) luminescence image acquired between 400 and 500 nm (Ch1); (II) luminescence image acquired between 560 and 660 nm; the color of the image was assigned according to the emission peak position. (III) and (IV) dependence of the luminescence intensity on the excitation power from the same circled area in (I) and (II), obtained by decreasing the excitation power from 1.84 mW to 0.46 mW at the sample. The scale bars in the images are 5 μm. Note that the powers labeled in the x-axis of BII, CIII and IV are the laser power before the microscope (for example, 1.56 mW at sample corresponds to ~70 mW before the microscope). It will not affect the value of slopes in the double "log" plot here.42
Figure 16:
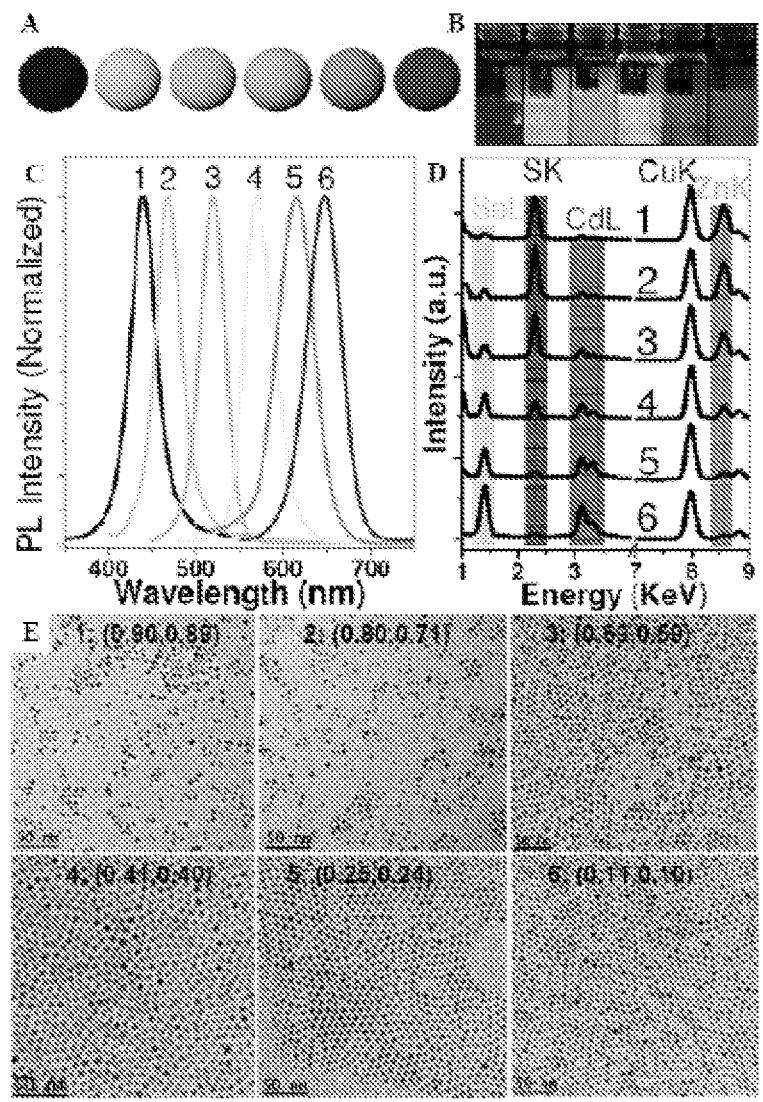
FIG. 16 (A) Schematic diagram illustrating the composition-dependent band edge emission of a series of $Zn_xCd_{1-x}S_ySe_{1-y}$ quantum dots with identical diameter. (B) Photograph of a quantum dot sample excited with a 365 nm UV lamp, (C) PL emission spectra, (D) TEM-EDS spectra, (E) TEM images of a series of ~6 nm quantum dots samples with varying composition. The compositions (x, y) as determined by TEM-EDS are: 1 (0.90, 0.89), 2 (0.80, 0.71), 3 (0.69, 0.59), 4 (0.41, 0.40), 5 (0.25, 0.24) and 6 (0.11, 0.10).

Our doped QRs exhibited bright multiphoton excitation luminescence. We studied the multiphoton luminescence for the QR samples using femtosecond laser excitation with tunable wavelength ranging gtom 990 to 730 nm (FIG. 15A). Specifically, using 950 nm laser excitation and λ-scan imaging (FIG. 15B1), a strong luminescence with a single peak centered at 585 nm was observed (purple trace in FIG. 15A). In addition, when the excitation wavelength was tuned from 990 to 900 nm, the emission spectra were dominated by the 585 nm emission. The cubic dependence of the signal intensity on the excitation power (FIG. 15B-II) confirmed that this emission is three-photon excitation luminescence (3PL). This indicates the orange emission observed here arise from the energy transfer from the three-photon excited host ZnS conduction band to the doped $Mn^{2+}$ $^4T_1$ state.

With 730 nm excitation and λ-scan imaging, dual luminescence spectra (FIG. 15A, black trace) with two bands centered at 450 nm (FIG. 15C-I) and 585 nm (FIG. 15C-II) were obtained. The quadratic dependence of the signal intensity on the excitation power for both channels (FIG. 15C-III,IV) confirmed two-photon luminescence (2PL). When intermediate wavelengths (from 800 to 885 nm) were used for excitation, power dependences of the emission were in between two and three, indicating a mixed 2PL and 3PL behavior.

Two-photon upconversion luminescence of Mn2+ in doped ZnS bulk and nanoparticles were reported by Chen and co-workers 35 using a fixed excitation at 767 nm. The multiphoton luminescence for the QR samples observed here using tunable excitation wavelength ranging from 990 to 730 nm demonstrated that the Mn-doped ZnS QRs could be promising bio-imaging labels in multiphoton excitation microscopy using a near-infrared (NIR) laser source, which has the advantages of deep tissue penetration and low photo-damaging effects.

In summary, we have demonstrated the synthesis of high-quality Mn-doped ZnS QRs with finely tunable diameters and doping levels using a simple, fast, and green phosphine-free colloidal chemistry. The location and the interaction of the paramagnetic Mn ions doped in the host ZnS QRs were investigated by EPR spectroscopy with modeling. The obtained Mn-doped ZnS QRs exhibit tunable dual-color emissions and three- and two-photon excitation upconversion luminescence, which make them valuable to a wide range of applications including photonic displays, sensors, lasers and biological imaging.

Example 3

Fabrication of Non-Blinking Quaternary Alloyed ZnCdSSe Cores ZnS Shell Quantum Dots with Emission Tunable in 400-700 nm For synthesis of $Cd_{0.4}Zn_{0.6}S_{0.5}Se_{0.5}$ nanocrystals, Cd/Zn-complex precursor solution was prepared by adding 4.5 mmol of ZnO and 3.0 mmol CdO into a 100 mL flask containing 10 mL paraffin liquid, 10 mL oleic acid, and 5 mL 2-ethylhexanoic acid. The mixture were heated to 100° C., degassed under 100 mtorr pressure for 30 minutes, filled with $N_2$, and further heated to 200° C. to form a clear mixture solution of Cd/Zn precursor. Then, S/Se precursor solution was prepared in a separate flask, where 0.15 mmol of S and 0.15 mmol of Se were mixed with 15 mL paraffin liquid, degassed for 30 minutes, filled with $N_2$, and heated to 280° C. At this temperature, 1 mL Cd/Zn precursor solution was quickly injected to the flask containing the above mixture. The new mixture was then maintained at 280° C. with continuous stirring. A number of aliquots (each 1 mL) can be collected in test tubes containing 2 mL cold hexane to quench further QQD growth. The samples were purified by centrifugation several times after being precipitated with pentanol and methanol. The final products were dispersed in hexane. The synthesis of other $Zn_xCd_{1-x}Se_{1-y}S_y$ quaternary nanoalloy QDs were similar, except for those of tuning the molar ratio of the Cd/Zn and S/Se source materials, The quaternary alloyed ZnCdSSe core nanocrystals were separated out by further centrifugation, and were then dissolved in 5 mL of toluene. For coating the ZnS shell onto the quaternary alloyed ZnCdSSe core, typically 1 mmol of zinc acetate (Aldrich, 99.99%) and 4 mmol of oleic acid (95%) were mixed in 50 mL of trioctylamine (TOA). It was heated to and degassed at 150° C., and further heated to 300° C. under $N_2$ flow. 5 mL of the quaternary alloyed ZnCdSSe solution in toluene was injected into the Zn-containing solution. Next, 5 mL of the S/TOP solution (0.4 M) was added at 1 mL/min, and reacted at 300° C. for 2 hours. Trioctylphosphine Sulfide (TOPS) was formed in the S/TOP solution, which slowly reacted with Zn acetate to form ZnS, which grew on the surface of ZnCdSSe seed crystals.

Example 4

Fabrication of Non-Blinking CdTe/CdS/ZnS Magic Cores/Shell/Shell Quantum Dots with Emission Tunable in 700-900 nm The magic-sized CdTe clusters with radius of ~0.8 nm were synthesized as below. Freshly prepared NaHTe solution (as Te source, 1.0 mol/L, 10 µL) was injected through a syringe to $N_2$-saturated $Cd(NO_3)_2$ solution (as Cd source, 0.005 mol/L, 50 mL) at room temperature (20° C.) in the presence of 3-mercaptopropionic acid (MPA, 37 µL) as a stabilizing agent and the sulfur source in the later step. The pH was tuned to 12.2 by adding NaOH (1M). The molar ratio of $Cd^{2+}$/MPA/NaHTe in the mixture was fixed at 1:1.7:0.04. The high Cd/Te ratio will help the growth of magic-sized CdTe clusters. Then the solution was aged at 4° C. overnight and magic-sized CdTe clusters with absorption peak at 465 nm, and photoluminescence emission peak at 480 nm were formed. These magic clusters could be purified by adding methanol and centrifugation at 15,000 rpm.

Figure 17:
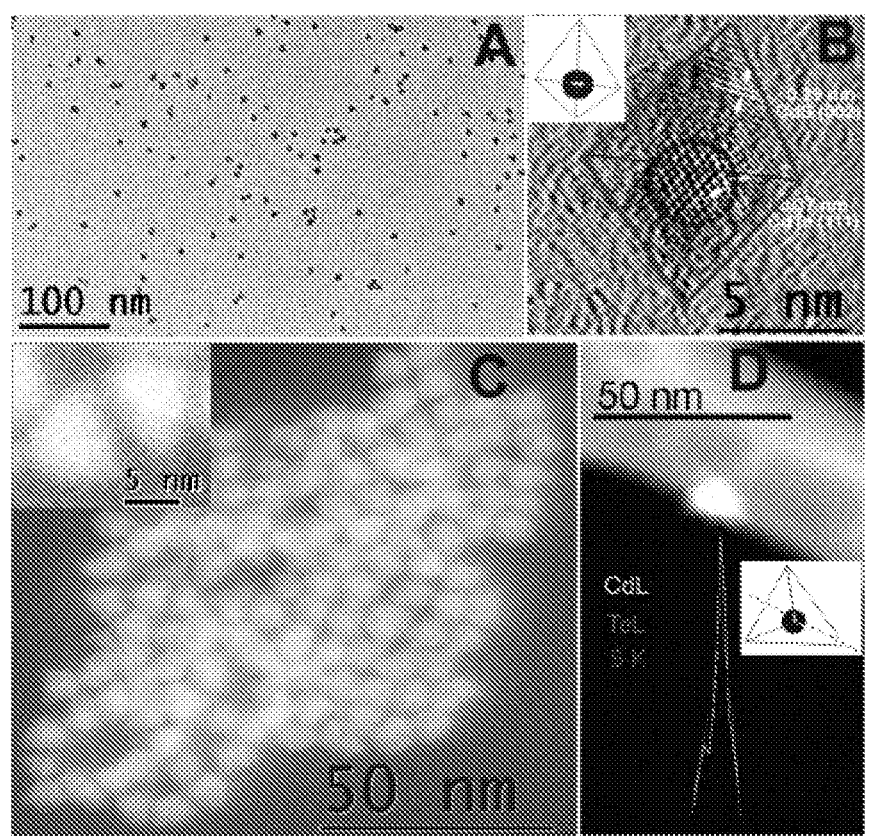
FIG. 17. (A) TEM images of the CdTe/CdS small-core/thick-shell tetrahedral-shaped quantum dots with emission maxima at 820 nm. (B) High-magnification TEM images of typical tetrahedral quantum dots; blue circles designate the CdTe cores, while red lines indicate the geometries of the tetrahedral quantum dots; the insets show schematic drawings of the quantum dots. (C) HAADF-STEM images of tetrahedral quantum dots with an emission maxima at 820 nm. (D) STEM-EDS line scan along a single tetrahedral quantum dot. The green, blue, and red patterns show the distribution of each element along the white line traversing the quantum dot. The inset contains the corresponding schematic diagram.
Figure 18:
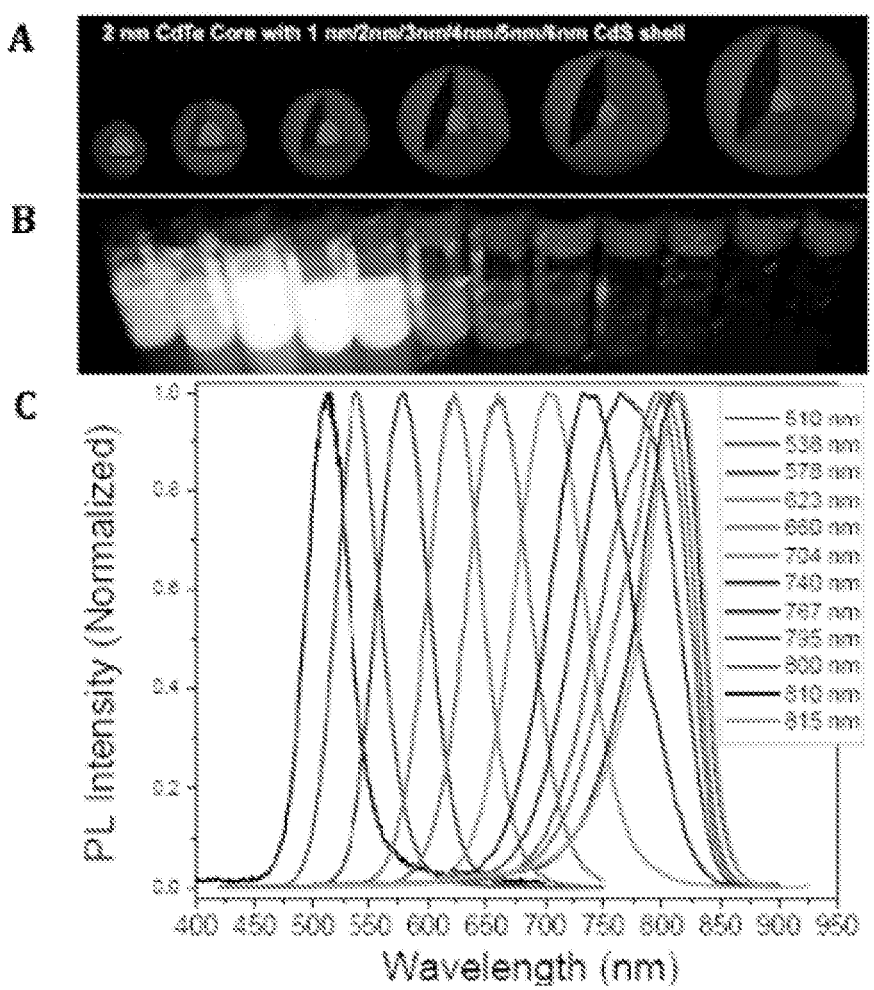
FIG. 18. (A) Schematic drawings of a series of CdTe/CdS small-core/thick-shell QDs with the same core and tunable-thickness shell; (B) the photograph of the QD samples excited with a 365 nm UV lamp; (C) the photoluminescence spectra of a series of the same QD samples with different shell sizes.

The CdTe/CdS/ZnS magic cores/shell/shell quantum dots with different shell thickness were synthesized by further aging the magic-sized CdTe clusters in the presence of solution of Cd2+/MPA (with molar ratio 1:1.7, pH 12.2) under various temperatures (from 20 to 90° C.) and various time intervals. For example, when the sample was aged at 20° C., the PL peak of the CdTe/CdS core/shell NCs shifted to 490 nm after 48 hours (See FIG. 17); if the sample was aged from 55 to 70° C. with heating speed of 0.25° C./min, the PL peak of the CdTe/CdS core/shell NCs showed a gradual shift from 505 nm to 525 nm; if the sample was kept at 90° C. for 12 hours, CdTe/CdS magic-core/thick-shell tetrahedral shaped NCs with emission at 820 nm would be obtained.

First the CdTe/CdS/ZnS magic cores/shell/shell quantum dots were precipitated with 2-propanol and then collected via centrifugation (15000 rpm). Then they are dissolved in 2 mL nanopure water and this solution was injected into the precursor solution containing $Zn^{2+}$, GSH and thiourea maintaining pH 11.5. The concentration of $Zn^{2+}$, GSH, and thiourea was 0.1 mM, 0.2 mM and 0.1 mM. The reaction mixture was heated at 90° C. and samples were collected at different interval and cooled down to 0° C.

Example 5

SnS Quantum Sheets and Quantum Ribbons

Tin(IV) iodide (SnI4, anhydrous, powder, 99.999%), Sulfur (S, powder, 99.998%), oleylamine (OAm, 70% tech.), hexamethyldisilazane (HMDS, >99%), hexane (>95%), isopropyl alcohol (IPA, 99%), methanol (>99.5%), and ethanol (99%) were purchased from Sigma-Aldrich and used without further purification.

In a typical experiment, S-OAm precursor solution was prepared in a flask, where 64 mg (2 mmol) of sulfur powder was mixed with 20 mL OAm, and stirring under low vacuum (100 mtorr) was performed in order to remove moisture and O2; the solution was subsequently heated at 100° C. for 2 hours before use. Then, 63 mg (0.10 mmol) of $SnI_4$, 10 mL (~31 mmol) of OAm, and 2 mL (9.4 mmol) of HMDS were added to a separate 100-mL three-neck round bottom flask with stirring, the solution was heated to 100° C., and degassed under 100 mtorr pressure for 30 minutes. HMDS was essential to the formation of the uniform size SnS nanocrystal products. We found that if no HMDS present, the sample will show poor crystalline (or amorphous) and very broad size distribution. Next, the flask was filled with N2 and the solution was heated to ~250° C. at 10° C./min, and 1 mL of S-OAm precursor solution was swiftly injected Timing was started immediately after injection, and the growth temperature was maintained at 250° C. After 15 minutes, the yellowish solution turned black. At this point the reaction temperature was increased to 330° C. at ~10° C./min. After remaining at this temperature for 30 min, the reaction was stopped by injection of the hot black reaction solution (2 mL) into a mixture of methanol (6 mL), ethanol (6 mL), and IPA (6 mL) at room temperature. The resulting product was centrifuged at 15,000 g and 4° C. for 30 minutes, re-dispersed in hexane (2 mL), and washed in a mixture of methanol, ethanol and IPA (1:1:1) three times by centrifugation. The final product was redispersed in hexane (2 mL) for optical measurements and structural characterization.

Ligand Exchange with Inorganic Hydrochalcogenide (HS−) Ions: The ligand exchange process was carried out in air. Colloidal dispersions of SnS nanoribbons with organic ligands were prepared in nonpolar hexane, while solutions of inorganic ligands were prepared in polar formamide (FA) immiscible with hexane. For a typical ligand exchange, using HS− ions, 0.5 mL of SnS nanoribbons solution (2 mg/mL) was mixed with 1 mL of NaHS solution (5 mg/mL). The mixture was vortexed for about 30 min leading to a complete phase transfer of SnS nanoribbons from hexane to FA phase. The phase transfer can be monitored by the color change of hexane (black to colorless) and FA (colorless to black) phases. The FA phase was separated out followed by washing with hexane three times.

Structural and Optical Characterizations: High-resolution transmission electron microscopy (HRTEM), high angle annular dark field scanning transmission electron microscopy (HAADF-STEM), and energy dispersive X-ray spectroscopy (EDS) were performed on a JEOL JEM 2010F electron microscope operating at 200 kV using ultrathin carbon coated 400 mesh copper grids or Lacey carbon coated copper grids (Ted Pella) as the sample substrates. Scanning electron microscopy (SEM) was performed using silicon as the sample substrate on a FEI FIB/SEM Nova 200 NanoLab. Powder X-ray diffraction (XRD) measurements employed a PANalytical X'Pert Pro Materials Research X-ray Diffractometer with Cu Kα radiation ($\lambda$=1.5418 Å) and scanned at a rate of 0.025 deg/s. Ultraviolet-Visible-Near Infrared (UV-Vis-NIR) absorption spectra were recorded at room temperature with a JASCO V-670 spectrophotometer equipped with an integrating sphere (Model: ISN-723, diameter: 60 mm). Samples for XRD and UV-Vis-NIR absorption characterization were prepared by drop coating of concentrated nanocrystal samples in isopropyl alcohol or hexane onto a clean glass substrate and dried in air. Fourier transform infrared spectroscopy was measured with a Thermo Nicolet 6700 FTIR (Thermo Fisher Scientific, MA) equipped with Smart orbit (a diamond single-bounce ATR accessory).

Abstract

We report the solution phase synthesis and surface processing of ~2-5 μm long single crystalline IV-VI tin(II) sulfide (SnS) ultrathin nanoribbons, with thicknesses down to 10 nm, and their use in single nanoribbon based photodetectors. The SnS nanoribbons grow via a metastable-to-stable phase transition from zinc-blende (ZB) nanospheres to orthorhombic nanoribbons; dual-phase intermediate heterostructures with zinc-blende nanosphere-heads and orthorhombic nanoribbon-tails were observed. Exchange of long, insulating organic oleylamine ligands by short, inorganic HS− ligands converts the organic SnS nanoribbons into completely inorganic, hydrophilic structures. Field-effect transistor (FET) devices were made from single SnS nanoribbons, both before and after ligand exchange, which exhibit p-type semiconductor behavior. The SnS single nanoribbon based photodetector devices showed highly sensitive and rapid photocurrent responses to illumination by blue, green and red light. The switching behavior of photocurrent generation and annihilation is complete within approximately 1 millisecond, and exhibits high photoconductivity gains (up to $2.3 \times 10^4$) and good stability. The ON/OFF ratio of the photodetector can be engineered to 80 (4 nA/50 pA) using a small drain current (10 mV) for the all inorganic SnS nanoribbons. This work paves the way for the colloidal growth of low-cost, environmentally benign, single-crystalline narrow-band-gap semiconductor nanostructures from abundant elements for applications in photodetectors and other nanoscale devices.

Introduction

Quasi-one-dimensional (quasi-1D) ribbon-like structures (nanoribbons) were found to have unusual electronic and thermal transport properties compared to one-dimensional nanowire and nanotube materials.[1-4] These fascinating materials exhibit novel physical properties owing to their unique geometries, with high aspect ratios and ultrathin thicknesses. They are the potential building blocks for a wide range of nanoscale electronics, optoelectronics, and sensing devices.[5-7] Among these, photodetectors are critical for applications as binary switches in imaging techniques and light-wave communications, as well as in future memory storage and optoelectronic circuits.[8-10]

Great efforts have been devoted to synthesize and characterize quasi-1D nanoribbons with various elemental compositions.[2, 4, 6, 7, 11-13] Parallel to the success with group IV (such as graphene[1, 14]) and groups III-V (such as BN[3, 4]) compounds, earth-abundant main-group IV-VI (IV=Ge, Sn, Pb; VI=S, Se, Te) semiconducting materials have also attracted significant attention, due to their narrow band gap and rich optical, electronic, and optoelectronic properties.[15, 16]

Synthesis of SnS nanostructures with well-defined crystallinity, size, and morphology, as well as the investigation of their optical, electrical and photoconductive properties remains a challenge. Here, we demonstrate the first colloidal synthesis of ultrathin, single crystalline SnS nanoribbons with thicknesses down to 10 nm via a unique metastable-to-stable phase transition process. We also demonstrated that a simple inorganic ligand HS− can be used to replace the original organic oleylamine ligand, imparting hydrophilicity to the structures. Field effect transistor (FET) devices based on single SnS nanoribbons were fabricated and exhibited p-type behavior. Although inorganic chalcogenide ligands have led to record high electronic transport parameters in colloidal quantum dots arrays,[36] the report here is the first time that the electronic behaviors of single 1D or quasi-1D colloidal nanostructure based devices were investigated using such a technique. Furthermore, we studied the photoconductivity of a single SnS nanoribbon based photodetector. To the best of our knowledge, this is the first example of a single SnS nanostructure based photodetector.

Results and Discussion

Figure 19:
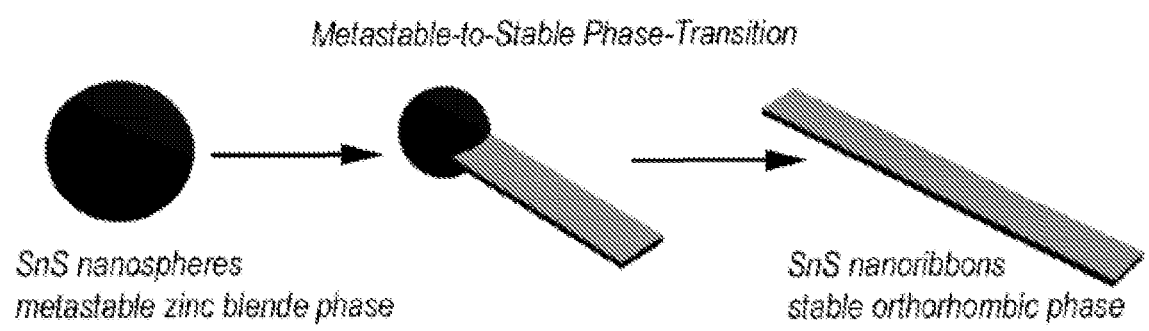
FIG. 19. Schematic illustration of the growth of a single crystalline SnS nanoribbon via a metastable to stable phase transition process. The sphere represents the metastable zinc blende phase, while the ribbon represents the stable orthorhombic phase.

The synthetic scheme we employed for the synthesis of SnS nanoribbons is based on our previously reported phosphine-free colloidal method for synthesizing II-VI nanocrystals.[37] Experimental procedures are detailed below. The resulting single-crystalline SnS nanoribbons are ~2-5 μm long and ~150-500 nm wide, with thicknesses of ~10 nm. Their formation occurs by a simple colloidal process, initiated by the injection of a sulfur-oleylamine precursor into a hot tin-oleylamine solution in the presence of hexamethyldisilazane (HMDS). During the synthesis, sequential aliquots of the reaction mixture were removed and purified to monitor the kinetics of nanoribbon formation. As shown in FIG. 19, single crystalline SnS nanoribbons formed through a unique phase transition pathway from the metastable zinc-blende phase to the stable orthorhombic phase.

Figure 20:
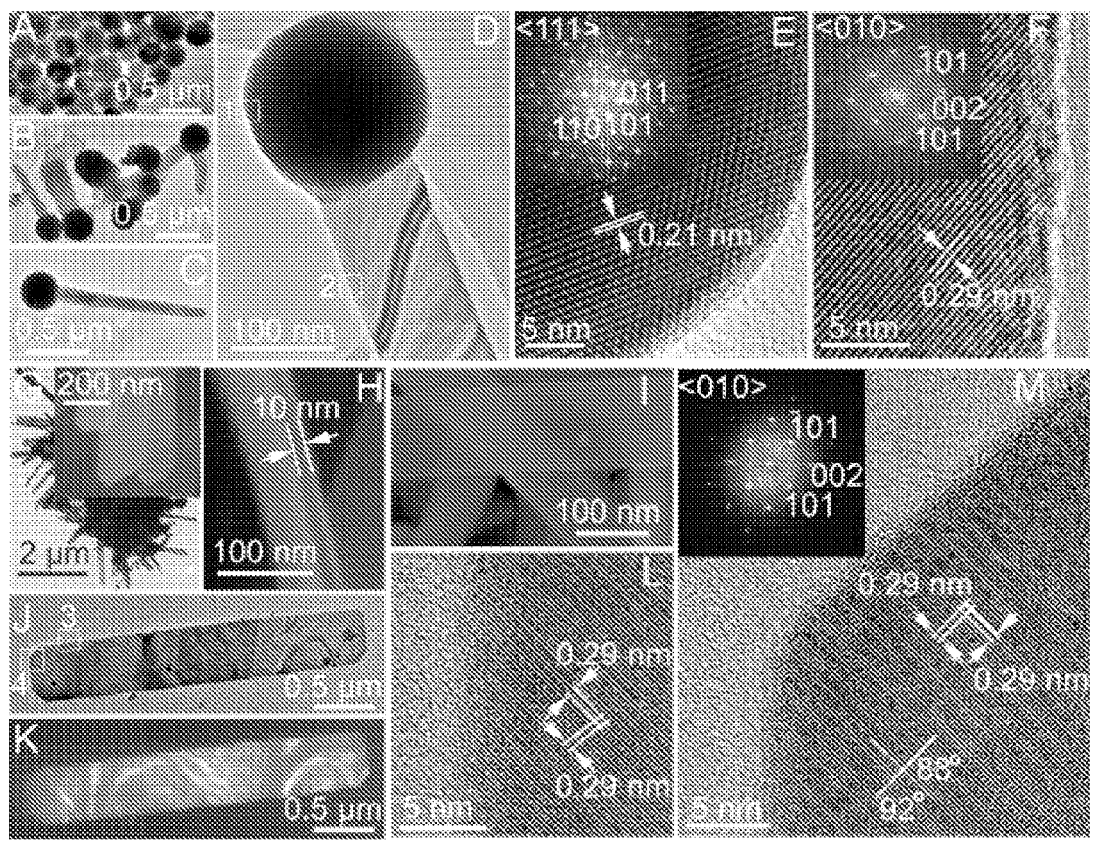
FIG. 20. (A) TEM image of the initial zinc blende SnS nanospheres; (B-D) TEM images of the intermediate dual-phase SnS heterostructures, each containing a nanosphere head and a nanoribbon tail; (E, F) HRTEM images of the head and tail regions corresponding to the boxes marked "1" and "2" in (D); (Inset in E&F) The indexed FFTs of the images in E&F; (G) TEM image of the final orthorhombic SnS nanoribbons; (Inset in G, H & I) SEM images of the final SnS nanoribbons; (J, K) Bright and dark field TEM images of a typical nanoribbon; (L, M) HRTEM images of the end and long edge corresponding to the boxes marked "3" and "4" in (J), respectively; (Inset M) indexed FFT of image M.

A black SnS product was observed 15 minutes after the injection of the sulfur-oleylamine precursor into the tin precursor solution at 250° C. The solid product was purified by centrifugation and imaged by transmission electron microscopy (TEM). Nanospheres with an average diameter of ~280 nm were obtained (FIG. 20A). High resolution TEM (HR-TEM) images of the edge of the nanospheres reveal a two dimensional lattice with typical spacing of 0.21 nm, which corresponds to the distance between (220) lattice planes of the cubic zinc blende SnS (with a crystal constant of a=0.5845 nm).[30] The X-ray diffraction (XRD) pattern (FIG. 21A, Black trace) indicates that the SnS nanospheres are zinc-blende phase with trace amounts (~5%) of orthorhombic phase present.

The temperature of the reaction mixture was elevated to 330° C. at ~10° C./min. After 10 additional minutes, intermediate SnS heterostructures with nanosphere-heads and nanoribbon-tails were observed (FIG. 20B-D). High resolution TEM (HRTEM) images (FIG. 20E) reveal that the "head" area of the heterostructure consists of a two-dimensional (2D) lattice with a zinc-blende spacing of 0.21 nm between (220) planes. The indexed fast Fourier transform (FFT) of a HRTEM image (inset in FIG. 20E) reveals a typical hexagonal pattern, indicating the SnS nanosphere "head" is single-crystalline zinc blende phase projected along the <111> direction. In contrast, a HRTEM image of the "tail" section of the heterostructure (FIG. 20F) shows a two-dimensional lattice with typical spacing of 0.29 nm, which corresponds to the distance between (101) planes of the orthorhombic phase of SnS (with a crystal constant of a=0.4329 nm, b=1.1192 nm, c=0.3894 nm, JCPDS Card No. 39-0354). The indexed FFT of this HRTEM image (inset in FIG. 20F) reveals a typical rhombic pattern, indicating that the SnS nanoribbon tail is single-crystalline orthorhombic phase projected along the <010> direction. These results clearly indicate the unique, dual-phase property of the intermediate heterostructures. Further characterization of the intermediate product by XRD (FIG. 21A) confirms a mixture of zinc-blende and orthorhombic SnS phases with a ~4:6 ratio. After 30 minutes at 330° C., all the metastable zinc-blende SnS nanospheres were transformed into stable orthorhombic SnS nanoribbons, as shown in the TEM and scanning electron microscopy (SEM) images (FIG. 20G-K). The XRD pattern of the final product (FIG. 21A) reveals highly pure orthorhombic phase SnS with no zinc-blende phase detected. Typical nanoribbons are 2~5 μm long, 150 to 500 nm wide and ~10 nm thick.

Bright field and corresponding dark field TEM images of a typical nanoribbon (FIGS. 20 J&K) reveal that the nanoribbons are single crystalline. HRTEM analysis (FIGS. 20 L&M) of both the end and side of the nanoribbon shows the same 2D lattice composition with a spacing of 0.29 nm, which corresponds to the distance between (101) planes of the orthorhombic phase of SnS. The inter-planar angles defined by the intersection of the (101) planes of the nanoribbon do not measure as 90°, but rather as 88° and 92° (FIG. 20M), which is consistent with the calculated dihedral angle between (101) and (−101).[26] The indexed FFT of the HRTEM image (inset in FIG. 20M) reveals a rhombic pattern, further confirming that the SnS nanoribbon is single-crystalline in the orthorhombic phase. These analyses confirm that the long edge of the nanoribbon is in the [001] direction with the terminating facets at the ends (001), along the sides (100) and on the faces (010). Mass calculations, before and after the phase transition, indicate that the average mass of a single SnS nanosphere (initial stage of the reaction) and a single SnS nanoribbon (final product) are nearly identical. This supports the view that the morphology change from nanosphere to nanoribbon is due to a zinc-blende to orthorhombic phase transformation within the same nanostructure.

We observed that the reaction temperature plays a crucial role in the formation of nanoribbon morphology. When the temperature is held at 330° C. for the entire reaction, rather than using an initial temperature of 250° C., 2D orthorhombic nanosheets with 200-500 nm edges and 30-60 nm thicknesses were obtained. We propose that the zinc blende nanospheres initially formed at a lower temperature act as templates and limit the final dimensions of the nanoribbons formed during the phase transition at higher temperatures. To our knowledge, the formation of single crystal SnS nanoribbons by a metastable to stable phase transition has never been reported. Odom and coworkers reported a SnS phase transition from zinc-blende tetrahedral shaped crystals to 2D orthorhombic nanosheets,[30] however, no intermediate dual phase heterostructures were observed. One literature report[38] detailed the formation of single crystalline $Sb_2Se_3$, $Sb_2Se_{3-x}S_x$ (0<x<3) and $Sb_2S_3$ nanotubes following a transition from amorphous nanospheres to orthorhombic nanotubes. It is well-known that the phase transition of a solid material results in changes to the material properties, which play an important role in a variety of processes ranging from information storage to materials processing.[39-41] In the field of semiconductor crystal growth and engineering, phase transitions from the metastable phase to the stable phase have been utilized as a novel practical route to synthesize new semiconductor materials.[42,43]

For SnS, the phase transition between metastable zinc-blende phase and stable orthorhombic phase is still largely un-explored. We believe that the following two factors may play important roles in the phase transition of SnS nanocrystals: the small size of the nanocrystals and the particular surface modifications. First, size dependent crystalline phase transitions, which can be considered as an intrinsic property of nanocrystals, exist for a wide range of materials[44]. Decreasing the size of the nanocrystals has a significant influence on the phase transition by modifying the transition energies and thus the transition temperatures. For example, the metastable zinc blende nanocrystals generated at lower temperatures can be transformed into the stable orthorhombic phase at moderately higher temperatures.[30] This is likely because the formation of the metastable zinc blende phase nanospheres is kinetically faster and dominates at lower temperatures. With a relatively lower energy barrier for the phase transition, the metastable zinc blende nanospheres can be transformed to the stable orthorhombic phase by providing the additional thermal energy. Second, by adsorbing and desorbing the capping ligand, oleylamine, on the surface of the SnS nanocrystals, the surface and/or interface energy can be modified, subsequently affecting the phase transition energy. We expect that studying the unique phase transitions in SnS nanocrystals will lead to better understanding of the mechanism behind the transitions and to new strategies for the synthesis of novel nanomaterials.

Figure 21:
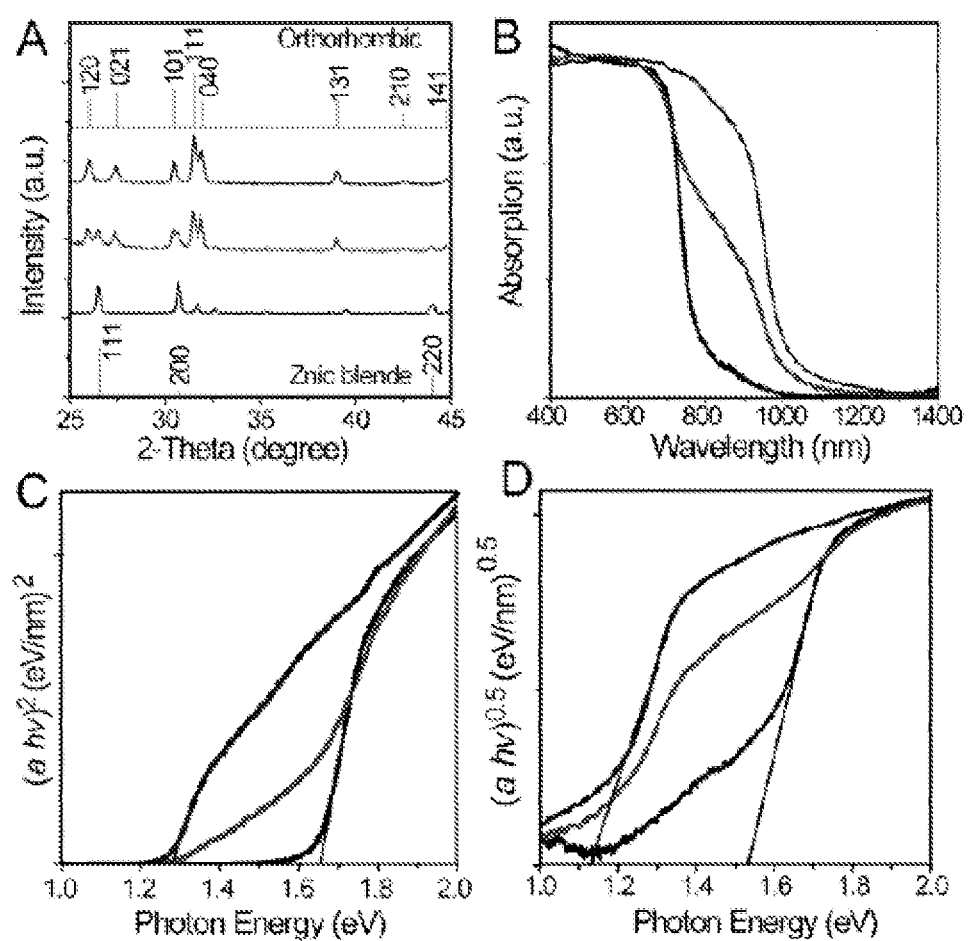
FIG. 21. (A) Powder XRD pattern of the initial SnS nanospheres (black trace), the intermediate SnS heterostructures (red trace), and the final SnS nanoribbons (blue trace). The red vertical bars along the top are indices of the orthorhombic phase of SnS crystals according to JCPDS card No. 39-0354. The black vertical bars along the bottom are indices of the zinc blende phase of SnS crystals according to literature[30]; (B-D) UV-Vis-NIR absorption spectra, plots of $(ahv)^2$ and $(ahv)^{0.5}$ versus photon energy (hv) of the initial SnS nanospheres (black trace), the intermediate SnS heterostructures (red trace), and the final SnS nanoribbons (blue trace). The spectra were recorded from powder samples drop cast at room temperature on a glass slide using a UV-Vis-NIR spectrometer equipped with an integrating sphere.

UV-Vis-NIR absorption spectroscopy was used to determine the optical properties of the SnS products at various synthesis stages (FIG. 21B). The absorption onset of the initial zinc-blende SnS nanospheres occurs around 760 nm, while the absorption onset begins around 1015 nm for the final orthorhombic phase SnS nanoribbons. The intermediate product showed the two onsets of absorption close to 760 nm and 1015 nm, consistent with its dual-phase heterostructure. To determine the direct and indirect bandgap values, Kubelka-Munk transformations were performed. A plot of $[F(R)hv]^2$ versus energy indicates a direct bandgap of 1.66 and 1.27 eV for the nanospheres and nanoribbons, respectively (FIG. 21C), while a plot of $[F(R)hv]^{0.5}$ versus energy indicates an indirect bandgap of 1.48 and 1.18 eV for the nanospheres and nanoribbons, respectively (FIG. 21D). These values match well with previously reported results for SnS.[16] Little quantum confinement effects were observed, possibly due to the relative large dimension of the nanoribbon obtained compare to the small Bohr radius of SnS ~7 nm.[35]

Figure 22:
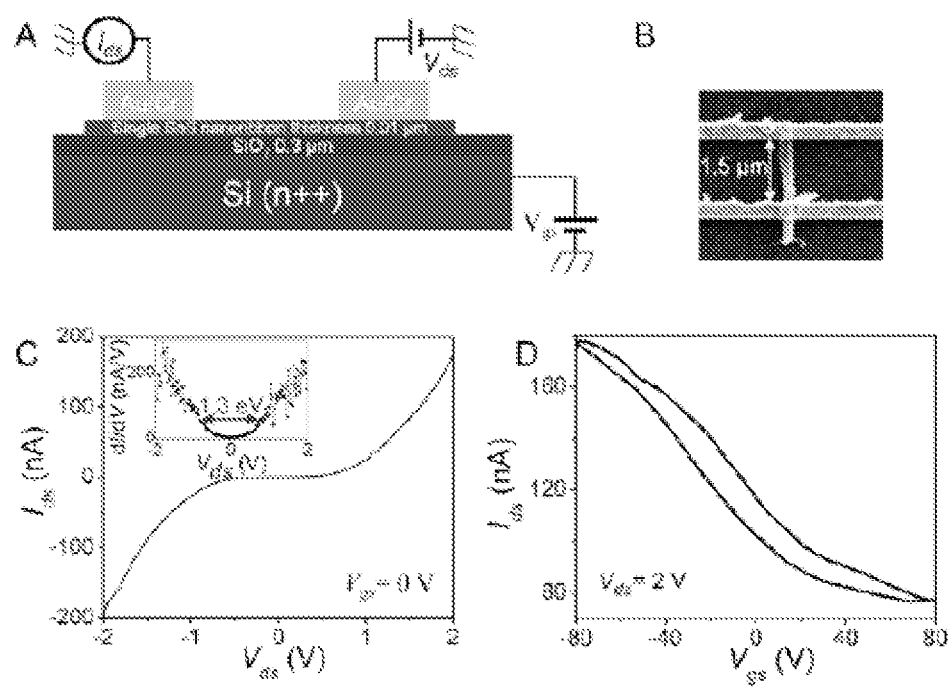
FIG. 22. (A) Schematic of a single SnS nanoribbon based field effect transistor device; (B) SEM image of a typical device. The distance between two electrodes is 1.5 μm and the width of the ribbon is about 200 nm; (C) $I_{ds}$ vs. $V_{ds}$ curve of a typical single SnS nanoribbon FET device in the dark at $V_{gs}$=0V. Top left inset in (C) shows the derivative of the I-V curve with bandgap energy of 1.3 eV. (D) $I_{ds}$ vs. $V_{gs}$ in the dark at $V_{ds}=2.0$ V of the same single nanoribbon based FET device shown in (B), exhibiting p-type semiconductor behavior.

Individual, single crystal SnS nanoribbon based optoelectronic devices were fabricated and studied in an inert gas ($N_2$ or Argon) environment using a back-gated FET configuration as shown in FIGS. 22A&B. Briefly, single nanoribbons were deposited on the surface of a highly doped n-type Si substrate covered with a 300 nm or 100 nm thick $SiO_2$ dielectric layer. The electrodes are composed of Cr (30 nm) and Au (120 nm or 150 nm), where Cr has a work function of 4.50 eV, close to that of orthorhombic SnS (4.2 eV).[45] Ten devices were fabricated and characterized. Curves of source-drain current ($I_{ds}$) vs. source-drain voltage ($V_{ds}$) were measured, and typical $I_{ds}V_{ds}$ curves at $V_{gs}=0$ for the nanoribbons are shown in FIG. 22C. A zero current region is visible at low voltage bias, suggesting the existence of an energy gap. The band gap of the SnS nanoribbon was determined to be 1.3 eV from the $dI_{ds}/dV_{ds}$ vs. $V_{ds}$ curve (inset in FIG. 22C), which is close to the direct band value of the SnS nanoribbons obtained from the optical absorption study (FIG. 21B).

FIG. 22D shows $I_{ds}$ vs. $V_{gs}$ at $V_{ds}=2V$ for the same device shown in FIG. 22B. We observed the source drain current decrease with an increase in the gate potential, suggesting the holes, rather than electrons, are the major carriers inside the SnS nanoribbon. Thus, the SnS nanoribbon based device displays p-type behavior. A small hysteresis was observed, likely originating from the water present in the atmosphere or charged impurities and contamination (such as amorphous carbon) that were incorporated during the FET device fabrication process. The transconductance $g_m(=dI_{ds}/dV_{gs})$ was acquired by fitting the linear region of the $I_{ds}$ VS. $V_{gs}$ curve. With the backgate area capacitance known and the dimensions of the nanoribbons measured from the SEM images, the hole mobility for this device was calculated based on the equation[46]

$$\mu = L/(W \times C_{ox} \times V_{ds}) \times dI_{ds}/dV_{gs} \quad (\text{Eq. 1}).$$

Figure 23:
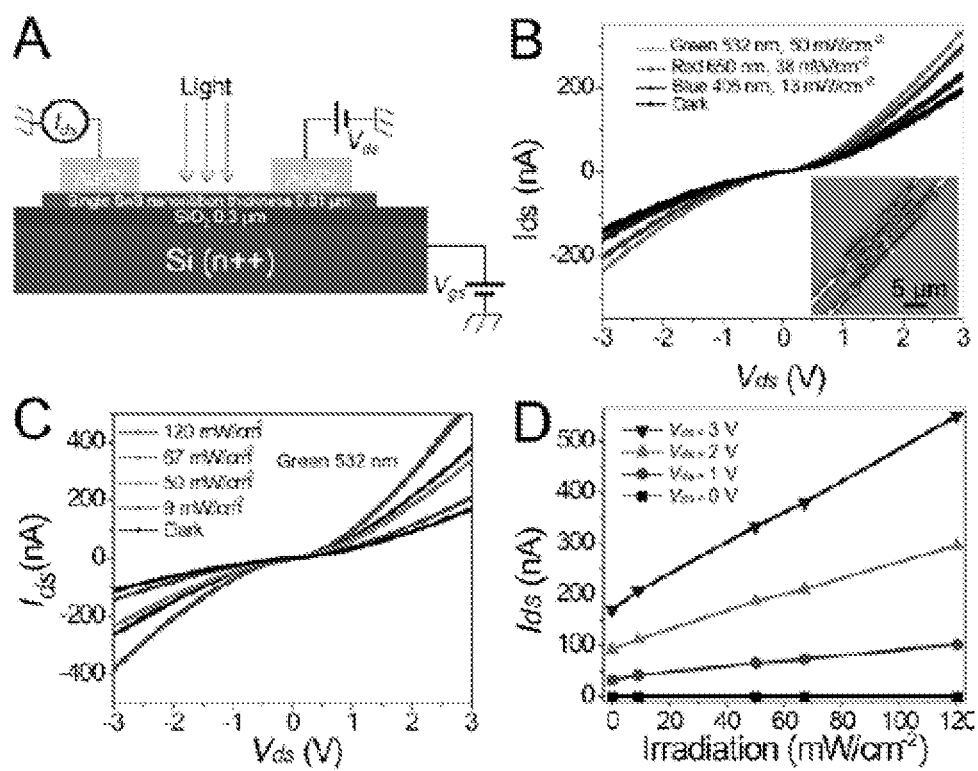
FIG. 23. (A) Schematic illustration of the single SnS nanoribbon based photodetector device configuration for photocurrent measurements. $V_{ds}$ is held between 0V and 3V, $V_{gs}$ is held at 0V, and $I_{ds}$ (between the source and drain electrodes) is monitored as light is irradiated on and off the nanoribbon surface. The laser spot is 4 mm in diameter with the irradiation controlled by clipping with a light block. (B) Typical output characteristics of the photodetector at different wavelengths of illumination: 650 nm (red), 532 nm (green), and 405 nm (blue) at $V_g=0V$; (C, D) Typical drain current ($I_{ds}$) and photocurrent ($I_{ph}$) vs. drain voltage ($V_{ds}$) of the photodetector at different illuminating optical powers of 532 nm green light with $P_{light}$ ranging from 9 to 120 mW/cm$^{-2}$ at $V_g=0V$. Inset in (B) shows an optical image of a typical photodetector device.

For the specific device reported here, the channel length L is 1.5 µm, the channel width W is 0.21 µm, the capacitance, $C_{ox}$ is $\in_o \in_r/d$ ($\in_o$ is $8.854 \times 10^{-12}$ $Fm^{-1}$, $\in_r$ for $SiO_2$ is 3.9 and d is the thickness of $SiO_2$ ~300 nm), $V_{ds}$ is 2 V, and $dI_{ds}/dV_g$ obtained from the slope of the plot of $I_{ds}$ vs. $V_g$ is $-1.23$ nA/V, as shown in FIG. 23B. The calculated hole mobility µ of this device is ca. 0.4 $cm^2V^1S^1$.

The hole concentration in the nanoribbon can be estimated by $n_h = \sigma/e\mu_h$, where σ is the conductivity (defined as the inverse of the resistivity $\rho = R \times S/L = 1.4$ Ωcm, here R is 2 V/200 nA=$1 \times 10^7$Ω, S is the vertical cross-section area of nanoribbon=10 nm×210 nm=$2.1 \times 10^{-11}$ $cm^2$, and L is the length between the electrodes 1.5 µm), e is the charge of an electron $1.6 \times 10^{-19}$ C, and $\mu_h$ is the calculated hole mobility. Thus, the hole concentration is calculated as $1.1 \times 10^{19}$ $cm^{-3}$. The p-type semiconductor behavior of the SnS nanoribbon might be due to a small amount of $Sn^{2+}$ that is substituted by $Sn^{4+}$. Derived from the calculated hole concentration, the substitution rate in the SnS nanoribbons is estimated to be ~0.003%, a value that is too low to be detected using XPS or EDS.

The FET measurements were repeated on six individual devices (fabricated with the as-synthesized nanoribbons) and revealed calculated hole mobilities ranging from 0.2 to 1.1 $cm^2V^{-1}s^{-1}$. There are options to improve the hole mobility of the colloidal single SnS nanoribbon based FET devices. For example, a top-gate FET configuration where a high dielectric gate material like $HfO_2$ is deposited on top of SnS nanoribbons could be used, as demonstrated in the single-layer $MoS_2$ based top-gate FET devices.[12] It should be noted the hole mobility of the single SnS nanoribbon FET device achieved here is comparable to the best known solution-processed organic[47] and nanocrystal[48-50] devices reported to date, and also at the same level as that of other IV-VI PbS and PbTe nanowire FET devices where the nanowires are synthesized by the chemical vapor transport (CVT) method.[51]

FIG. 23A shows the configuration of a SnS single nanoribbon photodetector for photocurrent measurements. The photoswitching characteristics and stability of single SnS nanoribbon based photodetectors were investigated in air at room temperature. Three different color lasers (532 nm light with a power intensity of 50 $mWcm^{-2}$, 650 nm light with 38 $mWcm^{-2}$, and 405 nm light with 13 $mWcm^{-2}$, respectively) were used as the light source for the device. The steady state photocurrent (under constant light illumination) was recorded while the source-drain voltage was varied between $-3V$ and $+3V$ (FIG. 23B). The device responded to all wavelengths of light, displaying increased current as compared to that in the dark. This is due to the small direct band gap energy (1.27 eV) of the SnS nanoribbons, where the electron hole pairs could be excited by all photons in the visible range. We found that the photocurrent generated from the single SnS nanoribbon photodetector depends on the power intensity of the illuminating light. FIG. 4C shows the current-voltage (I-V) curves when the power intensity ($P_{light}$) is increased from 0, 9, 50, 67, to 120 $mWcm^{-2}$. Plots of photocurrent ($I_{ph}$, the current difference with the light ON and OFF) as a function of $P_{light}$ are shown in FIG. 23D. The dependence of the photocurrent on light intensity can be fit to a power law, $I_{ph} \sim P_{light}^\theta$, where θ determines the response of the photocurrent to light intensity.[8] The fitting reveals a linear relationship with θ ~0.99 for $V_{ds}=3V$, 0.95 for $V_{ds}=2V$ and 0.93 for $V_{ds}=1V$. In such a single SnS nanoribbon based photodetector, the power law dependence of $I_{ph}$ on $P_{light}$ further confirms that the photocurrent is determined by the amount of photon-generated carriers under illumination.

Figure 24:
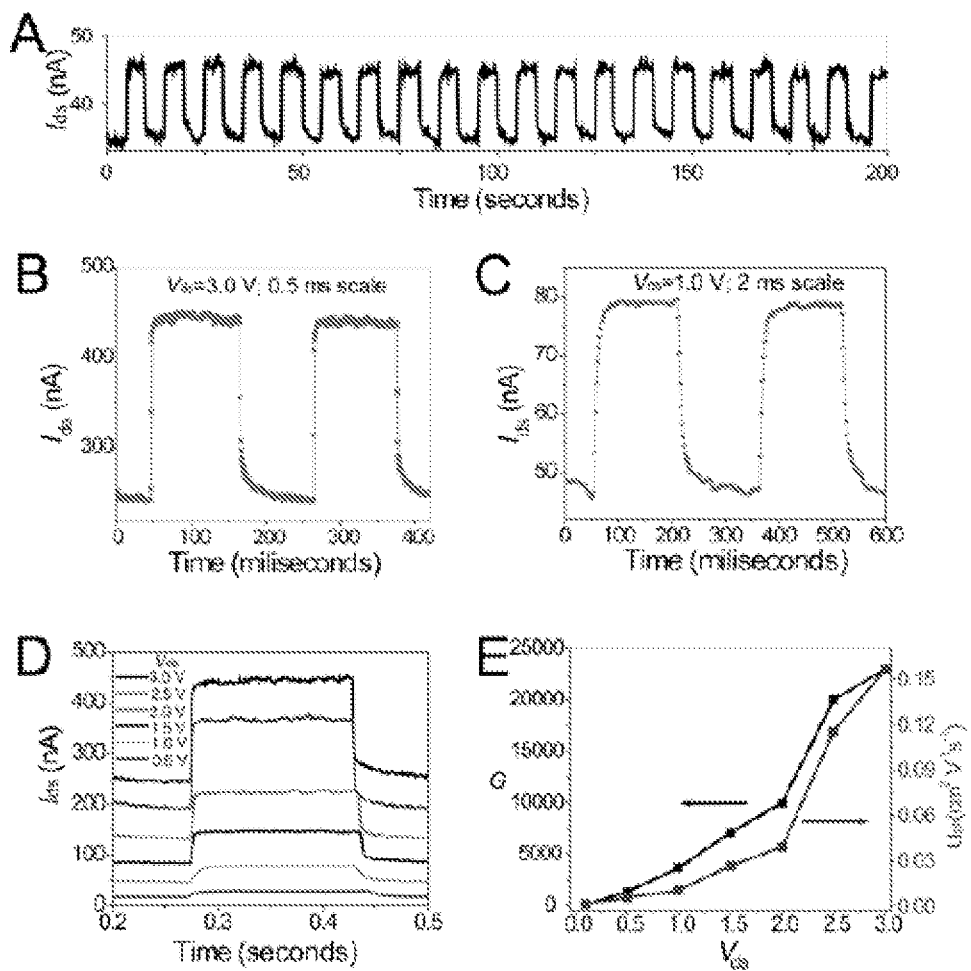
FIG. 24. (A) Stability of the photoswitching behavior of single SnS nanoribbon photodetectors at $V_{ds}=1$ V, using 532 nm light of power intensity $P_{light}=90$ mW/cm$^{-2}$. (B, C) The rise and decay rate of the photocurrent for a single SnS nanoribbon photodetector measured at $V_{ds}=3.0$ V with 0.5 ms time resolution and $V_{ds}=1.0$ V with 2 ms time resolution. The rise and decay time ($\tau_R$ and $\tau_D$) for the rise edge and decay edge of the photocurrent were obtained by fitting the curve with a single exponential equation. (D) One cycle of a single SnS nanoribbon photodetector at different drain voltages ($V_{ds}=0.5$ to 3V) under 90 mW/cm$^{-2}$ illumination. (E) The plots of the calculated gain (G) vs. drain voltages, and the mobility of the photon generated holes ($\mu_{ph}$) vs. drain voltage. As the drain voltage increases, both the G and $\mu_{ph}$ increase.

Under intermittent illumination, the current ramps to a high steady value (ON state) with light and resumes to the low value (OFF state) under dark. The stability of the photoswitching behavior was demonstrated by performing repeating pulsed illuminations on the device for 200 seconds. Steady photocurrent levels were observed after >2000-cycles of switching (FIG. 24A). The switching behavior was also investigated using different optical powers and drain voltages (FIG. 24D). With an optical power of approximately 90 $mWcm^{-2}$, the photocurrent increases from 0.8 to 200 nA as the drain voltage increases from 0.1 to 3.0 V. The dependence of photocurrent on the drain-voltage indicates that not all photon generated charge carriers can be converted to the photocurrent observed, due to recombination of the charge carriers in the nanoribbon. A larger drain voltage can drive photon generated charge carriers to reach the electrodes faster (resulting in decreased carrier transit time in the semiconductor device), thus suppressing recombination of photon generated charge carriers. With a zero gate voltage, the photoresponsivity of the single SnS nanoribbons photodetector can reach 3 μA/Wcm$^{-2}$ under illumination with a low optical power (90 mWcm$^{-2}$) and a small drain voltage (V$_{ds}$, 3V).

TABLE 2

Summary of the calculated gain (G), transit time (t$_{tran}$), and mobility of the photon generated holes (μ$_{ph}$) at different drain voltages of the SnS single nanoribbon devices.

| V$_{ds}$(V) | I$_{ph}$(nA) | τ$_D$ (ms) | G | t$_{tran}$ (μs) | μ$_{ph}$ (cm$^2$ V$^{-1}$s$^{-1}$) |
|---|---|---|---|---|---|
| 3.0 | 200 | 1.1 | 23000 | 0.048 | 0.16 |
| 2.5 | 170 | 1.5 | 20000 | 0.077 | 0.12 |
| 2.0 | 90 | 3.0 | 10000 | 0.29 | 0.039 |
| 1.5 | 62 | 4.0 | 7100 | 0.56 | 0.027 |
| 1.0 | 32 | 8.1 | 3700 | 2.2 | 0.010 |
| 0.5 | 11 | 10.5 | 1300 | 8.1 | 0.0055 |
| 0.1 | 0.8 | 14.4 | 92 | 160 | 0.0014 |

The on-off photoswitching time is a key parameter that determines the capability of a photodetector to follow a fast-varying optical signal. FIGS. 24B&C show the photoswitching behavior of single SnS nanoribbon based photodetectors with the change of photocurrent recorded on short time scales. For intrinsic semiconductors, recombination is considered as a monomolecular process, and the recombination rate is proportional to the excess of charge carriers, given by[52]

$$d\Delta n/dt = g_n - \Delta n/\tau_n \quad \text{(Eq. 2)}$$

where $g_n$ is the generation rate of charge carriers, Δn is the concentration of the excess electrons (or holes) created in the conduction- or valance bands by photon excitation, and τ$_n$ is the lifetime of charge carriers.[52] Assuming that t, is independent of n, and the electron-hole pairs are generated by direct bandgap excitation, I=I$_0$(1−e$^{-t/\tau_R}$) and I=I$_0$e$^{-t/\tau_D}$ for the photocurrent (I) at the rise (time constant T$_R$) and decay (time constant τ$_D$) edges, respectively. Both the rise and decay edges of the SnS nanoribbon device were well fit by the above exponential equations. As shown in FIG. 24B, the observed typical witching time constants for the current rise (0.94 and 0.98 ms from OFF to ON) or decay (1.09 and 1.13 ms from ON to OFF) process are on the millisecond scale.

We observed that both the rise and decay time of the photocurrent for the ON and OFF state of irradiation at different drain voltages decreases with increasing drain voltage. The average rise/decay times are 0.96/1.11, 1.23/1.51, 2.72/3.00, 3.69/3.98, 7.50/8.13, 9.66/10.47, and 12.64/14.42 ms for the drain voltage of 3.0, 2.5, 2.0, 1.5, 1.0, 0.5, and 0.10 volt, respectively. For all drain voltages, the rise time is always shorter than the corresponding decay time, which results in asymmetric curves at the rise and fall edges.

The photocurrent gain (G), defined as the number of electrons collected by electrodes due to excitation per photon, can be expressed as[52]

$$G = N_e/N_p = \tau_D/t_{tran} \quad \text{(Eq. 3)},$$

where N$_e$ is the number of electrons collected in a unit time, N$_p$ is the number of photons absorbed in a unit time, τ is the carrier lifetime obtained from τ$_R$ or τ$_D$, and t$_{tran}$ is the transit time of the charge carrier in the channel material between the electrodes. In the experiment shown in FIG. 24B, the photocurrent is approximately 200 nA for a 3V drain voltage, the light intensity is 90 mWcm$^{-2}$ at 532 nm, and the surface area of the nanoribbon is 2.25×10$^{-9}$ cm$^2$. If the absorption coefficient[53] is approximately 1×10$^5$ cm$^{-1}$, and the thickness of the device is 10 nm, then 10% of the light illuminated on the nanoribbon is absorbed.[54] Therefore, the gain of nanoribbon photoconduction G is calculated to be ~2.3×10$^4$ according to Eq. 3.

From Eq. 3, if the decay time (τ$_D$) is 1.1 ms, the transit time of the charge carriers between the electrodes, t$_{tran}$, is 48 nanoseconds for a 3V drain voltage. According to Bube et. al.[51], if the photoconductivity gain for a given material is calculated, and the carrier lifetime is known from steady-state data, the mobility of the photon generated carriers can be calculated according to $$\mu_{ph} = L^2/t_{tran} \times V_{ds}) \quad \text{(Eq. 4)}$$

where V$_{ds}$ is the applied drain voltage, L is the channel distance (1.5 μm) of the photodetector, and t$_{tran}$ is the transit time. The mobility of the photon generated carrier μ$_{ph}$ at 3V drain voltage is calculated as 0.16 cm$^2$ V$^{-1}$s$^{-1}$. For different drain voltages (from 0.1 V to 3 V), the calculated gain G, transit time t$_{tran}$, and mobility of the photon generated holes μ$_{ph}$ are listed in Table 2. We observe that as the drain voltage increases, I$_{ph}$, G, and μ$_{ph}$ also increase, while τ$_D$ and t$_{tran}$ decrease.

In a single SnS nanoribbon photodetector, the absorption of photons will excite electrons from the valence to conduction band, where the electrons and holes are separated across the SnS nanoribbon energy bandgap. If there are surface traps to remove the electrons, then excess holes are generated in the nanoribbon photodetector. The faster photoswitching speed (up to ~1 millisecond) of SnS nanoribbons compared to SnS thin films and bulk crystals (rise time of 120 second or more[55]) could be attributed to the single crystal structure of the SnS nanoribbons. First, the density of traps induced by defects inside the nanoribbon is drastically reduced, thus the photocurrent reaches a steady state rapidly in both the rise and decay stages. In addition, the ultrathin thickness of the SnS nanoribbons reduces the energy barrier for the carrier to cross the interface of the semiconductor nanoribbons and metallic electrodes (Au/Cr) due to less profound band bending at the semiconductor and metal (electrode) interface.[8] As a result, the high photocurrent is generated with a fast rise and decay lifetime. The ON/OFF ratio of the current for the SnS nanoribbon based photodetector is about 1.8, with V$_{ds}$ ranging from 0.5V to 3V, exhibiting a small voltage dependence. When the drain voltage is further decreased, the dark and light current both become too low to be measured. The ON/OFF ratio for the photodetector reported here is lower than reported by Yin et al., who used inert gas protection and thermal annealing treatment after the nanodevice fabrication.[46]

It is well known that organic ligands with long hydrocarbon chains are essential to capping the surface of nanomaterials to facilitate size and shape control during colloidal synthesis. However, these ligands may act as an insulting layer between semiconductors and electrodes, preventing effective charge transfer. We employed a ligand exchange strategy to replace the long chain organic ligands with short inorganic chalcogenide ligands yielding completely inorganic semiconductor nanomaterials. Impressively high carrier mobilities have been reported for field effect transistors devices composed of semiconductor quantum dot arrays, such as CdSe/ZnS nanocrystals, after similar ligand exchange treatment.[36]

Figure 25:
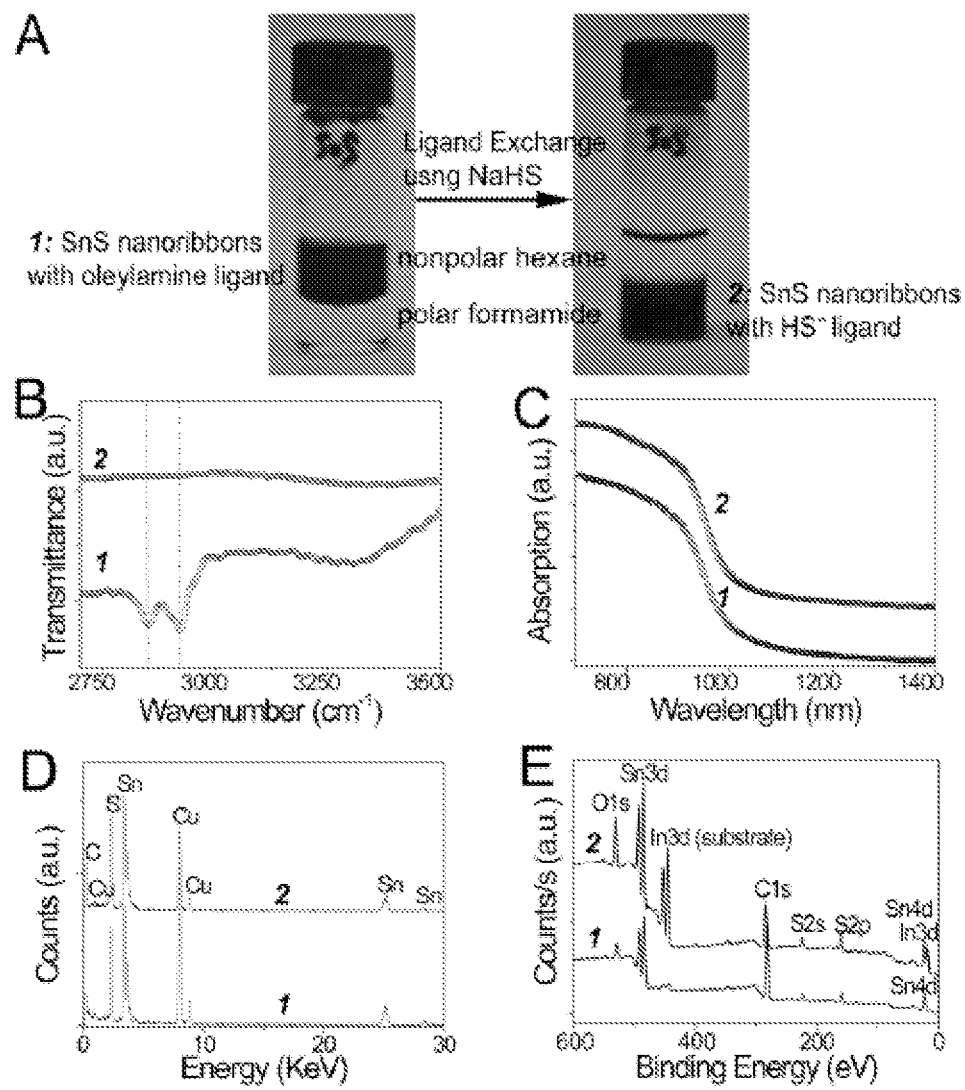
FIG. 25. (A) A colloidal dispersion of SnS nanoribbons undergoes transfer from an upper, non-polar hexane layer (density: 0.659 g/mL at 25° C.) to a lower polar, formamide layer (density: 1.134 g/mL at 25° C.) upon exchange of the original oleylamine ligands with HS$^-$ ligands; (B-E) FTIR, UV-Vis-NIR absorption, EDS and XPS spectra of SnS nanoribbons before ligand exchange (curves 1) and after ligand exchange (curves 2), respectively.

In a typical ligand exchange process, we combined a solution of oleylamine-capped SnS nanoribbons in nonpolar hexane with a solution of inorganic HS$^-$ ligands in polar formamide. The two-phase mixture containing immiscible layers of formamide and hexane was vortexed for about 30 min. After settling, complete transfer of the nanoribbons from the nonpolar solvent to formamide was observed (FIG. 25A). Fourier transform infrared spectroscopy (FTIR) spectra of SnS nanoribbons taken before and after the ligand exchange (FIG. 25B) show that the transfer of nanoribbons from hexane to formamide resulted in complete disappearance of the bands at 2852 and 2922 cm$^{-1}$, corresponding to C—H stretching in the original organic oleylamine ligands.[36] These results confirm that the original organic oleylamine ligands were completely removed by the HS$^-$ ligands and all-inorganic colloidal SnS nanoribbons were obtained. UV-Vis-NIR absorption spectrua of the SnS nanoribbons (FIG. 25C) showed no change before and after the ligand exchange, implying no changes in the size or shape of the nanoribbons. Energy-dispersive X-ray spectroscopy (EDS) spectra of the SnS nanoribbons capped with oleylamine ligands and HS$^-$ are presented for comparison in FIG. 25D. The increase in the S:Sn ratio from 0.98:1 to 1.03:1, suggests the existence of a HS$^-$ ligand layer on the surface of SnS nanoribbons after the exchange. In addition, survey X-ray photoelectron spectra (XPS) of the SnS nanoribbons revealed that the atomic ratio of S:Sn for SnS nanoribbons with OAm ligand is 0.98:1, while the atomic ratio is 1.08:1 with the HS$^-$ ligand (see FIG. 25E), consistent with the EDS analysis. The peak at 485.9 eV corresponds to the binding energy of Sn$^{2+}$3d$_{5/2}$ and the corresponding binding energy of S$^{2-}$2p$_{3/2}$ is 161.2 eV. No evidence of Sn$^{4+}$ (binding energy at 486.7 eV) is detected in the spectra.

Figure 26:
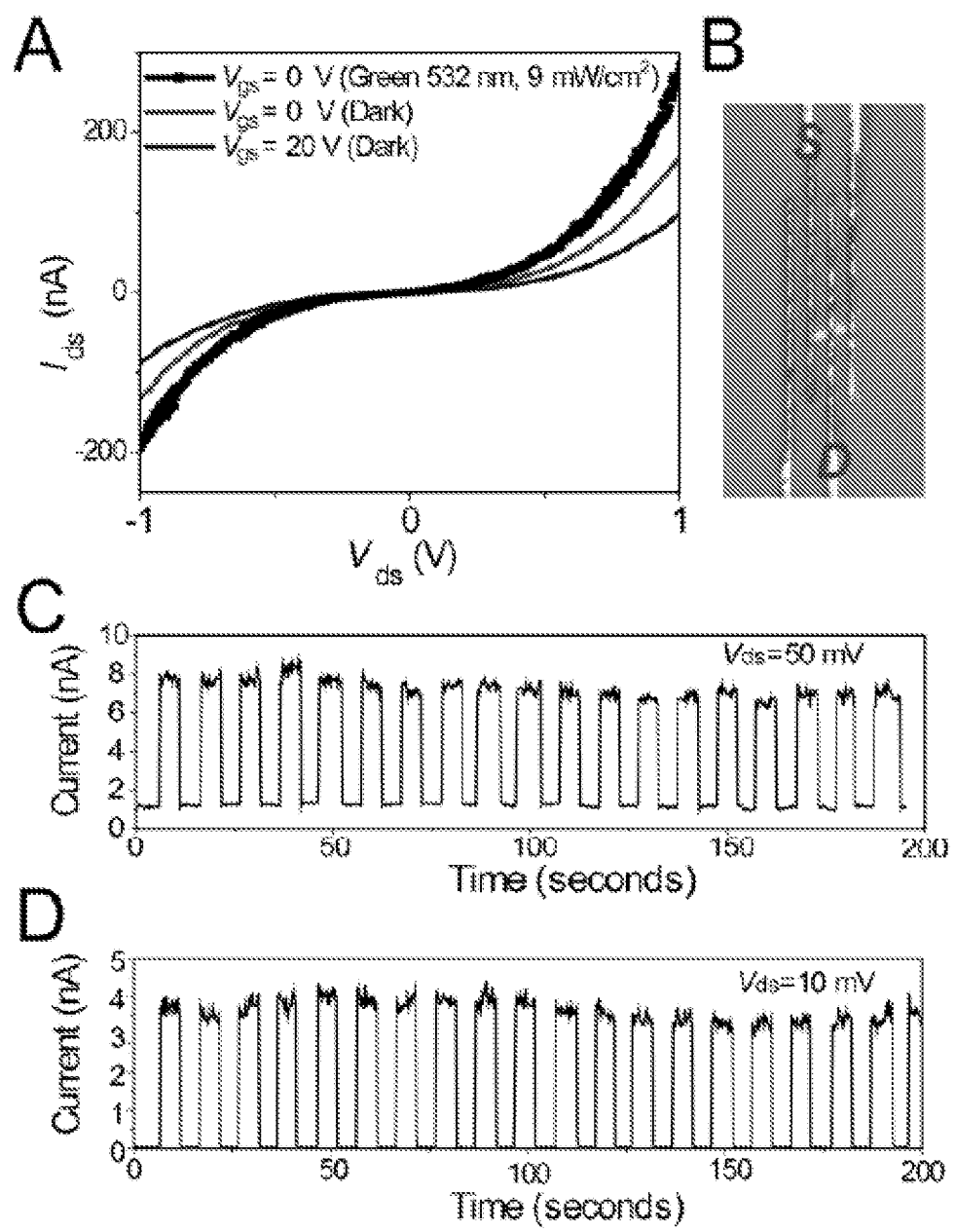
FIG. 26. (A) Typical output characteristics of SnS nanoribbon based photodetectors at difference gate voltages ($V_{gs}0$, 20V) under dark or illuminated with 532 nm light of power intensity $P_{light}=9$ mW/cm$^{-2}$ at $V_{gs}=0$ V; (B) Optical image of the single SnS nanoribbon photodetector device with labeled source and drain electrodes. (C, D) Stability test of the photoswitching behavior of single SnS nanoribbon photodetectors at $V_{ds}=50$ mV and 10 mV, illuminated with 532 nm light of power intensity $P_{light}=90$ mW/cm$^{-2}$. The ON/OFF ratio of the current is ~8 at 50 mV and ~80 at 10 mV.

We found that that after the surface ligand exchange to remove the insulating organic layer on the surface of the nanoribbon, the charge carrier mobility of the device is significantly improved to about 4 times. The performance of the HS$^-$ ligand coated nanoribbon based photodetector was analyzed as shown FIG. 26. Similar to the SnS nanoribbon based device before the ligand exchange, the all-inorganic device responded to the illumination of green light (532 nm light with power intensity P$_{light}$=90 mW/cm$^{-2}$), displaying increased current as compared to that in the dark. As the gate potential was increased the source-drain current decreased, suggesting that the HS$^-$ ligand coated SnS nanoribbon based device also displays p-type behavior. Under intermittent illumination, the current ramps to the ON state with light and resumes to the OFF state in the dark. A steady level of photocurrent was observed by applying repeating pulsed illuminations on the device for 200 seconds, which demonstrated the stability of the switching behavior (FIG. 26C, 26D). The ON/OFF ratio of the current was ~2-3 with the drain voltage ranging from 0.5-3V, but was increased to approximately 8 as the drain voltage was decreased to 50 mV (at V$_{gs}$=0 V), and reached ~80 when the drain voltage was further decreased to 10 mV. When the power intensity of the 532 nm light was reduced to 45 mW/cm$^{-2}$, the ON/OFF ratio dropped to ~40 for the same device operated under identical conditions. We found that removal of the insulating surface ligand greatly improves the contact of the electrodes to the nanoribbons, thereby increasing the photocurrent which allows the device to be operated using very small drain voltages (<10 mV). Overall, the performance of our solution processed single SnS nanoribbon photodetector is comparable to the best photodetectors reported, including single CdSe nanoribbons[52], single CdS nanoribbon,[56] PbS nanocrystals[57], etc.[8]

Conclusion

In summary, we present the controlled colloidal synthesis of high quality single crystalline SnS nanoribbons through a metastable to stable phase transition process. Optical measurements show that the onset of absorption of the initial ZB nanospheres occurs at 760 nm (1.63 eV), while the absorption begins at 1015 nm (1.22 eV) for the final orthorhombic phase nanoribbons. Simple inorganic HS$^-$ ligands were used to successfully replace the original organic oleylamine ligand. The photoconductive characteristics of SnS single nanoribbons were investigated, which demonstrate highly sensitive and rapid response to illumination by blue, green and red light at room temperature. Switching between photocurrent generation and annihilation is complete within 1 millisecond, and is accompanied by high photoconductivity gains (up to 2.3× 10$^4$). The ON/OFF ratio of the photodetector can be engineered to 80 (4 nm/50 pA) using a small drain current (10 mV). We found that the drain voltage has a significant influence on the photoswitching speed with higher voltages exhibiting faster photoswitching rates. These desirable properties can be attributed to the high single-crystal quality and large surface-to-volume ratio of the ultrathin SnS nanoribbons. This work reinforces the potential application of low cost, less toxic and earth abundant IV-VI colloidal semiconductor nanostructures in optical, electronic, and optoelectronic devices.

Materials and Methods

Materials and Synthesis. Tin(IV) iodide (SnI$_4$, anhydrous, powder, 99.999%), sulfur (S, powder, 99.998%), oleylamine (OAm, 70% tech.), hexamethyldisilazane (HMDS, ≥99%), sodium hydrosulfide (NaHS, ≥90%), formamide (HCONH$_2$, ≥99.5%), hexane (≥95%), isopropyl alcohol (IPA, 99%), methanol (≥99.5%), and ethanol (99%) were purchased from Sigma-Aldrich and used without further purification. In a typical experiment, S-OAm precursor solution was prepared in a flask, where 64 mg (2 mmol) of sulfur powder was mixed with 20 mL OAm, and stirring under low vacuum (100 mtorr) was performed in order to remove moisture and O$_2$; the solution was subsequently heated at 100° C. for 2 hours before use. Then, 63 mg (0.10 mmol) of SnI$_4$, 10 mL (~31 mmol) of OAm, and 2 mL (9.4 mmol) of HMDS were added to a separate 100-mL three-neck round bottom flask with stirring, the solution was heated to 100° C., and degassed under 100 mtorr pressure for 30 minutes. HMDS was essential to the formation of the uniform size SnS nanocrystal products. We found that if no HMDS present, the sample will show poor crystalline (or amorphous) with very broad size distribution. Next, the flask was filled with N$_2$ and the solution was heated to ~250° C. at 10° C./min, and 1 mL of S-OAm precursor solution was swiftly injected. Timing was started immediately after injection, and the growth temperature was maintained at 250° C. After 15 minutes, the yellowish solution turned black. At this point the reaction temperature was increased to 330° C. at ~10° C./min. After remaining at this temperature for 30 min, the reaction was stopped by injection of the hot black reaction solution (2 mL) into a mixture of methanol (6 mL), ethanol (6 mL), and IPA (6 mL) at room temperature. The resulting product was centrifuged at 15,000 g and 4° C. for 30 minutes, re-dispersed in hexane (2 mL), and washed in a mixture of methanol, ethanol and IPA (1:1:1) three times by centrifugation. The final product was re-dispersed in hexane (2 mL) for optical measurements and structural characterization. The overall yield of the SnS nanoribbons is estimated to be 60% by compassion of the mass of final product and initial source materials used.

Ligand exchange. The ligand exchange process was carried out in air. Colloidal dispersions of SnS nanoribbons with organic ligands were prepared in nonpolar hexane, while solutions of inorganic ligands were prepared in polar formamide, immiscible with hexane. For a typical ligand exchange, 0.5 mL of SnS nanoribbons solution (2 mg/mL) was mixed with 1 mL of NaHS solution (5 mg/mL). The mixture was vortexed for 10 to 30 min leading to a complete phase transfer of SnS nanoribbons from hexane to formamide phase. The phase transfer can be monitored by the color change of hexane (black to colorless) and formamide (colorless to black) phases. The formamide phase was separated out by carefully removing the top hexane layer by a syringe, then followed by more washing steps: adding more hexane (hexane:formamide 1:1 volume ratio), mixing them by vortex, settling and removing the top hexane layer by a syringe. We did not observe any oxidation and dissolution during the ligand exchange process.

Characterizations. High-resolution transmission electron microscopy (HRTEM), high angle annular dark field scanning transmission electron microscopy (HAADF-STEM), and energy dispersive X-ray spectroscopy (EDS) were performed on a JEOL JEM 2010F electron microscope operating at 200 kV using ultrathin carbon coated 400 mesh copper grids or Lacey carbon coated copper grids (Ted Pella) as the sample substrates. Scanning electron microscopy (SEM) was performed using silicon as the sample substrate on a FEI FIB/SEM Nova 200 NanoLab. Powder X-ray diffraction (XRD) measurements employed a PANalytical X'Pert Pro Materials Research X-ray Diffractometer with Cu Kα radiation ($\lambda$=1.5418 Å) and scanned at a rate of 0.025 deg/s. Ultraviolet-Visible-Near Infrared (UV-Vis-NIR) absorption spectra were recorded at room temperature with a JASCO V-670 spectrophotometer equipped with an integrating sphere (Model: ISN-723, diameter: 60 mm) Samples for XRD and UV-Vis-NIR absorption characterization were prepared by drop coating of concentrated nanocrystal samples in isopropyl alcohol or hexane onto a clean glass substrate and dried in air. Fourier transform infrared spectroscopy was measured with a Thermo Nicolet 6700 FTIR (Thermo Fisher Scientific, MA) equipped with Smart orbit (a diamond single-bounce ATR accessory).

Device fabrication and measurements. Metal (Au) markers for position registration were first fabricated by electron beam lithography (EBL) on n-type silicon substrates with 300 nm thermal silicon dioxide. The SnS nanoribbons were dispersed in hexane (before ligand exchange) or ethanol (after ligand exchange) and transferred to the substrates by a pipette. The nanoribbons remained on the $SiO_2$ surface after the solvent evaporation. After determining the position of each nanoribbon by SEM with the aid of metal markers, source-drain electrodes (30 nm Cr and 120 nm/150 nm Au) were fabricated by EBL. The electrical measurements were conducted with a Keithley 2636A in a faraday cage under $N_2$ or Argon gas protection. The hole mobility is calculated to be $0.4\pm0.1$ cm$^2$ V$^{-1}$s$^{-1}$ with nanoribbons before ligand exchange, and improved to $0.9\pm0.2$ cm$^2$ V$^{-1}$s$^{-1}$ with ribbons after ligand exchange. Multiple devices (>10) have been fabricated and measured to obtain the reproducible results. All photocurrent measurements were performed in air and at room temperature.

References for Example 5
1. Han, M. Y.; Ozyilmaz, B.; Zhang, Y. B.; Kim, P., Energy band-gap engineering of graphene nanoribbons. *Phys. Rev. Lett.* 2007, 98, 206805.
2. Li, X. L.; Wang, X. R.; Zhang, L.; Lee, S. W.; Dai, H. J., Chemically derived, ultrasmooth graphene nanoribbon semiconductors. *Science* 2008, 319, 1229-1232.
3. Chen, Z. G.; Zou, J.; Liu, G.; Li, F.; Wang, Y.; Wang, L. Z.; Yuan, X. L.; Sekiguchi, T.; Cheng, H. M.; Lu, G. Q., Novel Boron Nitride Hollow Nanoribbons. *ACS Nano* 2008, 2, 2183-2191.
4. Zeng, H. B.; Zhi, C. Y.; Zhang, Z. H.; Wei, X. L.; Wang, X. B.; Guo, W. L.; Bando, Y.; Golberg, D., "White Graphenes": Boron Nitride Nanoribbons via Boron Nitride Nanotube Unwrapping. *Nano Lett.* 2010, 10, 5049-5055.
5. Schwierz, F., Graphene transistors. *Nat. Nanotechnol.* 2010, 5, 487-496.
6. Higginbotham, A. L.; Kosynkin, D. V.; Sinitskii, A.; Sun, Z. Z.; Tour, J. M., Lower-Defect Graphene Oxide Nanoribbons from Multiwalled Carbon Nanotubes. *ACS Nano* 2010, 4, 2059-2069.
7. Kosynkin, D. V.; Lu, W.; Sinitskii, A.; Pera, G.; Sun, Z. Z.; Tour, J. M., Highly Conductive Graphene Nanoribbons by Longitudinal Splitting of Carbon Nanotubes Using Potassium Vapor. *ACS Nano* 2011, 5, 968-974.
8. Zhai, T.; Li, L.; Wang, X.; Fang, X. S.; Bando, Y.; Golberg, D., Recent Developments in One-Dimensional Inorganic Nanostructures for Photodetectors. *Adv. Funct. Mater.* 2010, 20, 4233-4248.
9. Kind, H.; Yan, H. Q.; Messer, B.; Law, M.; Yang, P. D., Nanowire ultraviolet photodetectors and optical switches. *Adv. Mater.* 2002, 14, 158-160.
10. Soci, C.; Zhang, A.; Bao, X. Y.; Kim, H.; Lo, Y.; Wang, D. L., Nanowire Photodetectors. *J. Nanosci. Nanotechnol.* 2010, 10, 1430-1449.
11. Sinitskii, A.; Dimiev, A.; Corley, D. A.; Fursina, A. A.; Kosynkin, D. V.; Tour, J. M., Kinetics of Diazonium Functionalization of Chemically Converted Graphene Nanoribbons. *ACS Nano* 2010, 4, 1949-1954.
12. Radisavljevic, B.; Radenovic, A.; Brivio, J.; Giacometti, V.; K is, A., Single-layer MoS(2) transistors. *Nat. Nanotechnol.* 2011, 6, 147-150.
13. Coleman, J. N.; Lotya, M.; O'Neill, A.; Bergin, S. D.; King, P. J.; Khan, U.; Young, K.; Gaucher, A.; De, S.; Smith, R. J.; et al., Two-Dimensional Nanosheets Produced by Liquid Exfoliation of Layered Materials. *Science* 2011, 331, 568-571.
14. Xia, F. N.; Mueller, T.; Lin, Y. M.; Valdes-Garcia, A.; Avouris, P., Ultrafast graphene photodetector. *Nat. Nanotechnol.* 2009, 4, 839-843.
15. Habas, S. E.; Platt, H. A. S.; van Hest, M. F. A. M.; Ginley, D. S., Low-Cost Inorganic Solar Cells: From Ink To Printed Device. *Chem. Rev.* 2010, 110, 6571-6594.
16. Antunez, P. D.; Buckley, J. J.; Brutchey, R. L., Tin and germanium monochalcogenide IV-VI semiconductor nanocrystals for use in solar cells. *Nanoscale* 2011, 3, 2399-2411.
17. Xu, Y.; Al-Salim, N.; Bumby, C. W.; Tilley, R. D., Synthesis of SnS Quantum Dots. *J. Am. Chem. Soc.* 2009, 131, 15990-15991.
18. Baumgardner, W. J.; Choi, J. J.; Lim, Y.-F.; Hanrath, T., SnSe Nanocrystals: Synthesis, Structure, Optical Properties, and Surface Chemistry. *J. Am. Chem. Soc.* 2010, 132, 9519-9521.
19. Zhu, H. L.; Yang, D. R.; Ji, Y. J.; Zhang, H.; Shen, X. F., Two-dimensional SnS nanosheets fabricated by a novel hydrothermal method. *J. Mater. Sci.* 2005, 40, 591-595.
20. Koktysh, D. S.; McBride, J. R.; Rosenthal, S. J., Synthesis of SnS nanocrystals by the solvothermal decomposition of a single source precursor. *Nanoscale Res. Lett.* 2007, 2, 144-148.
21. Wang, Z. J.; Qu, S. C.; Zeng, X. B.; Liu, J. P.; Zhang, C. S.; Tan, F. R.; Jin, L.; Wang, Z. G., The application of SnS nanoparticles to bulk heterojunction solar cells. *J. Alloys Compd.* 2009, 482, 203-207.
22. Franzman, M. A.; Schlenker, C. W.; Thompson, M. E.; Brutchey, R. L., Solution-Phase Synthesis of SnSe Nanocrystals for Use in Solar Cells. *J. Am. Chem. Soc.* 2010, 132, 4060-4061.
23. Reddy, N. K.; Devika, M.; Ahsanulhaq, Q.; Gunasekhar, K. R., Growth of Orthorhombic SnS Nanobox Structures on Seeded Substrates. *Cryst. Growth Des.* 2010, 10, 4769-4772.
24. Ehlert, O.; Thomann, R.; Darbandi, M.; Nann, T., A four-color colloidal multiplexing nanoparticle system. *ACS Nano* 2008, 2, 120-124.
25. Donega, C. D. M., Synthesis and properties of colloidal heteronanocrystals. *Chem. Soc. Rev.* 2011, 40, 1512-1546.

26. Vaughn, D. D.; In, S. I.; Schaak, R. E., A Precursor-Limited Nanoparticle Coalescence Pathway for Tuning the Thickness of Laterally-Uniform Colloidal Nanosheets: The Case of SnSe. *ACS Nano* 2011, 5, 8852-8860.
27. Kang, J. G.; Park, J. G.; Kim, D. W., Superior rate capabilities of SnS nanosheet electrodes for Li ion batteries. *Electrochem. Commun.* 2010, 12, 307-310.
28. Ning, J. J.; Xiao, G. J.; Jiang, T.; Wang, L.; Dai, Q. Q.; Zou, B.; Liu, B. B.; Wei, Y. J.; Chen, G.; Zou, G. T., Shape and size controlled synthesis and properties of colloidal IV-VI SnSe nanocrystals. *Crystengcomm* 2011, 13, 4161-4166.
29. Zhang, Y.; Lu, J.; Shen, S.; Xu, H.; Wang, Q., Ultralarge single crystal SnS rectangular nanosheets. *Chem. Comm.* 2011, 47, 5226-5228.
30. Greyson, E. C.; Barton, J. E.; Odom, T. W., Tetrahedral zinc blende tin sulfide nanoand microcrystals. *Small* 2006, 2, 368-371.
31. Yue, G. H.; Lin, Y. D.; Wen, X.; Wang, L. S.; Chen, Y. Z.; Peng, D. L., Synthesis and characterization of the SnS nanowires via chemical vapor deposition. *Appl. Phys. A-Mater.* 2012, 106, 87-91.
32. Zhang, H. L.; Hu, C. G.; Wang, X.; Xi, Y.; Li, X. Y., Synthesis and photosensitivity of SnS nanobelts. *J. Alloys Compd.* 2012, 513, 1-5.
33. Deng, Z. T.; Han, D. R.; Liu, Y., Colloidal synthesis of metastable zinc-blende IV-VI SnS nanocrystals with tunable sizes. *Nanoscale* 2011, 3, 4346-4351.
34. Panda, S. K.; Datta, A.; Dev, A.; Gorai, S.; Chaudhuri, S., Surfactant-assisted synthesis of SnS nanowires grown on tin foils. *Cryst. Growth Des.* 2006, 6, 2177-2181.
35. Yue, G. H.; Wang, L. S.; Wang, X.; Chen, Y. Z.; Peng, D. L., Characterization and Optical Properties of the Single Crystalline SnS Nanowire Arrays. *Nanoscale Res. Lett.* 2009, 4, 359-363.
36. Nag, A.; Kovalenko, M. V.; Lee, J.-S.; Liu, W.; Spokoyny, B.; Talapin, D. V., Metal-free Inorganic Ligands for Colloidal Nanocrystals: S(2-), HS(-), Se(2-), HSe(-), Te(2-), HTe(-), TeS(3)(2-), OH(-), and NH(2)(-) as Surface Ligands. *J. Am. Chem. Soc.* 2011, 133, 10612-10620.
37. Deng, Z. T.; Yan, H.; Liu, Y., Controlled Colloidal Growth of Ultrathin Single-Crystal ZnS Nanowires with a Magic-Size Diameter. *Angew. Chem. Int. Ed.* 2010, 49, 8695-8698.
38. Deng, Z.; Mansuripur, M.; Muscat, A., Simple Colloidal Synthesis of Single-Crystal Sb—Se—S Nanotubes with Composition Dependent Band-Gap Energy in the Near-Infrared. *Nano Lett.* 2009, 9, 2015-2020.
39. Alivisatos, A. P., Semiconductor clusters, nanocrystals, and quantum dots. *Science* 1996, 271, 933-937.
40. Polking, M. J.; Urban, J. J.; Milliron, D. J.; Zheng, H.; Chan, E.; Caldwell, M. A.; Raoux, S.; Kisielowski, C. F.; Ager, J. W., III; Ramesh, R.; et al., Size-Dependent Polar Ordering in Colloidal GeTe Nanocrystals. *Nano Lett.* 2011, 11, 1147-1152.
41. Zheng, H.; Rivest, J. B.; Miller, T. A.; Sadtler, B.; Lindenberg, A.; Toney, M. F.; Wang, L.-W.; Kisielowski, C.; Alivisatos, A. P., Observation of Transient Structural-Transformation Dynamics in a Cu(2)S Nanorod. *Science* 2011, 333, 206-209.
42. Brus, L., Solid state chemistry—Metastable dense semiconductor phases. *Science* 1997, 276, 373-374.
43. Deng, Z. T.; Bao, Z. X.; Cao, L.; Chen, D.; Tang, F. Q.; Wang, F. F.; Liu, C. X.; Zou, B. S.; Muscat, A. J., Spherical hexagonal tellurium nanocrystals: fabrication and size-dependent structural phase transition at high pressure. *Nanotechnology* 2008, 19, 045707.
44. Smith, A. M.; Nie, S. M., Semiconductor Nanocrystals: Structure, Properties, and Band Gap Engineering. *Acc. Chem. Res.* 2010, 43, 190-200.
45. Devika, M.; Reddy, N. K.; Patolsky, F.; Gunasekhar, K. R., Ohmic contacts to SnS films: Selection and estimation of thermal stability. *J. Appl. Phys.* 2008, 104, 124503.
46. Yin, Z. Y.; Li, H.; Jiang, L.; Shi, Y. M.; Sun, Y. H.; Lu, G.; Zhang, Q.; Chen, X. D.; Zhang, H., Single-Layer $MoS_2$ Phototransistors. *ACS Nano* 2012, 6, 74-80.
47. Coropceanu, V.; Cornil, J.; da Silva Filho, D. A.; Olivier, Y.; Silbey, R.; Bredas, J.-L., Charge transport in organic semiconductors. *Chem. Rev.* 2007, 107, 926-952.
48. Talapin, D. V.; Lee, J. S.; Kovalenko, M. V.; Shevchenko, E. V., Prospects of Colloidal Nanocrystals for Electronic and Optoelectronic Applications. *Chem. Rev.* 2010, 110, 389-458.
49. Fafarman, A. T.; Koh, W. K.; Diroll, B. T.; Kim, D. K.; Ko, D. K.; Oh, S. J.; Ye, X. C.; Doan-Nguyen, V.; Crump, M. R.; Reifsnyder, D. C.; et al., Thiocyanate-Capped Nanocrystal Colloids: Vibrational Reporter of Surface Chemistry and Solution-Based Route to Enhanced Coupling in Nanocrystal Solids. *J. Am. Chem. Soc.* 2011, 133, 15753-15761.
50. Koh, W. K.; Saudari, S. R.; Fafarman, A. T.; Kagan, C. R.; Murray, C. B., Thiocyanate-Capped PbS Nanocubes: Ambipolar Transport Enables Quantum Dot Based Circuits on a Flexible Substrate. *Nano Lett.* 2011, 11, 4764-4767.
51. Liang, W.; Hochbaum, A. I.; Fardy, M.; Rabin, O.; Zhang, M.; Yang, P., Field-Effect Modulation of Seebeck Coefficient in Single PbSe Nanowires. *Nano Lett.* 2009, 9, 1689-1693.
52. Jiang, Y.; Zhang, W. J.; Jie, J. S.; Meng, X. M.; Fan, X.; Lee, S. T., Photoresponse properties of CdSe single-nanoribbon photodetectors. *Adv. Funct. Mater.* 2007, 17, 1795-1800.
53. Sugiyama, M.; Reddy, K. T. R.; Revathi, N.; Shimamoto, Y.; Murata, Y., Band offset of SnS solar cell structure measured by X-ray photoelectron spectroscopy. *Thin Solid Films* 2011, 519, 7429-7431.
54. Vidal, J.; Lany, S.; d'Avezac, M.; Zunger, A.; Zakutayev, A.; Francis, J.; Tate, J., Band-structure, optical properties, and defect physics of the photovoltaic semiconductor SnS. *Appl. Phys. Lett.* 2012, 100, 032104.
55. Johnson, J. B.; Jones, H.; Latham, B. S.; Parker, J. D.; Engelken, R. D.; Barber, C., Optimization of photoconductivity in vacuum-evaporated tin sulfide thin films. *Semicond. Sci. Technol.* 1999, 14, 501-507.
56. Jie, J. S.; Zhang, W. J.; Jiang, Y.; Meng, X. M.; Li, Y. Q.; Lee, S. T., Photoconductive characteristics of single-crystal CdS nanoribbons. *Nano Lett.* 2006, 6, 1887-1892.
57. Konstantatos, G.; Clifford, J.; Levina, L.; Sargent, E. H., Sensitive solution-processed visible-wavelength photodetectors. *Nat. Photon.* 2007, 1, 531-534.

Example 6

SnS-FET Device Fabrication and Mobility Calculation

Metal (Au) markers for position registration were first fabricated by electron beam lithography (EBL) on n-type silicon substrates with 300 nm thermal dioxide. The SnS nanoribbons were dispersed in hexane (before ligand exchange) or ethanol (after ligand exchange) and transferred to the substrates by a pipette. The nanoribbons remained on the $SiO_2$ surface after the solvent evaporation. After determining the position of each nanoribbon by SEM with the aid of metal markers, source-drain electrodes (30 nm Cr and 120 nm/150 nm Au) were fabricated by EBL. The electrical measurements were conducted with a Keithley 2636A in a faraday cage under N2 or Argon gas protection. We followed a common method in literature to extract the carrier mobility from the electrical transport measurement. The transconductance (gm=dIds/dVgs) was obtained from the slope by fitting the linear region of the IdsVgs curve. The carrier concentration is calculated by $n_h=\sigma/\mu_h$ at the current saturation region of the IdsVgs curve for a p-type semiconductor. We estimated the hole concentration to be $5.8\times10^{18}$ cm$^{-3}$ using the conductivity value at Vgs=−80V. The mobility was calculated by $\mu=g_m L/(C_g V_{ds} W)$, where Cg is the backgate capacitance per unit channel area, W and L is the width and length of the channel (nanoribbon) as determined from the SEM images. Here the Cg is mainly from the 300 nm SiO2 layer and therefore Cg=$1.15\times10^{-4}$F/m$^2$. The obtained mobility are calculated to be 0.25 cm2 V$^{-1}$s$^{-1}$ with nanoribbons before ligand exchange, and improved to 1.11 cm$^2$ V$^{-1}$s$^{-1}$ with ribbons after ligand exchange. Multiply devices (>10) have been fabricated and measured to obtain the reproducible results.

Example 7

Core CdTe QDs were firstly prepared by adding freshly prepared NaHTe solution to N$_2$-saturated Cd(NO$_3$)$_2$ solutions at pH 11 in the presence of simple thiol molecular (such as mercaptopropionic acid, MPA) as a stabilizing agent. During refluxing of the reaction mixture with the temperature close to 100° C., a series of CdTe core QDs with their size ranging from 2.0 to 6.0 nm could be obtained. The thiol-modified DNA was conjugated to QD during the CdTe/CdS core-shell QDs synthesis. Typically, an aqueous solution containing a calculated mount of CdCl$_2$, MPA, and thiol-modified DNA was added to aqueous solution containing thiourea and CdTe core QDs, and then the final pH value of the reaction mixture was adjusted to 11.5. The air in the system was pumped off and replaced with N$_2$. Subsequently, the reaction mixture was refluxed under N$_2$ atmosphere, and timing started. Aliquots of the DNA modified CdTe/CdS core-shell QDs samples were removed from the reaction vessel at regular intervals, rapidly cooled to room temperature, and stored at 4° C. in the dark. The QD-DNA conjugate samples where then loaded on an agarose gel. Due to the negative charge of the DNA, the conjugates run to the positive electrode (to the right of the gel). From the gel we can clearly see that the QD-DNA conjugate run into the gel with a well distinguished band. QDs without DNA conjugation cannot run into the gel and diffuse away from the well. Importantly, we also observed that the DNA-QD conjugates reserved their photoluminescence after the conjugation.

We claim:
1. A nanocrystal comprising,
  (i) a core comprising CdTe;
  (ii) a first coating, substantially covering the surface of the core, comprising CdS; and
  (iii) a second coating, substantially covering the surface of the first coating, comprising ZnS,
wherein the nanocrystal has a photoluminescence maximum between about 650 nm and 900 nm.
2. The nanocrystal of claim 1, wherein the core has a diameter between about 1.0 nm and 20 nm.
3. The nanocrystal of claim 1, wherein the first coating has a thickness between about 1 nm and 10 nm.
4. The nanocrystal of claim 1, wherein the second coating, when present, has a thickness between about 0.3 and 10 nm.
5. The nanocrystal of claim 1, further comprising a monolayer formed over the surface of the nanocrystal, the monolayer comprising molecules of the formula, X-Y-Z, wherein X is a functional group capable of reacting with or coordinating with the surface of the nanocrystal; Y is a divalent linking group; and Z is a functional molecule.
6. The nanocrystal of claim 5, wherein X is a thiol or carboxylic acid group.
7. The nanocrystal of claim 5, wherein Z is one half of a specific binding pair.
8. The nanocrystal of claim 7, wherein Z is a nucleic acid, avidin, streptavidin, biotin, a protein, an enzyme antagonist, agonist, partial agonist, or partial antagonist, or an antigen.
9. The nanocrystal of claim 1 that is non-blinking.

* * * * *